US006962805B2

(12) United States Patent
Asakura et al.

(10) Patent No.: US 6,962,805 B2
(45) Date of Patent: Nov. 8, 2005

(54) METHOD OF CONSTRUCTING AMINO ACID PRODUCING BACTERIAL STRAINS, AND METHOD OF PREPARING AMINO ACIDS BY FERMENTATION WITH THE CONSTRUCTED AMINO ACID PRODUCING BACTERIAL STRAINS

(75) Inventors: Yoko Asakura, Kawasaki (JP); Jun Nakamura, Kawasaki (JP); Sohei Kanno, Kawasaki (JP); Mikiko Suga, Kawasaki (JP); Eiichiro Kimura, Kawasaki (JP); Hisao Ito, Kawasaki (JP); Kazuhiko Matsui, Kawasaki (JP); Tsuyoshi Ohsumi, Tokyo (JP); Tsuyoshi Nakamatsu, Kawasaki (JP); Osamu Kurahashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/577,005

(22) Filed: May 25, 2000

(65) Prior Publication Data

US 2004/0002143 A1 Jan. 1, 2004

Related U.S. Application Data

(63) Continuation of application No. PCT/JP99/05175, filed on Sep. 22, 1999.

(30) Foreign Application Priority Data

Sep. 25, 1998 (JP) .......................................... 10-271786
Sep. 25, 1998 (JP) .......................................... 10-271787

(51) Int. Cl.$^7$ .......................... C12P 13/14; C07H 21/04; C12Q 1/32; C12N 15/74; C12N 1/20
(52) U.S. Cl. .................... 435/110; 536/23.1; 536/23.2; 536/24.1; 435/26; 435/69.1; 435/189; 435/190; 435/471; 435/252.32; 435/232; 435/193
(58) Field of Search ............................ 536/23.1, 23.2, 536/24.1; 435/26, 69.1, 190, 110, 471, 252.32, 189, 232, 193

(56) References Cited

FOREIGN PATENT DOCUMENTS

| CN | 1155300 | 7/1997 |
|---|---|---|
| EP | 0 771 879 | 5/1997 |
| EP | WO00/18935 | 4/2000 |
| JP | 61-104790 | 5/1986 |
| JP | 63-214189 | 9/1988 |
| JP | 6-502548 | 3/1994 |
| JP | 2708168 | 10/1997 |
| WO | WO 93/03158 | 2/1993 |

OTHER PUBLICATIONS

Bormann et al., GenBank accession No. X59404, 1992.*
Eikmanns et al., GenBank accession No. X66112, 1994.*
Nakamura et al., GenBank accession No. AB025424, Apr. 1999.*
Eikmanns et al., GenBank accession No. X71489, 1995.*
Lewin, Genes IV, pp. 225–226, 1990.*
Bork, Genome Research, 10:398–400, 2000.*
Broun et al., Science 282:1315–1317, 1998.*
Seffernick et al., J. Bacteriol. 183(8):2405–2410, 2001.*
Van de Loo et al., Proc. Natl. Acad. Sci. 92:6743–6747, 1995.*
Baggio et al., GenEMBL accession No. BTU82241, Jan. 11, 1997.*
Teller et al., GenEMBL accession No. CLOSGDHG, Jun. 30, 1993.*
B. Fournier, et al., "Strength and Regulation of the Different Promoters for Chromosomal β–Lactamases of *Klebsiella oxytoca*", Antimicrobial Agents and Chemotherapy, vol. 43, No. 4, Apr. 1999, p. 850–855.
T. Jeffke, et al., "Mutational Analysis of the CBB Operon ($CO_2$ Assimilation) Promoter of Ralstonia Eutropha", Journal of Bacteriology, vol. 181, No. 14, Jul. 1999, p. 4374–4380.
C. Guerrero, et al., Gene, vol. 138, XP–002285948, pp. 35–41, "Directed Mutagenesis of a Regulatory Palindromic Sequence Upstream from the Brevibacterium Lactofermentum Tryptophan Operon", 1994.
K. Sano, et al., Gene, vol. 53, XP–002285949, pp. 191–200, "Structure and Function of the TRP Operon Control Regions of Brevibacterium Lactofermentum, a Glutamic–Acid–Producing Bacterium", 1987.
E.M.T. El–Mansi, "Control of Metabolic Interconversion of Isocitrate Dehydrogenase Between the Catalytically Active and Inactive Forms in *Escherichia coli*", FEMS Microbiology Letters, 166, (1998), 333–339.
E. Alvarez–Villafane, et al., "Two $NAD^+$–Isocitrate Dehydrogenase Forms in Phycomyces Blakesleeanus, Induction in Response to Acetate Growth and Characterization, Kinetics, and Regulation of Both Enzyme Forms", Biochemistry, 1996, 35, 4741–4752.

(Continued)

*Primary Examiner*—Rebecca E. Prouty
*Assistant Examiner*—Delia M. Ramirez
(74) *Attorney, Agent, or Firm*—Shelly Guest Cemaik

(57) ABSTRACT

A method of producing coryneform bacteria having improved amino acid or nucleic acid productivity comprising the steps of introducing a mutation in a promoter sequence of amino acid- or nucleic acid-biosynthesizing genes on a chromosome of a coryneform bacterium to make it close to a consensus sequence, or introducing a change in a promoter sequence of amino acid- or nucleic acid-biosynthesizing genes on a chromosome of a coryneform bacterium by gene recombination to make it close to a consensus sequence, to obtain mutants of the coryneform amino acid- or nucleic acid-producing microorganism, culturing the mutants and selecting a mutant capable of producing the intended amino acid or nucleic acid in a large amount. This method allows the construction of a mutant capable of enriching or controlling the expression of an intended gene without using a plasmid and to promote production of amino acids in a high yield by recombination or mutation.

26 Claims, 3 Drawing Sheets

OTHER PUBLICATIONS

R.F. Cadenas, et al., Gene, vol. 98, pps. 117–121, "Construction and Characterization of Promoter–Probe Vectors for Corynebacteria Using the Kanamycin–Resistance Reporter Gene," 1991.

A. Cid, et al. Current Genetics, vol. 12, pps. 105–110, "Replacement of the Promoter of the Yeast Plasma Membrane ATPase Gene by a Galactose–Dependent Promoter and its Physiological Consequences," 1987.

R.E. Dalbey, et al., The Journal of Biological Chemistry, vol. 260, No. 29, pps. 15925–15931, "Leader Peptidase Catalyzes the Release of Exported Proteins From the Outer Surface of the *Escherichia coli* Plasma Membrane," Dec. 15, 1965.

G. Miozzari, et al., Proc. Natl. Acad. Sci., vol. 75, No. 11, pps. 5580–5584, "Naturally Occurring Promoter Down Mutation: Nucleotide Sequence of the TRP Promoter/Operator/Leader Region of *Shigella dysenteriae* 16," Nov. 1978.

Y. Morinaga, et al., Journal of Biotechnology, vol. 5, pps. 305–312, "Expression of *Escherichia coli* Promoters in Brevibacterium Lactofermentum Using the Shuttle Vector pEB003," 1987.

M. Patek, et al., Microbiology, vol. 142, pps. 1297–1309, "Promoters From Corynebacterium Glutamicum: Cloning, Molecular Analysis and Search for a Consensus Motif," 1996.

O. Raibaud, et al., Gene, vol. 29, pps. 231–241, "A Technique for Integrating any DNA Fragment Into the Chromosome of *Escherichia coli*" 1984.

M. Rosenberg, et al., Ann. Rev. Genet. vol. 13, pps. 319–353, "Regulatory Sequences Involved in the Promotion and Termination of RNA Transcription," 1979.

H. Shimotsu, et al., Gene, vol. 43, pps. 85–94, Construction of a Single–Copy Integration Vector and its use in Analysis of Regulation of the TRP Operon of *Bacillus subtilis*.

S. Sugimoto, et al., Journal of Biology, vol. 5, pps. 237–253, "Hyperproduction of Phenylalanine by *Escherichia coli*: Application of a Temperature–Controllable Expression Vector Carrying the Repressor–Promoter System of Bacteriophage Lambda," 1987.

P. Youderian, et al., Cell, vol. 30, pps. 843–853, "Sequence Determinants of Promoter Activity," Oct. 1982.

T.J. Zupancic, et al., FEMS Microbiology Letters, vol. 131, pps. 121–126, "Isolation of Promoters From *Brevibacterium flavum* Strain MJ233C and Comparison of Their Gene Expression Levels in *B. Flavum* and *Escherichia coli*," 1995.

* cited by examiner

METHOD OF CONSTRUCTING AMINO ACID PRODUCING BACTERIAL STRAINS, AND METHOD OF PREPARING AMINO ACIDS BY FERMENTATION WITH THE CONSTRUCTED AMINO ACID PRODUCING BACTERIAL STRAINS

This application is a continuation of PCT/JP99/05175 filed Sep. 22, 1999.

BACKGROUND OF THE INVENTION

1. Field of the Invention

The present invention relates to a method of constructing a mutant strain capable of producing amino acids in a high yield, and a method of producing L-amino acids by the fermentation with the mutant.

2. Description the Background

Methods of constructing mutant strains usable for the production of amino acids by the fermentation can be roughly classified into two methods. One of them comprises introducing random mutations into DNA with a chemical mutagen, and the other comprises the genetic recombination. In the latter method, a strain having an improved capacity of producing an intended substance can be developed by enhancing a gene on a metabolic pathway relating to the biosynthesis of an intended substance, or by weakening a gene of an enzyme relating to the destruction. In this connection, for enhancing an intended gene, a plasmid capable of autonomously replicating independently from the chromosome in a cell has been mainly used.

However, the method of enhancing the intended gene with a plasmid has problems. In particular, the degree of enrichment of the intended gene is variable depending on the number of copies of the plasmid itself. Therefore, for some kinds of intended genes, the copies are often too many in number and, as a result, the expression becomes excessive, the growth is seriously inhibited or the capacity of producing the intended substance is lowered. In such a case, although the degree of the enhancement of the intended gene can be lowered by using a plasmid of a small number of the copies, the variety of the plasmid is limited in many cases, and the intended control of the expression level of the intended gene is impossible.

Another problem is that since the replication of the plasmid is often unstable, the plasmid is eliminated.

For example, Japanese Patent Unexamined Published Application (hereinafter referred to as "J.P. KOKAI") No:61-268185 discloses a recombinant DNA comprising a DNA fragment containing a glutamate dehydrogenase (GDH)-producing gene (glutamate dehydrogenase gene) derived from a glutamate-producing coryneform bacterium, and a DNA fragment (plasmid) containing a gene necessary for the autonomous replication in the cell. It is also disclosed therein that by introducing the recombinant DNA into a cell, a GDH-enriching strain can be grown to improve the production of substances (such as amino acids and proteins) with microorganisms.

On the other hand, in Japanese Patent No. 2,520,895, the above described recombinant DNA is introduced into Corynebacterium to obtain a strain having the improved enzymatic activity, and L-glutamic acid is produced by the fermentation with the strain. However, the production and yield of L-glutamic acid were yet unsatisfactory. Thus, it is demanded to further improve the productivity of L-glutamic acid. It is reported that the demand had been attained by introducing a recombinant DNA comprising two kinds of genes, i.e. a glutamate dehydrogenase-producing gene derived from a glutamate-producing coryneform bacterium, and an isocitrate dehydrogenase (ICDH)gene, into a glutamate-producing coryneform bacterium.

Further, JP Kokai No. 6-502548 discloses an expression system and a secretion system of *Corynebacterium* comprising a *Corynebacterium* strain and a secretory cassette comprising the first functional DNA sequence for the expression in the strain, the second DNA sequence encoding for amino kids, polypeptides and/or proteins and the third DNA sequence inserted between the first DNA sequence and the second DNA sequence, wherein the third DNA sequence encodes the protein element selected from PS1 and PS2 which guarantee the secretion of the amino acids, polypeptides and/or proteins. Specifically, the secretion of polypeptides is disclosed therein and in particular, NTG mutagenesis was conducted with *Corynebacterium* and a mutant resistant to 4-fluoroglutamate (4FG) which is an analogue to glutamate is selected and subjected to the transformation with POGL141. It is described therein that a strain having an enhanced expression of GDH can be obtained from the analogue resistant bacteria. It is also described therein that a mutation was observed in nucleotide sequence No. 251 to No. 266 of GDH promoter.

SUMMARY OF THE INVENTION

The object of the present invention is to provide a method of constructing a mutant capable of suitably enhancing or controlling the expression of an intended gene without using a plasmid and also capable of producing amino acids in a high yield, by gene recombination or mutation.

Another object of the present invention is to provide a promoter for GDH capable of imparting a capability of producing glutamic acid in a high yield to a Corynebacterium strain without seriously increasing the amount of by-produced aspartic acid and alanine.

Still another object of the present invention is to provide a GDH gene having a sequence of the above-described promoter for GDH.

A further object of the present invention is to provide a Corynebacterium strain having the above-described gene and capable of producing I-glutamic acid.

A further object of the present invention is to provide a method of producing amino acids by fermentation wherein amino acid-producing microorganism thus constructed is used.

A further object of the present invention is to provide a fermentation method of producing glutamic acid at a low cost by increasing the yield of glutamic acid by using a glutamic acid-producing coryneform bacterium.

DETAILED DESCRIPTION OF THE PREFERRED EMBODIMENT

The present invention has been completed on the basis of a finding that the above-described problems can be efficiently solved by variously modifying the promoter of amino acid-biosynthesizing genes on a chromosome to control the amount of the expression of the intended genes. Particularly, the invention has been completed on the basis of a finding that the above-described problem can be efficiently solved by introducing a specific mutation into −35 region or −10 region which is a specific region of the promoter.

Namely, the present invention provides a method of producing coryneform bacteria having an improved amino acid- or nucleic acid-productivity, which comprises the steps of introducing a mutations in a promoter sequence of amino acid- or nucleic acid-biosynthesizing genes on a chromosome of a coryneform bacteria to make it close to a consensus sequence or introducing a change in a promoter sequence of amino acid- or nucleic acid-biosynthesizing genes on a chromosome of Coryneform bacteria by gene recombination to make it close to a consensus sequence, to obtain mutants of the coryneform amino acid- or nucleic acid-producing microorganism, culturing the mutants, and selecting a mutant capable of producing the intended amino acid or nucleic acid in a large amount.

The present invention also provides a promoter for glutamate dehydrogenase (GDH)-producing gene, which has the sequence of (i) at least one DNA sequence selected from the group consisting of CGGTCA, TTGTCA, TTGACA and TTGCCA in −35 region, (ii) TATAAT sequence or the same TATAAT sequence but in which the base of ATAAT is replaced with another base in −10 region, or (iii) a combination of (i) and (ii), wherein the sequence does not inhibit the promoter function.

The present invention also provides a glutamate dehydrogenase-producing gene having the above-described promoter.

The present invention also provides a coryneform L-glutamate-producing microorganism having the above-described gene.

The present invention also provides a process for producing an amino acid by the fermentation, which comprises the steps of culturing a coryneform bacterium constructed by the above-described method and having an improved amino acid-producing capacity in a medium to form and also to accumulate the intended amino acid in the medium, and collecting the amino acid from the medium.

The present invention also provides a process for producing L-glutamic acid by the fermentation, which comprises the steps of culturing a coryneform L-glutamic acid-producing microorganism resistant to 4-fluoroglutamic acid in a liquid medium to form and also to accumulate L-glutamic acid in the medium, and collecting L-glutamic acid from the medium.

BEST MODE FOR CARRYING OUT THE INVENTION

Figure 1:
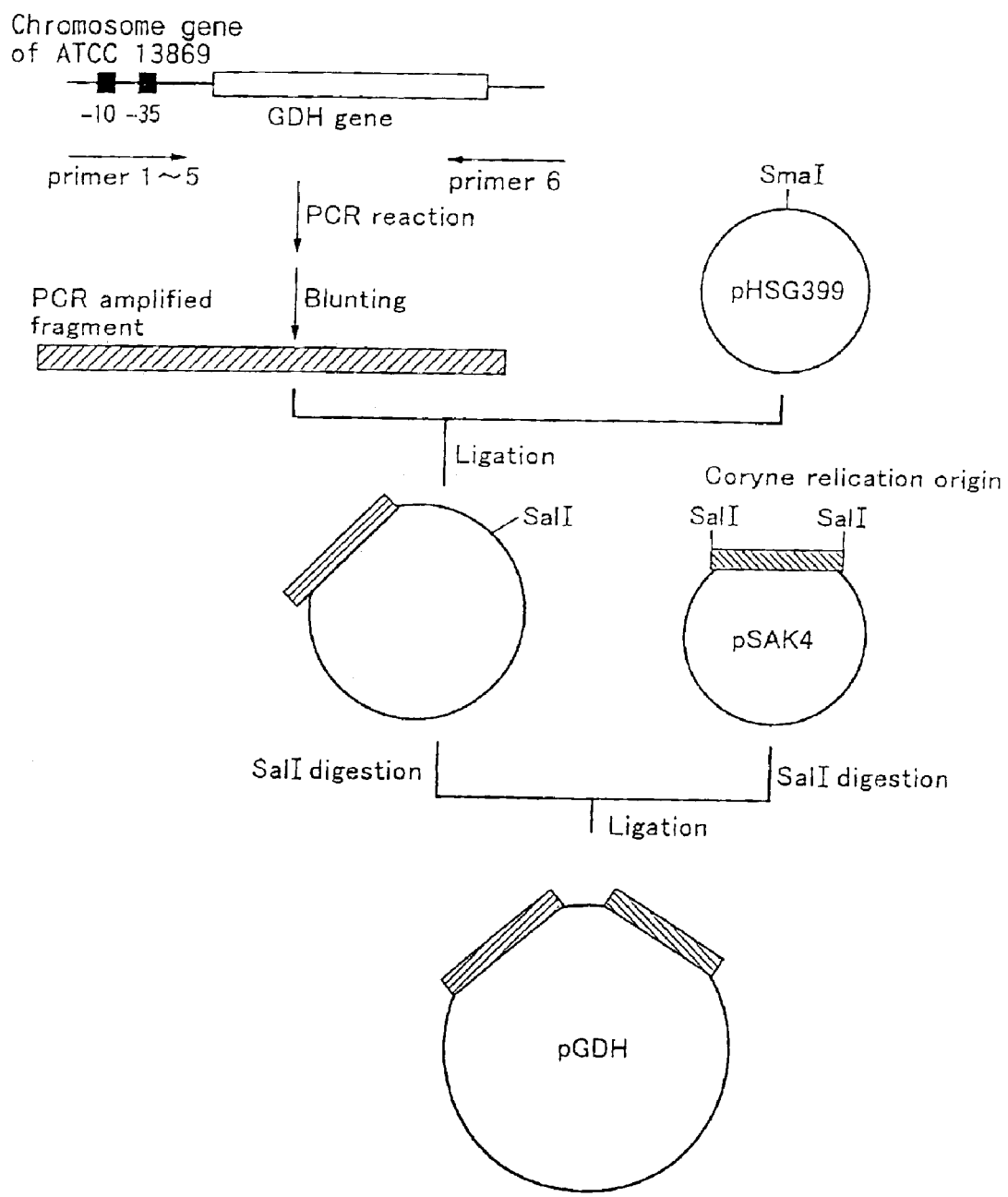
FIG. 1 show a flow of construction of GDH gene having a mutant promoter.

The term "coryneform glutamic acid producing microorganism" as used herein includes also bacteria which were classified to be the genus Brevibacterium before but now integrated into the genus Corynebacterium [Int. J. Syst. Bacteriol., 41, 255 (1981)] and also bacteria of the genus Brevibacterium which are very close to those of the genus Corynebacterium. Therefore, the mutants used in the present invention can be derived from the coryneform glutamic acid-producing bacteria of the genus Brevibacterium or Corynebacterium shown below. Bacteria of the genus Corynebacterium and those of the genus Brevibacterium will be collectively referred to as "coryneform bacteria" so far as they do not concern the glutamic acid productivity.

| | |
|---|---|
| Corynebacterium acetoacidophilum | ATCC13870 |
| Corynebacterium acetoglutamicum | ATCC15806 |
| Corynebacterium callunae | ATCC15991 |
| Corynebacterium glutamicum | ATCC13032 |
| Brevibacterium divaricatum | ATCC14020 |
| Brevibacterium lactofermentum | ATCC13869 |
| Corynebacterium lilium | ATCC15990 |
| Brevibacterium flavum | ATCC14067 |
| Corynebacterium melassecola | ATCC17965 |
| Brevibacterium saccharolyticum | ATCC14066 |
| Brevibacterium immariophilum | ATCC14068 |
| Brevibacterium roseum | ATCC13825 |
| Brevibacterium thiogenitalis | ATCC19240 |
| Microbacterium ammoniaphilum | ATCC15354 |
| Corynebacterium thermoaminogenes | AJ12310(FERM 9246) |

The amino acids to be produced are not particularly limited so far as the genes concerning the biosynthesis and promoters thereof have been elucidated. Examples of effective enzymes concerning the biosynthesis include GDH, citrate synthase (CS), isocitrate dehydrogenase (ICDH), pyruvate dehydrogenase (PDH) and aconitase (ACO) for glutamic acid fermentation.

Enzymes for lysine fermentation including biosynthesis enzymes such as aspartate kinase (AK), dihydrodipicolinate synthase, dihydrodipicolinate reductase, diaminopimelate dehydrogenase and diaminopimelate decarboxylase are also effective. Lysine eccrisis protein (lysE gene) concerning the membrane eccrisis of lysine is also effective.

Effective enzymes for arginine fermentation include N-acetylglutamate synthase, N-acetylglutamate kinase, N-acetylglutamyl phosphate reductase, acetylornithine aminotransferase, N-acetylornithinase, ornithine carbamyltransferase, argininosuccinate synthase, and arginosuccinase. Arginine is formed by the reaction catalyzed by these enzymes. These enzymes are effective. These enzymes are coded by enzymes argA, argB, argC, argD, argE, argF, argG and argH, respectively.

Effective enzymes for serine fermentation includes 3-phosphoglyceric acid dehydrogenase, phosphoserine trans-amylase, phosphoserine phosphatase and the like.

Effective enzymes for phenylalanine fermentation include bio-synthesizing enzymes such as deoxyarabinohepturonic phosphate synthetase, 3-dehydrokinate synthetase, 3-dehydrokinic acid dehydroratase, shikimic acid dehydrogenase, shikimic kinase, 5-enol pyrvilshikimic acid-3-phosphate synthetase, chorismic acid synthetic enzyme, chorismate synthetase, chorismate mutase, prephenate dehydroratase, and the like. Sugar metabolic enzymes such as transketorase, transaidolase, phosphoenolpyrvic acid synthetic enzyme are also effective.

Effective enzymes for tryptophan fermentation include enzymes belonging to tryptophan operon, in addition to various enzymes effective in the above-mentioned phenylalanine fermentation and various enzymes effective in the above-mentioned serine fermentation.

Effective enzymes for proline fermentation include γ-glutamylkinase, γ-glutamylcemialdehyde dehydrogenase, pyrroline-5-carboxylate reductase, in addition to various enzymes effective in the above-mentioned glutamic acid fermentation.

Effective enzymes for glutamine fermentation include glutamine synthetase, in addition to various enzymes effective in the above-mentioned glutamic acid fermentation.

In the inosine production, it is considered to be useful to enhance the expression of 5-phosphoribosyl 1-diphosphate synthetase, 5-phosphoribosyl 1-diphosphate aminotransferase, phosphoribosylaminoimidazole-carboxamide formyltransferase and the like.

In the guanosine production, it is considered to be useful to enhance the expression of 5'-inosinic acid dehydrogenase and 5'-xanthylic acid aminase, addition to 5-phospholibosyl 1-diphosphate synthetase, 5-phospholibosyl 1-diphosphate aminotransferase, phosphoribosylaminoimidazole-carboxamide formyltransferase and the like.

In the adenosine production, it is considered to be useful to enhance the expression of adenirosuccinate synthase, in addition to 5-phosphoribosyl 1-diphosphoric acid synthetic enzyme, 5-phosphoribosyl 1-diphosphoric acid aminotransferase, phosphoribosylaminoimidazole-carboxamide formyltransferase and the like.

In the nucleotide production, it is considered to be useful to enhance the expression of phosphoribosyl transferase, inosine kinase, guanosine kinase and adenosine kinase.

In the present invention, a mutant of a coryneform amino acid-producing bacterium is obtained by, introducing a mutation in a promoter sequence of desired amino acid-biosynthesizing genes on a chromosome of a coryneform amino acid-producing bacterium, such as the above-described promoter sequence for GDH, to make it close to a consensus sequence with a chemical or by introducing the mutation by the genetic recombination to obtain a mutant of the coryneform amino acid-producing microorganism.

The term "consensus sequence" is a sequence which appears most frequently in various promoter sequences. Such consensus sequences include, for example, those of *E. coli* and *Bacillus subtilis*. The consensus sequence of *E. coli* is described in Diane K. Hawley and William R. McClure Nuc. Acid. Res. 11:2237–2255(1983), and that of *B. subtilis* is described in Charles et al. Mol. Gen. Genet 186:339–346 (1982).

The mutation may be caused in either only one promoter sequence such as that for GDH or two or more promoter sequences such as those for GDH, citrate synthase (citrate-synthesizing enzyme) (CS) and isocitrate dehydronenase (isocitrate-synthesizing enzyme) (ICDH).

In the present invention, the mutant thus obtained is cultured to obtain the mutant capable of producing a large amount of an intended amino acid.

It was already elucidated that in the fermentation of glutamic acid, GDH derived from a coryneform glutamate-producing microorganism has its own promoter sequence in upstream region thereof [Sahm et al., Molecular Microbiology (1992), 6, 317–326].

For example, the promoter for GDH of the present invention, GDH gene having the promoter sequence for GDH and L-glutamate-producing *Corynebacterium* strain having this gene can be obtained by, for example, the following methods:

Namely, the strain is subjected to a mutagenesis treatment such as the irradiation with UV, X-rays or radiation, or treatment with a mutagen to obtain a strain resistant to 4-fluoroglutamic acid on an agar plate culture medium containing 4-fluoroglutamic acid. Namely, the mutagenized cells are spread on agar plates culture medium containing 4-fluoroglutamic acid in such a concentration that it inhibits the growth of the parent, and the mutant thus grown is separated.

Further, the promoter sequence of GDH genes can be replaced with variously modified sequences by site directed mutagenesis, and the relationship between the respective sequences and GDH activity is examined so as to select the ones having a high L-glutamate-productivity.

It is particularly preferred in the present invention that the DNA sequence in −35 region of the promoter for GDH-producing gene is at least one DNA sequence selected from the group consisting of CGGTCA, TTGTCA, TTGACA and TTGCCA and/or the DNA sequence in −10 region of the promoter is TATAAT, or the bases of ATAAT in TATTAT promoter sequence in −10 region is replaced with another base, while they do not inhibit the promoter function. The reason why the strain in which the bases of ATAAT in TATAAT sequence in −10 region is replaced with another base and the promoter function is not inhibited can be selected is as follows: Because a remarkable increase in the specific activity of GDH was observed by merely replacing the first "C" of CATAAT with "T" in wild type −10 sequence (refer to p6-4 in Table 1), it was considered that such a replacement with another base is possible.

The promoter sequence of GDH gene is described in, for example, the above-described Sahm et al., Molecular Microbiology (1992), 6, 317–326. It is described therein as Seq ID No. 1. The sequence of GDH gene itself is also described in Sahm et al., Molecular Microbiology (1992), 6, 317–326 to be Seq ID No. 1.

Similarly, the mutation can be introduced in the promoter for citrate-synthesizing enzyme (CS) or isocitrate dehydrogenase (ICDH).

The DNA sequence of icd gene of coryneform bacterium, which codes isocitrate dehydrogenase, has already been elucidated [J. Bacteriol. 177, 774–782 (1995)]. On the bases of this sequence, primers shown in Seq ID No. 14 and Seq ID No. 15 were synthesized. PCR was conducted by using chromosomal DNA of *Brevibacterium lactofermentum* ATCC13869 as the template to amplify about 3 Kbp of DNA fragment containing icd gene and promoter thereof. The amplified fragment thus obtained was completely digested with EcoRI, and mixed with that obtained by complete digestion of pHSG399 (Takara Shuzo Co., Ltd.) with EcoRI to conduct the ligation. After the completion of the ligation, the transformation was conducted using competent cells of *E. coli* JM109. The cells were spread on the L-medium plates containing 10 µg/ml of IPTG, 40 µg/ml of X-Gal and 40 µg/ml of chloramphenicol After overnight incubation, white colonies were taken and the transformants was obtained after single colony isolation.

Thus, the promoters for GDH are those having at least one DNA sequence in −10 region selected from the group consisting of CGGTCA, TTGTCA, TTGACA and TTGCCA in −35 region and/or or TATAAT sequence or the TATAAT sequence but in which the base of ATAAT is replaced with another base, wherein they do not inhibit the promoter function. Genes for producing glutamate dehydrogenase, which have the above-described promoter, are also provided.

The promoters for CS are those having TTGACA sequence in −35 region and/or TATAAT sequence in −10 region, which do not inhibit the promoter function. CS genes having the above-described promoter are also provided.

Promoters for ICDH are those having TTGCCA or TTGACA sequence in the first or the second promoter in −35 region and/or TATAAT sequence in the first or the second promoter in −10 region which do not inhibit the function of the promoter. The icd genes having the above-described promoter are also provided.

Promoters for PDH are those having TTGCCA sequence in −35 region and/or TATAAT sequence in −10 region, which do not inhibit the function of the promoter. PDH genes having the above-described promoter are also provided.

The present invention also provides coryneform L-glutamate-producing bacterium having the above-described genes.

The promoters for algininosuccinate synthase are those having at least one DNA sequence selected from the group consisting of TTGCCA, TTGCCA, and TTGCCA in –35 region and/or TATAAT sequence in –10 region, or the base of ATAAT in TATTAT sequence is replaced with another base, which do not inhibit the function of the promoter. Argininosuccinate synthase genes having the above-described promoter are also provided.

The present invention also provides coryneform arginine-producing bacterium having the above-described genes.

Amino acids can be obtained by culturing a coryneform bacterium of the present invention, which produces an amino acid, preferably L-glutamic acid, in a liquid culture medium to form and thereby to accumulate the intended amino acid, preferably L-glutamic acid, and collecting the amino acid from the culture medium.

The liquid culture medium used for cultivating the above-described strain of the bacterium in the present invention is an ordinary nutrition medium containing carbon sources, nitrogen sources, inorganic salts, growth factors, etc.

The carbon sources include carbohydrates such as glucose, fructose, sucrose, molasses and starch hydrolyzates; alcohols such as ethanol and glycerol; and organic acids such as acetic acid. The nitrogen sources include ammonium sulfate, ammonium nitrate, ammonium chloride, ammonium phosphate, ammonium acetate, ammonia, peptone, meat extract, yeast extract and corn steep liquor. When an auxotrophic mutant is used, the required substances are added to the medium as the reagents or natural substances containing them.

The coryneform bacteria usually produce L-glutamic acid under reduced biotin condition. Therefore, the amount of biotin in the medium is restricted or a substance inhibiting the effect of biotin such as a surfactant or penicillin is added.

The fermentation is preferably conducted by shaking the culture or agitating the culture with aeration while the pH of the culture liquid is kept in the range of 5 to 9 for 2 to 7 days. The pH is preferably controlled with urea, calcium carbonate, gaseous ammonia, ammonia water or the like. The culture temperature is preferably 24 to 37° C.

L-glutamic acid thus produced and accumulated in the culture liquid is collected by an ordinary method such as ion-exchange resin method or crystallization method. Specifically, L-glutamic acid is separated by the adsorption on an anion-exchange resin or by the neutralization crystallization.

According to the present invention, the intended amino acid can be obtained in a high yield by introducing a mutation into a promoter region of amino acid-biosynthesizing genes of a coryneform amino acid-producing bacterium to control the expression of the intended genes. In addition, since any elimination of the intended gene does not occur in the bacteria according to the present invention, contrary to the cases using plasmid, the intended amino acid can be stably obtained in a high yield. Thus, the industrial merit of the invention is great.

The present invention provides various promoters, particularly, promoters for GDH, capable of imparting a power of producing amino acids, particularly glutamic acid, in a high yield to Corynebacterium strains without increasing the amount of by-produced aspartic acid and alanine.

In the present invention, a coryneform L-glutamate-producing bacterium is mutagenized, a strain in which the mutation introduced in a promoter region of GDH gene and which is resistant to 4-fluoroglutamic acid is collected, and the strain is cultured to obtain glutamic acid in a high yield. Thus, the present invention is industrially very advantageous.

The following Examples will further illustrate the present invention.

EXAMPLE 1

Production of Mutant GDH Promoter

A mutant GDH promoter was prepared by site-directed mutagenesis method as follows:

(1) Preparation of GDH Genes having Various Mutant Promoters:

The wild type sequence in –35 region and –10 region of a promoter of GDH gene of a coryneform bacteria is shown in sequence 1. The promoter sequence of wild type has already been reported [Molecular Microbiology (1992), 6, 317–326].

The method of preparing a plasmid carrying GDH gene having a mutant promoter is as follows:

As shown in FIG. 1, a chromosomal gene of a wild type strain of a coryneform bacterium ATCC13869 prepared with "Bacterial Genome DNA purification kit" (Advanced Genetic Technologies Corp.) was used as the template for PCR. The gene amplification was conducted by PCR using upstream and downstream sequences of GDH gene. Both ends were blunt-ended. The product thus obtained was inserted in SmaI site of plasmid pHSG399 (a product of Takara Shuzo Co., Ltd.). Then a replication origin taken from plasmid pSAK4 having the replication origin capable of replicating in a coryneform bacterium was introduced into SaiI site of the plasmid to obtain plasmid pGDH. By this method, GDH genes having each above-described promoter sequence can be obtained by using a primer having each of the sequence of Seq ID No. 1 to Seq ID No. 6 shown in the Sequence Listing as the upstream primer for GDH gene, respectively. It was confirmed by sequencing the PCR amplified fragment that any mutation, other than the introduced mutation in the promoter sequence, did not occur in the amplified fragment. pSAK4 is constructed as follows: previously obtained plasmid pHK4 (J.P. KOKAI No. 5-7491] having an autonomous replication origin derived from plasmid pHM1519 [Agric. Biol. Chem., 48, 2901–1903 (1984)] which is capable of autonomously replicating in Corynebacterium microorganism, is digested with restriction enzymes BamHI and KpnI to obtain a DNA fragment having the replication origin. Then the fragment thus obtained is blunt-ended with DNA-Blunting Kit (Blunting kit of Takara Shuzo Co., Ltd.). After the ligation with SaiI linker, the product thus obtained was inserted into SalI site of pHSG299 (a product of Takara Shuzo Co., Ltd.) to obtain plasmid pSAK4.

(2) Comparison of the Degrees of Expression of GDH having Each Promoter Sequence:

Each plasmid prepared as described above was introduced into wild type strain of coryneform bacterium ATCC13869 by electroporation method (refer to J.P. KOKAI No. 2-207791. For comparing the degrees of expression of GDH for these strains, the specific activity of GDH was determined by the above-described method of Sahm et al. The results are shown in Table 1.

TABLE 1

| Strain | Promoter sequence −35 | −10 | Specific activity of GDH | Relative value |
|---|---|---|---|---|
| ATCC13869 | TGGTCA | CATAAT | 7.7 | 0.1 |
| /pGDH | TGGTCA | CATAAT | 82.7 | 1.0 |
| /p6-2 | CGGTCA | CATAAT | 33.1 | 0.4 |
| /p6-4 | TGGTCA | TATAAT | 225.9 | 2.7 |
| /p6-3 | TTGACA | TATAAT | 327.2 | 4.0 |
| /p6-7 | TTGCCA | TATAAT | 407.0 | 4.9 |
| /p6-8 | TTGTCA | TATAAT | 401.3 | 4.9 |

ATCC 13869/p6-2 through ATCC 13869p6-8/ corresponded to the sequences of Seq ID No. 2 through Seq ID No.6, respectively. These sequences were the same as the sequence No.1 (wild type) except that the underlined parts were changed as follows:

```
No. 1 5'-TTAATTCTTTGTGGTCATATCTGCGACACTGC     CATAATTTGAACGT-3'

2               CGGTCA                         CATAAT

3.              TGGTCA                         TATAAT

4.              TTGACA                         TATAAT

5.              TTGCCA                         TATAAT

6.              TTGTCA                         TATATT
```

These were those of synthetic linear doubled stranded DNA.

EXAMPLE 2

Preparation of Mutant Strains
(1) Preparation of Mutant Strains Resistant to 4-Fluoroglutamic Acid:

AJ13029 is a mutant strain producing glutamic acid and disclosed in WO96/06180. Although it does not produce glutamic acid at a culture temperature of 31.5° C., it produces glutamic acid even in the absence of a biotin-inhibitor when the culture temperature is shifted to 37° C. In this Example, *Brevibacterium lactofermentum* AJ13029 strain was used as the parent strain for preparing the mutant strains. As a matter of course, any of glutamic acid-producing strains other than AJ13029 can be used as a parent strain for preparing mutant strains resistant to 4-fluoroglutamic acid.

AJ13029 were cultured on a CM2B agar medium (Table 2) at 31.5° C. for 24 hours to obtain the bacterial cells. The cells were treated with 250 μg/ml aqueous solution of N-methyl-N'-nitro-N-nitrosoguanidine at 30° C. for 30 minutes. Then a suspension of the cells having a survival rate of 1% was spread on agar plates culture medium (Table 3) containing 4-fluoroglutamic acid (4FG). Colonies were formed after incubating the plate at 31.5° C. for 20 to 30 hours. In this experiment, a slant medium containing 1 mg/ml of 4FG was prepared at first, and then a layer of the same medium without 4FG was formed thereon horizontally. Thus, 4FG concentration gradient was obtained on the surface of the agar medium. When the plate was inoculated with the mutant cells obtained as described, a boundary line was formed at a border of the growing limit of the strain. Bacterial trains which formed colonies in an area containing 4FG of a concentration higher than that of the boundary line were taken. Thus, about 50 strains resistant to 4FG were obtained from about 10,000 mutagenized cells.

TABLE 2

CM2B agar medium

| Ingredient | Concentration |
|---|---|
| Polypeptone (Nippon Seiyaku Co.) | 1.0% |
| Yeast extract (Difco Co.) | 1.0% |
| NaCl | 0.5% |
| d-Biotin | 10 μg/l |
| Agar | 1.5% |

(pH 7.2: adjusted with KOH)

TABLE 3

Agar medium

| Component | Amount in one liter of water |
|---|---|
| Glucose | 10 g |
| $MgSO_4 \cdot 7H_2O$ | 1 g |
| $FeSO_4 \cdot 7H_2O$ | 0.01 g |
| $MnSO_4 \cdot 4-6H_2O$ | 0.01 g |
| Thiamine hydrochloride | 0.2 mg |
| d-Biotin | 0.05 mg |
| $(NH_4)_2SO_4$ | 5 g |
| $Na_2HPO_4 \cdot 12H_2O$ | 7.1 g |
| $KH_2PO_4$ | 1.36 g |
| Agar | 15 g |

(2) Confirmation of Capability of L-Glutamic Acid-Production of 4FG-Resistant Mutant Strains:

The capability of glutamic acid-production of about 50 mutant strains obtained in above (1) and parent AJ13029 strain were confirmed as described below.

AJ13029 and mutant strains were each cultured on CM2B agar medium at 31.5° C. for 20 to 30 hours. A liquid medium having a composition shown as "medium A" in Table 4 was inoculated with the cells thus obtained, and the shaking culture was started at 31.5° C. About 22 hours after, the fresh medium was added so that the final concentration would be that of medium B shown in Table 4. The temperature was shifted to 37° C. and then the culture was continued further for about 24 hours. After the completion of the culture, the culture was examined with a Biotic Analyzer (a product of Asahi Chemical Industry Co., Ltd.) to determine whether L-glutamic acid was produced or not. It was thus found that when the 50 strains were cultured, two strains having a yield of glutamic acid higher than that obtained from the parent strains and a high GDH activity were separated (strain A and strain B). GDH activity of each of them was determined to find that the specific GDH activity of both of them was increased (Table 5). The GDH activity was determined by the method of E. R. Bormann et al. [Molecular Microbiol., 6, 317–326 (1996)]. By sequencing the GDH genes, it was identified that the mutation points were found only in the promoter region of GDH (Table 6).

TABLE 4

| Ingredient | Medium A | Medium B |
|---|---|---|
| Glucose | 3 g/dl | 5 g/dl |
| KH$_2$PO$_4$ | 0.14 g/dl | 0.14 g/dl |
| MgS0$_4$.7H$_2$O | 0.04 g/dl | 0.04 g/dl |
| FeSO$_4$.7H$_2$O | 0.001 g/dl | 0.001 g/dl |
| MnSO$_4$.4H$_2$O | 0.001 g/dl | 0.001 g/dl |
| (NH$_4$)$_2$SO$_4$ | 1.5 g/dl | 2.5 g/dl |
| Soybean protein hydrolyzate solution | 1.5 ml/dl | 0.38 ml/dl |
| Thiamine hydrochloride | 0.2 mg/l | 0.2 mg/l |
| Biotin | 0.3 mg/l | 0.3 mg/l |
| Antifoaming agent | 0.05 ml/l | 0.05 ml/l |
| CaCO$_3$ | 5 gd/l | 5 gd/l |
| pH | 7.0(adjusted with KOH) | |

TABLE 5

Glutamic acid formation and GDH activity of mutant strains

| Strain | Glu (g/dl) | GDH specific activity | Relative value |
|---|---|---|---|
| AJ13029 | 2.6 | 7.7 | 1.0 |
| FGR1 | 2.9 | 23.1 | 3.0 |
| FGR2 | 3.0 | 25.9 | 3.4 |

TABLE 6

DNA sequences in GDH promoter region of mutant strains

| | GDH promoter sequence | | |
|---|---|---|---|
| Strain | −35 | | −10 |
| AJ13029 | TGGTCA | TTCTGTGCGACACTGC | CATAAT |
| FGR1 | TGGTCA | TTCTGTGCGACACTGC | TATAAT |
| FGR2 | TTGTCA | T-CTGTGCGACACTGC | TATAAT |

EXAMPLE 3

Introduction of Mutation into CS Gene Promoter Region of Coryneform Glutamate-Producing Bacterium:

In this Example, a strain having an enhanced promoter for the genes which codes glutamate dehydrogenase (GDH) and citrate-synthesizing enzyme (CS) was produced.

(1) Cloning of gltA Gene:

The sequence of gltA gene of a coryneform bacterium, which codes citrate-synthesizing enzyme, has already been elucidated [Microbial. 140, 1817–1828 (1994)]. On the basis of this sequence, primers shown in Seq ID No. 7 and Seq ID No. 8 were synthesized. On the other hand, chromosomal DNA from *Brevibacterium lactofermentum* ATCC13869 was prepared using Bacterial Genome DNA Purification Kit (Advanced Genetic Technologies Corp.). Sterilized water was added to a mixture of 0.5 μg of the chromosomal DNA, 10 pmol of each of the oligonucleotides, 8 μl of dNTP mixture (2.5 mM each), 5 μl of 10×La Taq Buffer (Takara Shuzo Co., Ltd.) and 2 U of La Taq (Takara Shuzo Co., Ltd.) to obtain 50 μl of PCR reaction cocktail. The reaction cocktail was subjected to PCR. The PCR conditions were 30 cycles of denaturation at 94° C. for 30 seconds, annealing at 55° C. for 15 seconds and extension at 72° C. for 3 seconds using Thermal Cycler TP240 (Takara Shuzo Co., Ltd.) to amplify about 3 Kbp of DNA fragments containing gltA gene and promoter thereof. The amplified fragments thus obtained were purified with SUPRECO2 (Takara Shuzo Co., Ltd.) and then blunt-ended. The blunting was conducted with Blunting Kit of Takara Shuzo Co., Ltd. The blunt-ended fragment was mixed with pHSG399 (Takara Shuzo Co., Ltd.) completely digested with Sinai to conduct the ligation. The ligation reaction was conducted with DNA Ligation Kit ver 2 (Takara Shuzo Co., Ltd.). After the completion of the ligation, the transformation was conducted with competent cells of *E. coli* JM109 (Takara Shuzo Co., Ltd.). The cells were spread on an L medium plates (comprising 10 g/l of bactotryptone, 5 g/l of bactoycast extract, 5 g/l of NaCl and 15 g/l of agar; pH 7.2) containing 10 μg/ml of IPTG (isopropyl-β-D-thiogalactopyranoside), 40 μg/ml of X-Gal (5-bromo-4-chloro-3indoyl-β-D-galactoside) and 40 μg/ml of chloramphenicol. After culturing them overnight, white colonies were taken to obtain the transformed strains after single colony isolation.

Figure 2:
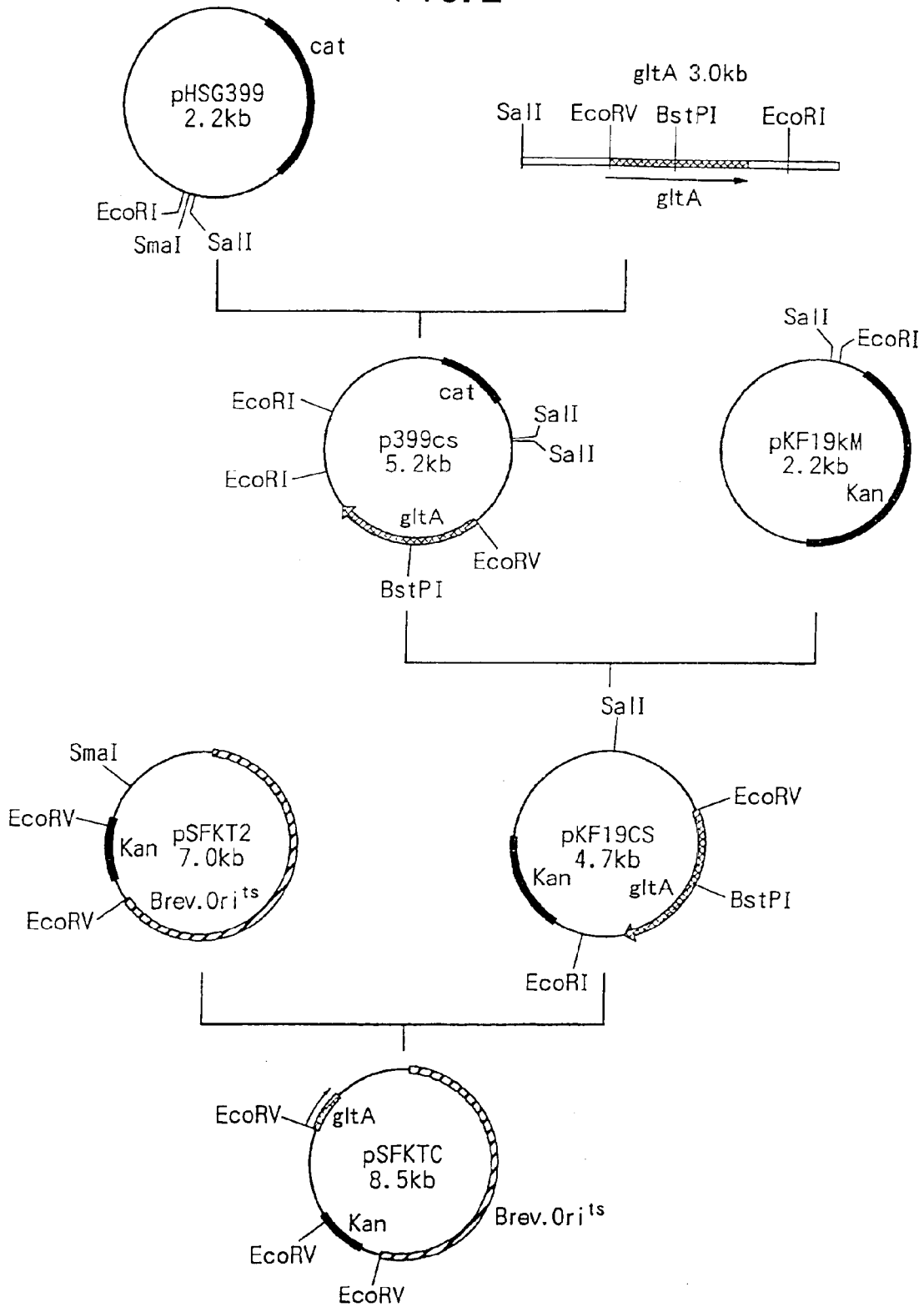
FIG. 2 show a flow of construction of CS gene having a mutant promoter.

From the transformed strains, plasmids were prepared by the alkali method (*Seibutsu Kogaku Jikken-sho* edited by Nippon Seibutsu Kogaku-kai and published by Baifukan, p. 105, 1992). Restriction enzyme maps were prepared, and the plasmid which has the same restriction map as the map shown in FIG. 2 was named "pHSG399CS".

(2) Introduction of Mutations into gltA Promoter:

Mutan-Super Express Km (Takara Shuzo Co., Ltd.) was used for the introduction of mutation into gltA promoter region. The method is specifically described below. PHSG399CS was completely digested with EcoRI and SalI to obtain EcoRI-SalI fragment containing gltA genes, which were ligated to the fragment obtained by complete digestion of pKF19kM (Takara Shuzo Co., Ltd.) with EcoRI and SalI. After the completion of the ligation, the transformation was conducted with competent cells of *E. coli* JM109 (Takara Shuzo Co., Ltd.). The cells were spread on L medium plates containing 10 μg/ml of IPTG, 40 μg/ml of X-Gal and 25 μg/ml of kanamycin. After overnight incubation, white colonies were taken and transformants were obtained by single colony isolation. From the transformants, plasmids were prepared and the plasmid containing gltA gene was named pKF19CS.

PCR was conducted by using pKF19CS as the template and 5'-phosphorylated synthetic DNA shown in sequence of Seq ID No. 9, Seq ID No.10 and Seq ID No.11 together with the selection primer from Mutan super Express Km. The transformation was conducted with competent cells of *E. coli* MV1184 (Takara Shuzo Co., Ltd.) by using the PCR product. The cells were spread on L-medium plates containing 25 μg/ml of kanamycin. After overnight incubation, colonies were taken and the transformants were obtained after single colony isolation. From the transformants, plasmid DNA was prepared. The sequence of gltA promoter region was determined by Sanger method [J. Mol. Biol., 143,161 (1980)] using synthetic DNA having the sequence of Seq ID No. 12. Specifically, the sequence was determined with a Dye Terminator Sequencing Kit (Applied Biosystems) and analyzed by Genetic Analyzer ABI310 (Applied Biosystems). The plasmids in which gltA promoter region was replaced with the sequence shown in Table 7 were named pKF19CS1, pKF19CS2 and pKF19CS4, respectively.

TABLE 7

| | −35 region | −10 region |
|---|---|---|
| pKF19CS | ATGGCT | TATAGC |
| pKF19CS1 | ATGGCT | TATAAC |
| pKF19CS2 | ATGGCT | TATAAT |
| pKF19CS4 | TTGACA | TATAAT |

(3) Construction of Mutant gltA Plasmid:

pKF19CS, pKF19CS1, pKF19CS2 and pKF19CS4 constricted in step (2) were completely digested with SalI and EcoRI (Takara Shuzo Co., Ltd.). On the other hand, plasmid pSFK6 (Japanese Patent Application No. 11-69896) having a replication origin derived from plasmid pAM330 which can autonomously replicate in a coryneform bacterium [Japanese Patent Publication for Opposition Purpose (hereinafter referred to as "J.P. KOKAI") No. 58-67699] was completely digested with EcoRI and SalI. The obtained fragment was ligated with about the 2.5 kb fragment containing gltA. After the completion of the ligation, transformation was conducted with competent cells of E. coli JM109. The cells were spread on the L-medium plates containing 10 μg/ml of IPTG, 40 g/ml of X-Gal and 25 μg/ml of kanamycin. After overnight incubation, colonies were taken and the transformants were obtained after single colony isolation. From the transformants, plasmids were prepared. The plasmids containing gltA gene were named pSFKC, pSFK1, pSFKC2 and pSFKC4, respectively.

(4) Determination of CS Expression from Mutant gltA Plasmid in Coryneform Bacterium:

The plasmid constructed in above step (3) was introduced into *Brevibacterium lactofermentum* ATCC13869. Specifically, this treatment was conducted by electrical pulse method (J.P. KOKAI No. 2-07791). The transformants were selected at 31° C. with CM2B medium plate(comprising 10 g/l of bactotryptone, 10 g/l of bactoyeast extract, 5 g/l of NaCl, 10 μg/l of biotin and 15 g/l of agar; pH 7.0) containing 25 μg/ml of kanamycin. After incubating for two days, colonies were taken and the transformants containing pSFKC, pSFK1, pSFKC2 and pSFKC4 were named BLCS, BLCS1, BLCS2 and BLCS4, respectively, after single colony isolation. A medium having a composition shown in Table 8 was inoculated with the transformant. The culture was continued at 31° C. and terminated before the glucose had been completely consumed. The culture liquid was centrifuged to separate the cells. The cells were washed with 50 mM tris buffer solution (pH 7.5) containing 200 mM of sodium glutamate and then suspended in the same buffer solution. After the sonication with UD-201 (TOMY) followed by the centrifugation (10,000 g), the cells remaining unbroken were removed to obtain a crude enzyme solution. The activity of citrate synthase can be determined according to Methods Enzymol. 13, 3-11 (1969). Specifically, the crude enzyme solution was added to a reaction mixture containing 100 mM of TrisHCl (pH 8), 0.1 mM of DTNB, 200 mM of sodium glutamate and 0.3 mM of acetyl CoA, and the background was determined as the increase in the absorbance at 412 nm at 30° C. determined by Hitachi spectrophotometer U-3210. Further, oxaloacetic acid was added in such an amount that the final concentration thereof would be 0.5 mM. The increase in the absorbance at 412 nm was determined, from which the background value was deducted to determine the activity of the citrate synthase. The protein concentration in the crude enzyme solution was determined by Protein Assay (BIO-RAD). Bovine serum albumin was used as the standard protein. The results are shown in Table 9. It was confirmed that the citrate synthase activity of mutant gltA promoters was increased compared to wild-type gltA.

TABLE 8

| Ingredient | Concentration |
|---|---|
| Glucose | 50 g/l |
| $KH_2PO_4$ | 1 g/l |
| $MnSO_4 \cdot 7H_2O$ | 0.4 mg/l |
| $FeSO_4 \cdot 7H_2O$ | 10 mg/l |
| Soybean protein hydrolysates | 20 ml/l |
| Biotin | 0.5 mg/l |
| Thiamine hydrochloride 2 mg/l | 2 mg/l |

TABLE 9

| Strain | dABS/min/mg | Relative activity | Relative activity |
|---|---|---|---|
| Wild type4 | 6.8 | 1.0 | |
| BLCS00 | 38.8 | 5.7 | 1.0 |
| BLCS01 | 57.1 | 8.4 | 1.21 |
| BLCS02 | 92.5 | 13.6 | 1.9 |
| BLCS04 | 239.5 | 35.2 | 4.8 |

(5) Introduction of Mutant gltA Gene into Temperature-Sensitive Plasmid:

For integrating mutant gltA promoter sequences into a chromosome, a method is known wherein a plasmid of which replication in a coryneform bacterium is temperature sensitive is used (J.P. KOKAI No. 5-7491). PSFKT2 (Japanese Patent Application No.11-81693) was used as the plasmid vector, the replication of which in a coryneform bacterium is temperature sensitive. pKFCS1, pKFCS2 and pKFCS3 completely digested with SalI and BstPI and blunt-ended were used as the mutant gltA promoter sequences. They were ligated to pSFKT2 completely digested with SmaI. After the completion of the ligation, the transformation was conducted with competent cells of E. coli JM109 (Takara Shuzo Co., Ltd.). The cells were spread on the L-medium plates containing 10 μg/ml of IPTG, 40 μg/ml of X-Gal and 25 μg/ml of kanamycin. After overnight incubation, white colonies were taken and the transformants were obtained after single colony isolation. From the transformants, plasmids were prepared. Temperature-sensitive shuttle vectors containing gltA gene were named pSFKTC1, pSFKTC2 and pSFKTC4, respectively.

(6) Introduction of Mutant gltA Promoter into Chromosome:

pSFKTC1, pSFKTC2 and pSFKTC4 were each introduced into Brevibacterium lactofermentum FGR2 strain by electrical pulse method. The transformants were selected on CM2B medium plates containing 25 μg/ml of kanamycin at 25° C. After introduction of each plasmid, each obtained strain was cultured in CM2B liquid medium spread on CM2B plates containing 25 μg/ml of kanamycin, after the dilution to a concentration of $10^3$ to $10^5$ cfu per plate and cultured at 34° C. The strain having the temperature-sensitive plasmid became sensitive to kanamycin because the replication of the plasmid was inhibited at this temperature and, therefore, it could not form colonies. On the other hand, the strain having plasmid DNA integrated into the chromosome could be selected because it formed the colonies. Colonies thus obtained were taken and separated into respective colonies. Chromosomal DNA was extracted from the strain. PCR was conducted by using the chromosomal DNA as the template and primers of sequence shown in Seq ID No. 8 and Seq ID No. 13. About 3 kb of amplified fragments were confirmed. It was thus proved that in this strain, mutant gltA gene derived from the temperature-sensitive plasmid was integrated near gltA gene in the host chromosome by homologous recombination. Strains derived from pSFKTC1, 2 and 4 were named BLCS11, BLCS12 and BLCS14, respectively.

(7) Preparation of Substituted gltA Promoters:

First, kanamycin-sensitive strains were obtained from the strains BLCS11, BLCS 12 and BLCS14 having mutant gltA gene integrated therein by homologous recombination. The strains having plasmid integrated therein were diluted and spread on CMM2B plates and then cultured at 34° C. After the formation of colonies, the replicas of the plates were made using CM2B plates containing 25 µg/ml of kanamycin and were cultured at 34° C. Thus, kanamycin-sensitized strains were obtained.

The chromosome was extracted from the kanamycin sensitive strain, and PCR was conducted with primers having the sequence shown in Seq ID No. 7 and Seq ID No.8 to prepare gltA gene fragments. The amplified fragments thus obtained were purified with SUPRECO2 (Takara shuzo Co., Ltd.) and then subjected to the sequencing reaction using a primer of Seq ID No. 13 to determine the sequence in the promoter region thereof. As a result, the strain having the same promoter sequence as that of pKF19CS1 in Table 7 was named GB01, the strain having the same promoter sequence as that of pKF19CS2 was named GB02 and the strain having the same promoter sequence as that of pKF19CS4 was named GB03. It was indicated that In these strains, the gltA gene of wild type originally located on the chromosome was excised together with the vector plasmid while the mutant gltA gene introduced by the plasmid was remained on the chromosome when the plasmid and duplicated gltA gene were excised from the chromosome.

(8) Determination of Activity of Citrate Synthase of Mutant gltA Promoter Strains:

The activities of the citrate synthase were determined by treating FGR2, GB01, GB02, GB03 and FGR2/pSFKC strains obtained in step (7) in the same manner as that of step (4). The results are shown in Table 10. It was confirmed that the citrate synthase activity of the substituted gltA promoter strain was higher than that of the parent strains thereof.

TABLE 10

| Strain | dABS/min/mg | Relative activity |
| --- | --- | --- |
| FGR2 | 7.9 | 1.0 |
| GB01 | 9.5 | 1.2 |
| GB02 | 15.0 | 1.9 |
| GB03 | 31.6 | 4.0 |
| FGR2/pSFKC | 61.6 | 7.8 |

(9) Results of Culture of Substituted gltA Promoter Strains:

Each of the strains obtained in above-described step (7) was inoculated into a seed culture medium having a composition shown in Table 11, and the culture was shaked at 31.5° C. for 24 hours. 300 ml of a main culture medium having a composition shown in Table 11 was placed into 500 ml glass jar fermenters and then sterilized by heating and was inoculated by 40 ml of the seeds cultured as described above. The culture was started at a culture temperature of 31.5° C. while the stirring rate and the aeration rate were controlled at 800 to 1300 rpm and ½ to ¹⁄₁ vvm, respectively. The pH of the culture liquid was kept at 7.5 with gaseous ammonia. The temperature was shifted to 37° C. 8 hours after the initiation of the culture. The culture was terminated when glucose had been completely consumed in 20 to 40 hours, and the quantity of L-glutamic acid formed and accumulated in the culture liquid was determined.

As a result, the larger improvement in the yield of L-glutamic acid was confirmed when each of the strains GB02 and GB03 rather than GB01 and FGR2/pSFKC was used as shown in Table 12. From these facts, it was found that good results were obtained by introducing the mutation into the gltA promoter to increase the CS activity to 2 to 4 times for the improvement in the yield of glutamic acid produced by those strains.

TABLE 11

| | Concentration | |
| --- | --- | --- |
| Ingredient | Seed culture | Main culture |
| Glucose | 50 g/l | 150 g/l |
| $KH_2PO_4$ | 1 g/l | 2 g/l |
| $MgSO_4 7H_2O$ | 0.4 g/l | 1.5 g/l |
| $FeSO_4 7H_2O$ | 10 mg/l | 15 mg/l |
| $MnSO_4 4H_2O$ | 10 mg/l | 15 mg/l |
| Soybean protein hydrolyzate | 20 ml/l | 50 ml/l |
| Biotin | 0.5 mg/l | 2 mg/l |
| Thiamine hydrochloride | 2 mg/l | 3 mg/l |

TABLE 12

| Strain | L-glutamic acid (g/l) |
| --- | --- |
| FGR2 | 8.9 |
| GB01 | 9.1 |
| GB02 | 9.4 |
| GB03 | 9.4 |
| FGR2/pSFKC | 9.1 |

EXAMPLE 4

Introduction of Mutation into ICDH Gene Promoter Region of Coryneform Glutamate-Producing Bacterium:

In this Example, strains having enhanced promoters for genes which codes glutamate dehydrogenase, citrate synthase and isocitrate dehydrogenase were produced.

(1) Cloning of icd Gene:

The DNA sequence of icd gene of coryneform bacterium, which codes citrate synthase, has already been elucidated [J. Bacteriol. 177, 774–782 (1995)]. On the bases of this sequence, primers shown in Seq ID No. 14 and Seq ID No.15 were synthesized. PCR was conducted by using chromosomal DNA of *Brevibacterium lactofermentum* ATCC13869 as the template to amplify about 3 Kbp of DNA fragment containing icd gene and promoter thereof. The amplified fragment thus obtained was completely digested with EcoRI, and mixed with that obtained by complete digestion of pHSG399 (Takara Shuzo Co., Ltd.) with EcoRI to conduct the ligation. After the completion of the ligation, the transformation was conducted using competent cells of *E. coli* JM109. The cells were spread on the L-medium plates containing 10 µg/ml of IPTG, 40 µg/ml of X-Gal and 40 µg/ml of chloramphenicol After overnight incubation, white colonies were taken and the transformants was obtained after single colony isolation.

The plasmid carrying icd gene was named pHSG399icd.

(2) Introduction of Mutations into icd Promoter:

The accurate location of the promoter of icd gene has not yet been determined. The possibility of increasing mRNA transcription level of icd gene was investigated by artificially modifying the upstream sequence of the gene which codes ICDH into a promoter-like sequence. Specifically, mutations were introduced into the −10 like region existing in the DNA sequence about 190 bp upstream (the first promoter) and about 70 bp (the second promoter) upstream from the first ATG of ICDH protein.

Mutan-Super Express Km (Takara Shuzo Co., Ltd.) was used for the introduction of mutation into an upstream region of icd gene. The method is specifically described below. pHSG399icd was completely digested with PstI to obtain PstI fragment containing the promoter of icd gene. The fragments were ligated with the fragment obtained by complete digestion of pKF18 kM (Takara Shuzo Co., Ltd.) with PstI. After the completion of the ligation, the transformation was conducted with competent cells of E. coli JM109 (Takara Shuzo Co., Ltd.). The cells was spread on the L-medium containing 10 µg/ml of IPTG, 40 µg/ml of X-Gal and 25 µg/ml of kanamycin. After overnight incubation, white colonies were taken and transformants were obtained after single colony isolation. From the transformants, plasmids were prepared, and the plasmid containing the promoter of icd gene was named pKF18icd.

PCR was conducted by using pKF18icd as the template and 5'-phosphorylated synthetic DNA shown in Seq ID No. 16, Seq ID No. 17, Seq ID No. 18, Seq ID No. 19, Seq ID No. 20 and Seq ID No. 21 and the selection primer. These PCR products were used for transforming competent cells of E. coli JM109. The cells were spread on the L-medium plates containing 25 µg/ml of kanamycin. After overnight incubation, formed colonies were taken and the transformants were obtained after single colony isolation. From the transformants, plasmid DNA was prepared, and the sequence of icd promoter region was determined using synthetic DNA shown in Seq ID No. 22 by Sanger's method [J. Mol. Biol., 143, 161 (1980)]. Specifically, the DNA sequence was determined with Dye Terminator Sequencing Kit (Applied Biosystems), and analyzed with Genetic Analyzer AB1310 (Applied Biosystems). Those obtained by replacing icd promoter region with a sequence shown in Table 7 were named pKF18ICD1, pKF18ICD2, pKF18ICD3, pKF18ICD4, pKF18ICD5 and pKF18ICD6m respectively. Among them, pKF18ICD2 was completely digested with PstI to obtain PstI fragment containing the promoter of icd gene. The fragment was ligated with the fragment obtained by complete PstI digestion of pKF18 kM (Takara Shuzo Co., Ltd.). After the completion of the ligation, the transformation was conducted with competent cells of E. coli JM109 (Takara Shuzo Co., Ltd.). The cells were spread on the L-medium plates containing 10 µg/ml of IPTG, 40 µg/ml of X-Gal and 25 µg/ml of kanamycin. After overnight incubation, white colonies were taken and the transformed strains were obtained after single colony isolation. From the transformed strains, plasmids were prepared, and the plasmid containing the promoter of icd gene was named pKF18ICDM2. PCR was conducted using pKF18ICDM2 as the template and 5'-phosphorylated synthetic DNA shown in Seq ID No. 20 and Seq ID No. 21 and the selection primer. The transformation of competent cells of E. coli JM109 was conducted with the PCR product. The cells were spread on the L-medium plates containing 25 µg/ml of kanamycin. After overnight incubation, colonies thus formed were taken and transformants were obtained after single colony isolation. From the transformants, plasmids DNA were prepared, and the sequence of icd promoter region was determined using synthetic DNA shown in Seq ID No. 22. Those obtained by replacing icd promoter region with the sequence shown in Table 13 were named pKF18ICD25 and pKF18ICD26, respectively.

TABLE 13

| Plasmid | 1st Promoter | | 2nd Promoter | |
| --- | --- | --- | --- | --- |
| | −35 | −10 | −35 | −10 |
| pKF18ICD | GCGACT | GAAAGT | TTTCCA | CACCAT |
| pKF18ICD01 | GCGACT | TATAAT | TTTCCA | CACCAT |
| pKF18ICD02 | TTGACA | TATAAT | TTTCCA | CACCAT |
| pKF18ICD03 | TTGACT | TAAAGT | TTTCCA | CACCAT |
| pKF18ICD04 | GCGACT | GAAAGT | TTTCCA | TATAAT |
| pKF18ICD05 | GCGACT | GAAAGT | TTGCCA | TATAAT |
| pKF18ICD06 | GCGACT | GAAAGT | TTGACA | TATAAT |
| pKF18ICD25 | TTGACA | TATAAT | TTGCCA | TATAAT |
| pKF18ICD26 | TTGACA | TATAAT | TTGACA | TATAAT |

Figure 3:
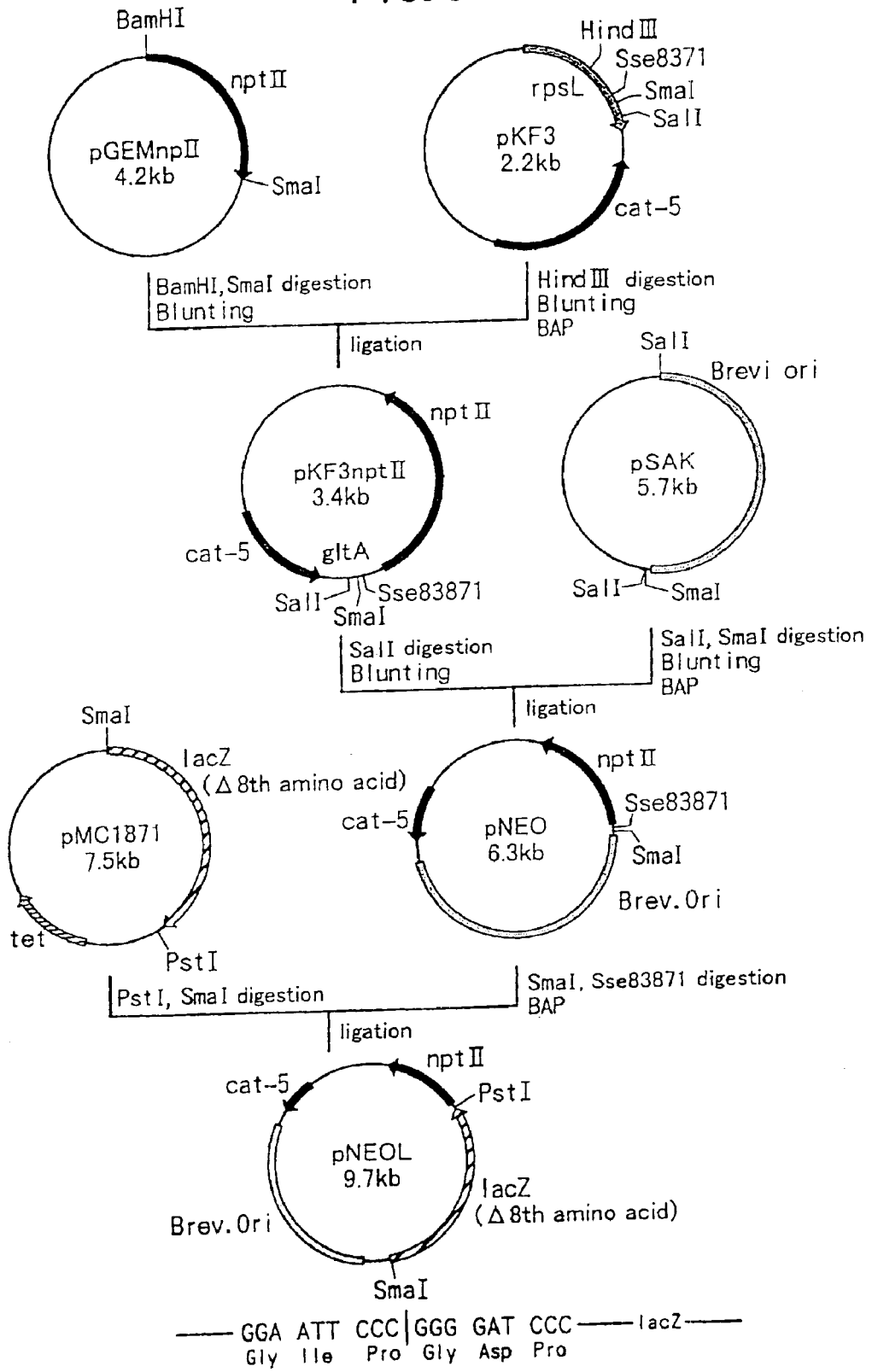
FIG. 3 show a flow of construction of shuttle vector carrying lacZ as a reporter gene.

(3) Plasmid Construction for Determination of Promoter Activity:

For easily determining the promoter activity, a possible method is the indirect determination of the promoter activity using a reporter gene. Desirable properties required of the reporter gene are that the activity can be easily determined, that even when an amino acid is added to an N-terminal, the activity is not seriously lowered, that the background reaction does not occur and that it has a restriction enzyme cleavage site suitable for the gene manipulation. Because β galactosidase (LacZ) of E. coli is widely used as a reporter gene and bacteria of the genus Corynebacterium do not have lactose assimilability [J. Gen. Appl. Microbiol., 18, 399–416 (1972)], LacZ was determined to be the optimum reporter gene. Then, plasmid pNEOL carrying LacZ as the reporter gene was constructed (see FIG. 3). The process for the construction is described in detail below. PCR was conducted by using a chromosomal DNA obtained from E coli ME8459(ME8459 was deposited with National Institute of Genetics (Japan)) as the template with synthetic DNA shown in Seq ID No. 23 and Seq ID No.24 as the primer. The PCR product was completely digested with SmaI and BamHI and then ligated with fragments obtained by digesting pKF3 (Takara Shuzo Co., Ltd.) with HindIII and blunt-ended. After the completion of the ligation, the transformation was conducted with competent cells of E. coli JM109 (Takara Shuzo Co., Ltd.). The cells were spread on the L-medium plates containing 25 µg/ml of kanamycin. After overnight incubation, colonies thus formed were taken and separated into respective colonies to obtain the transformed strain. The plasmid obtained from the transformed strain was named pKF3nptII. Then, this plasmid was digested with SalI. On the other hand, pSAK4 described in Example 1(1) was completely digested with SmaI and SalI and blunt-ended. These fragments were ligated together to construct a shuttle vector pNEO which can replicate in a coryneform bacterium. This plasmid was capable of imparting a resistance to chloramphenicol and resistance to kanamycin to the hosts. Further, pNEO was completely digested with SmaI and Sse8387I. The resultant fragments were ligated to those obtained by complete digestion of pMC1871 (Farmacia Biotech.) with PstI and SmaI. Thus, shuttle vector pNEOL which can be replicated in a coryneform bacterium and having LacZ lacking 8 amino acid on N-terminal as the reporter gene was constructed (see FIG. 3).

(4) Determination of Activity of Mutant icd Promoter:

Plasmids having mutant icd promoter constructed in above-described step (2), i.e. pKF18ICD1, pKF18ICD2, pKF18ICD3, pKF18ICD4, pKF18ICD5, pKF18ICD6, pKF18ICD25, pKF18ICD26 and pKF18ICD, were completely digested with SacII and PstI and then blunt-ended. They were ligated with fragment obtained by digesting pNEOL with SmaI. After the completion of the ligation, the transformation was conducted with competent cells of *E. coli* JM109. The cells were spread on the L-medium plates containing IPTG, X-Gal and 40 µg/ml of chloramphenicol. After overnight incubation, blue colonies were taken and the transformed strains were obtained after single colony isolation.

From the transformed strains, plasmids were prepared. Plasmids having a structure capable of producing a fused protein of ICDH and LacZ were named pNEOICD1, pNEOICD2, pNEOICD3, pNEOICD4, pNEOICD5, pNEOICD6, pNEOICD25, pNEOICD26 and pNEOLICD, respectively. Each of These plasmids or pNEOL was introduced into *Brevibacterium lactofermentum* ATCC13869 by electrical pulse method. The transformants were selected by using CM2B medium plates (comprising 10 g/l of bactotryptone,10 g/l of bactoyeast extract, 5 g/l of NaCl, 10 µg/l of biotin and 15 g/l of agar and having pH 7.0) containing 25 µg/ml of kanamycin and 40 µg/ml of X-Gal at 31° C. for two days. After the completion of the introduction, colonies thus formed were taken and isolated as single colonies. The transformants containing pNEOICD1, pNEOICD2, pNEOICD3, pNEOICD4, pNEOICD5, pNEOICD6, pNEOICD25, pNEOICD26 and pNEOLICD were named BLAC1, BLAC2, BLAC3, BLAC4, BLAC5, BLAC6, BLAC25, BLAC26, BLAC and BNEOL, respectively. All the transformants other than BNEO formed blue colonies. Crude enzyme solutions were prepared from the transformants in the same manner as that of step (4) in Example 3 except that "Z-Buffer" (comprising 10 mM of KCl, 1 mM of MgSO$_4$, 270 µg/100 mM of 2-ME and NaPi and having pH 7.5) was used as a washing and suspension buffer. The activity of LacZ was determined as follows: Z-Buffer was mixed with the crude enzyme solution, ONPG in Z-Buffer having the final concentration of 0.8 mg/ml was added to the resultant mixture, and the increase in the absorbance at 420 nm at 30° C. was determined with Hitachi spectrophotometer U-3210 as the activity of LacZ. The protein concentration in the crude enzyme solution was determined by Protein Assay (BIO-RAD). Bovine serum albumin was used as the standard protein. The results are shown in Table 14. It was confirmed that the LacZ activity of the strain having a mutation in icd promoter and expressing ICDH-LacZ fused protein was higher than that expressing the wild type ICDH-LacZ fused protein.

TABLE 14

| Strain | dABS/min/mg | Relative activity |
| --- | --- | --- |
| BNEOL | Not Detected | 0.0 |
| BNEOLI | 42 | 1.0 |
| BNEOLI-1 | 84 | 2.0 |
| BNEOLI-2 | 168 | 4.0 |
| BNEOLI-3 | 80 | 1.9 |
| BNEOLI-4 | 126 | 3.0 |
| BNEOLI-5 | 139 | 3.3 |
| BNEOLI-6 | 84 | 2.0 |
| BNEOLI-25 | 168 | 4.0 |
| BNEOLI-26 | 170 | 4.0 |

(5) Introduction of Mutant icd Gene into Temperature-Sensitive Plasmid:

Plasmid vector pSFKT2 (Japanese Patent Application No. 11-81693) the replication of which in a coryneform bacterium was temperature-sensitive was used. pKF18ICD1, pKF18ICD2, pKF18ICD3, pKF18ICD4, pKF18ICD5, pKF18ICD6, pKFICD25 and pKFICD26 were completely digested with PstI and the amplified fragments were used as the mutant icd promoter sequences. The fragments thus obtained were ligated with pSFKT2 completely digested with PstI. After the completion of the ligation, the transformation was conducted with competent cells of *E. coli* JM109 (Takara Shuzo Co., Ltd.). The cells were spread on the L-medium plates containing 10 µg/ml of IPTG, 40 µg/ml of X-Gal and 25 µg/ml of kanamycin. After overnight incubation, white colonies were taken and transformed strains were obtained after single colony isolation. From the transformed strains, plasmids were prepared. Temperature-sensitive shuttle vectors containing icd promoter were named pSFKT11, pSFKT12, pSFKT13, pSFKT14, pSFKT15, pSFKT16, pSFKT25 and pSFKT26, respectively.

(6) Integration of Mutant icd Promoter into Chromosome:

The plasmids constructed in above-described step (5) were each introduced into Brevibacterium lactofermentum GB02 strain by electrical pulse method. The transformants were selected with CM2B medium plates(comprising 10 g/l of bactotryptone, 10 g/l of bactoyeast extract, 5 g/l of NaCl, 10 µg/l of biotin and 15 g/l of agar and having pH 7.0) containing 25 µg/ml of kanamycin at 25° C. After the completion of the introduction, the obtained strains were cultured in CM2B liquid medium, spread on CM2B plates containing 25 µg/ml of kanamycin after the dilution to a concentration of 10$^3$ to 10$^5$ cfu per plate and cultured at 34° C. The strain having the temperature-sensitive plasmid became sensitive to kanamycin because the replication of the plasmid was inhibited at this temperature and, therefore, it could not form colonies. On the other hand, the strain having plasmid DNA integrated into the chromosome could be selected because it could form colonies. Colonies thus obtained were taken and separated into isolated colonies. Chromosomal DNA was extracted from the strain and PCR was conducted by using the chromosomal DNA as the template with primers shown in Seq ID No. 13 and Seq ID No. 15. About 3 kb of amplified fragments were confirmed. It was thus proved that in this strain, mutant icd gene derived from the temperature-sensitive plasmid was integrated near icd gene in the host chromosome by homologous recombination.

(7) Preparation of Strains having Substituted icd Promoter:

First, kanamycin-sensitive strain was obtained from the strains having mutant icd gene integrated therein by the homologous recombination as described in step (6). The strains having the plasmid integrated therein were diluted and spread on CM2B plates and then cultured at 34° C. After the formation of colonies, replicas were made on CM2B plates containing 25 µg/ml of kanamycin, and they were incubated at 34° C. Thus, kanamycin-sensitive strains were obtained.

The chromosome was extracted from the kanamycin resistant strain, and PCR was conducted using primers shown in Seq ID No.14 and Seq ID No.15 to prepare icd gene fragments. The amplified fragments thus obtained were purified with SUPRECO2 (Takara shuzo Co., Ltd.) and then subjected to the sequencing reaction using a primer shown in Seq ID No. 22 to determine the sequence of the promoter region thereof. As a result, strains having icd promoter sequences derived from pSFKTI1, pSFKTI2, pSFKTI3, pSFKTI4, pSFKTI5, pSFKTI6, pSFKTI25 and pSFKTI26 were named GC01, GC02, GC03, GC04, GC05, GC06, GC25 and GC26, respectively. In these strains, when the plasmid and duplicate icd gene were excised from the chromosome, the icd gene of wild type originally located on the chromosome was excised together with the vector plasmid, while the mutant icd gene introduced by the plasmid remained on the chromosome.

(8) Determination of Isocitrate-Dehydrogenase Activity of the Mutant Strains having Mutant icd Promoter:

ICDH crude enzyme solution was prepared by using each of the 8 strains obtained in above-described step (7) and GB02 strain in the same manner as that of step (7) in Example 3. The ICDH activities were determined as follows: The crude enzyme solution was added to a reaction solution containing 35 mM of Tris-HCl (pH 7.5), 1.5 mM of $MnSO_4$, 0.1. mM of NADP and 1.3 mM of isocitric acid, and the increase in the absorbance at 340 nm at 30° C. was determined with Hitachi spectrophotometer U-3210 as the activity of ICDH. The protein concentration in the crude enzyme solution was determined by Protein Assay (BIO-RAD). Bovine serum albumin was used as the standard protein. The results are shown in Table 15. It was confirmed that the isocitrate dehydrogenase activity of substituted icd promoter strains was higher than that of the parent strain.

TABLE 15

| Strain | dABS/min/mg | Relative activity |
|---|---|---|
| GB02 | 3.9 | 1.0 |
| GC01 | 8.2 | 2.1 |
| GC02 | 19.1 | 4.9 |
| GC03 | 7.0 | 1.8 |
| GC04 | 12.5 | 3.2 |
| GC05 | 19.1 | 4.9 |
| GC06 | 10.5 | 2.7 |
| GC25 | 30.4 | 7.8 |
| GC26 | 24.2 | 6.2 |

(9) Results of Culturing the Strains Containing Substituted icd Promoter:

Each of the 8 strains obtained in above-described step (7) was cultured in the same manner as that in step (9) in Example 3. As a result, the improvement in the yield of L-glutamic acid was confirmed when any one of the strains GC02, GC04, GC05, GC25 and GC26 was used as shown in Table 16. It was found that good results were obtained by introducing the mutation into icd promoter to increase the ICDH activity to at least 3 times.

TABLE 16

| Strain | L-glutamic acid (g/dl) |
|---|---|
| GB02 | 9.2 |
| GC01 | 9.0 |
| GC02 | 9.5 |
| GC03 | 9.1 |
| GC04 | 9.4 |
| GC05 | 9.6 |
| GC06 | 9.2 |
| GC25 | 9.9 |
| GC26 | 9.8 |

EXAMPLE 5

Introduction of Mutation into PDH Gene Promoter Region of Coryneform Glutamate-Producing Bacterium (1) Cloning of pdhA Gene from Coryneform Bacteria Primers shown in Seq ID No. 25 and Seq ID No. 26 were synthesized by selecting regions having a high homology among EI subunits of pyruvate dehydrogenase (PDH) of *Escherichia coli, Pseudomonas aeruginosa* and *Mycobacterium tuberculosis*. PCR was conducted by using chromosome of *Brevibacterium lactofermentum* ATCC13869, prepared with a bacterial genomic DNA purification kit (Advanced Genetic Technologies Corp.), as the template under standard reaction conditions described on page 8 of PCR Technology (edited by H. Erlich and published by Stockton Press, 1989). The reaction solution was subjected to the electrophoresis in an agarose gel to find that about 1.3 kilobases of DNA fragment was amplified. The sequence of both end of the obtained DNA was determined with synthetic DNA shown in Seq ID No. 25 and Seq ID No. 26. The sequence was determined by Sanger's method [J. Mol. Biol., 143, 161 (1980)] with DNA Sequencing Kit (Applied Biosystems Co.). The determined sequence was deduced to amino acids, and compared with E1 subunits of pyruvate dehydrogenase derived from each of *Escherichia coli, Pseudomonas aeruginosa* and *Mycobacterium tuberculosis* to find a high homology among them. Consequently, it was determined that the DNA fragment amplified by PCR was a part of pdhA gene which codes EI subunit of pyruvate dehydrogenase of *Brevibacterium lactofermentum* ATCC13869. The cloning of the upstream and downstream region of the gene was conducted. The cloning method was as follows: A chromosome of *Brevibacterium lactofermentum* ATCC13869 was digested with restriction enzymes EcoRI, BamHI, Hind III, Pst I, Sal I and Xba I (Takara Shuzo Co., ltd.) to obtain DNA fragments. LA PCR in vitro cloning Kit (Takara Shuzo Co., Ltd.) was used for the cloning, using the sequences shown in Seq ID No. 27 and Seq ID No. 28 in the Sequence Listing as primers for cloning the upstream region, and sequences shown in Seq ID No. 29 and Seq ID No. 30 as primers for cloning the downstream region. After PCR using the kit, DNA fragments of about 0.5, 2.5, 3.0, 1.5 and 1.8 kilobases were amplified for the upstream region from the fragments obtained by digestion with EcoRI, Hind III, Pst I, Sal I and Xba I, respectively; and DNA fragments of about 1.5, 3.5 and 1.0 kilobase were amplified for the downstream region from the fragments obtained by digestion with BamHI, Hind III and Pst I, respectively. The sequences of these DNA fragments were determined in the same manner as that described above. It was found that the amplified DNA fragments further contained an open reading frame of about 920 amino acids and also that a region supposed to be a promoter region was present in the upstream region. Because the deduced amino acid sequence from the DNA sequence of the open reading frame is highly homologous to known EI subunit of pyruvate dehydrogenase such as that of *E. coli*, it was apparent that the open reading frame was the pdhA gene which codes El subunit of pyruvate dehydrogenase of *Brevibacterium lactofermentum* ATCC13869. The DNA sequence of the open reading frame was shown in Seq ID No. 31 in the Sequence Listing. In Seq ID No. 31 in the Sequence Listing, deduced amino acid sequence from the DNA sequence is also shown. Since methionine residue at N-terminal of the protein is derived from ATG which is an initiation codon, it usually does not concern the essential function of protein, and it is well known that the methionine residue is removed by the effect of peptidase after the translation. Therefore, in the above-described protein, it is possible that methionine residue at the N-terminal has been removed. However, the GTG sequence is present in 6 bases upstream of ATG shown in Seq ID No. 31 in the Sequence Listing, and it is also possible that amino acids is translated from this point. Pyruvate dehydrogenases of other microorganisms such as *E. coli* are composed of three subunits of E1, E2 and E3, and genes which encode them constitute an operon in many cases. However, there was no open reading frame considered to be E2 and E3 subunit of pyruvate dehydrogenase in about 3 kilobases downstream of pdhA gene. Instead, it was shown that a sequence supposed to be a terminator was present in the downstream of the open reading frame. From these facts, it was supposed that E2 and E3 subunits of pyruvate dehydrogenase of *Brevibacterium lactofermentum* ATCC13869 were present in another region on the chromosome.

(2) Construction of a Plasmid for Amplifying pdhA:

It was already apparent that a strain obtained by introducing a gene which codes three subunits constituting PDH of *E. coli* into *Brevibacterium lactofermentum* ATCC13869 gives an improved glutamic acid yield (JP No.10-360619). However, in PDH of *Brevibacterium lactofermentum* ATCC13869, only pdhA gene which codes EI subunit had been cloned, and no examination had not been made to know whether the amplification of the gene alone is effective in improving the yield of glutamic acid. Under these circumstances, examination was made to know whether the amplification of pdhA gene alone is effective in improving the yield of glutamic acid or not.

Primers shown in Seq ID No. 35 and Seq ID No. 36 were synthesized on the basis of the previously cloned DNA sequences. PCR was conducted by using chromosome of *Brevibacterium lactofermentum* ATCC13869, prepared with a Bacterial Genomic DNA Purification kit (Advanced Genetic Technologies Corp.), as the template under standard reaction conditions described on page 8 of PCR Technology (edited by H. Erlich and published by Stockton Press, 1989) to amplify pdhA gene. Among the primers thus synthesized, Seq ID No. 35 corresponded to a sequence of base No. 1397 to No.1416 in pdhA gene described in Seq ID No. 33 in the Sequence Listing. Seq ID No. 36 was the complementary strand of the DNA sequence corresponding to the sequence of base No. 5355 to No.5374 in Seq ID No. 33 in the Sequence Listing, which was represented from the 5' side.

PCR product thus obtained was purified by an ordinary method and reacted with restriction enzyme Sal I and EcoT22I. The fragment was ligated with pSFK(Patent Application No.11-69896), cleaved with restriction enzymes Sal I and Pst I, with a ligation kit (Takara Shuzo Co., Ltd.). After the transformation with competent cells (Takara Shuzo Co., Ltd.) of *E. coli* JM109, the cells were spread to the L-medium medium plates(comprising 10 g/l of bactotryptone, 5 g/l of bactoyeast extract, 5 g/l of NaCl and 15 g/l of agar and having pH 7.2) containing 10 µg/ml of IPTG (isopropyl-β-D-thiogalactopyranoside), 40 µg/ml of X-Gal (5-bromo-4-chloro-3-indolyl-β-D-galactoside) and 25 µg/ml of kanamycin. After overnight incubation, white colonies were taken and the transformed strains were obtained after single colony isolation.

From the transformed strains, plasmids were prepared by alkali method (*Seibutsu Kogaku Jikken-sho* edited by Nippon Seibutsu Kogaku kai and published by Baifukan, p. 105, 1992). Restriction enzyme maps of DNA fragments inserted into the vectors were prepared and compared with the restriction enzyme map of pdhA gene reported in sequence No. 33 of the Sequence Listing. A plasmid containing DNA fragments inserted therein having the same restriction enzyme map as that of pdhA gene was named pSFKBPDHA.

(3) Introduction of pASFKBPDHA into *Brevibacterium lactofermentum* ATCC13869 and GC25 and Evaluation of the Fermentation Experiments:

*Brevibacterium lactofermentum* ATCC13869 and GC25 were transformed with plasmid pSFKBPDHA by electrical pulse method (J.P. KOKAI No. 2-207791) to obtain the transformed strains. The culture for producing L-glutamic acid was conducted with transformed strain ATCC13869/pSFKBPDHA and GC25/pSFKBPDHA obtained by introducing plasmid pSFKBPDHA into *Brevibacterium lactofermentum* ATCC13869 and GC25 as follows: Cells of ATCC13869/pSFKBPDHA and GC25/pSFKBPDHA obtained by the culture on CM2B medium plates containing 25 µg/ml of kanamycin were inoculated into a medium (comprising 1 liter of pure water containing 80 g of glucose, 1 g of $KH_2PO_4$, 0.4 g of $MgSO_4 \cdot 7H_2$, 30 g of $(NH_4)_2SO_4$, 0.01 g of $FeSO_4 \cdot 7H_2O$, 0.01 g of $MnSO_4 \cdot 7H_2O$, 15 ml of soybean protein hydrolyzate, 200 µg of thiamine hydrochloride, 60 µg of biotin, 25 mg of kanamycin and 50 g of $CaCO_3$; and having a pH adjusted to 8.0 with KOH). Then the culture was shaken at 31.5° C. until sugar in the medium had been consumed. The obtained products were inoculated into the medium of the same composition as that described above (for GC25/pSFK6 and GC25/pSFKBDHA) or the medium eliminated Biotin from the composition as that described above (for ATCC13869/pSFK6 and ATCC13869/pSFKBPDHA) in an amount of 5%, and the shaking culture was conducted at 37° C. until sugar in the medium had been consumed. As a control, strains obtained by transforming *Brevibacterium lactofermentum* ATCC13869 and GC25 with previously obtained plasmid pSFK6 capable of autonomously replicating in coryneform bacterium by electrical pulse method (J.P. KOKAI No. 2-207791), were cultured in the same manner as that described above. After the completion of the culture, the amount of L-glutamic acid accumulated in the culture medium was determined with Biotic Analyzer AS-210 (a product of Asahi Chemical Industry Co., Ltd.). The results are shown in Table 17.

TABLE 17

| Strain | Yield of L-glutamic acid (g/dl) |
|---|---|
| ATCC13869/Psfk | 3.6 |
| ATCC13869/pSFKBPDHA | 3.8 |
| GC25/pSFK6 | 5.1 |
| GC25/pSFKBPDHA | 5.3 |

From these results, it was apparent that even the amplification of pdhA gene alone is sufficiently effective in improving the yield of Glu in *Brevibacterium lactofermentum* ATCC13869 and GC25.

(4) Construction of Plasmids for Determination of the Activity of Mutated pdhA Promoter:

To produce promoter mutant of pyruvate dehydrogenase (PDH), the determination of the previously cloned promoter region of pdhA gene of *Brevibacterium lactofermentum* ATCC13869 was conducted and also the determination of difference in the expression caused by the modification of the promoter region were conducted by determining the activity of β-galactosidase.

The promoter region of pdhA gene was presumed from the DNA sequence which had been already elucidated by cloning. As a result, it was supposed to be possible that base No. 2252 to No. 2257 and No. 2279 to No. 2284 in Seq ID No. 33 in the Sequence Listing were −35 region and −10 region, respectively. Therefore, primers shown as Seq ID No. 37 and Seq ID No. 38 in the Sequence Listing were synthesized, and DNA fragments containing promoter region of pdhA gene were amplified by PCR method by using chromosomal DNA of *Brevibacterium lactofermentum* ATCC13869 as a template. Among the synthesized primers, Seq ID No. 37 corresponded to the sequence ranging from base No. 2194 to base No. 2221 in Seq ID No. 33; but the base No. 2198 had been replaced with C, and the base No. 2200 and No. 2202 had been replaced with G, and recognition sequence for restriction enzyme SmaI had been inserted. Seq ID No. 38 corresponded to the sequence ranging from base No. 2372 to base No. 2398 in Seq ID No. 33; but base No. 2393 and No. 2394 had been replaced with G, and the complementary strand of the DNA sequence having a recognition sequence of restriction enzyme SmaI inserted therein was represented from the 5'-end. PCR was conducted by using chromosome of *Brevibacterium lactofermentum* ATCC13869, prepared with Bacterial Genomic DNA Purification kit (Advanced Genetic Technologies Corp.), as the template under standard reaction conditions described on page 8 of PCR Technology (edited by H. Erlich and published by Stockton Press, 1989) to amplify the promoter region of pdhA gene. PCR product thus obtained was purified by an ordinary method and reacted with restriction enzyme Sma I. The fragments were ligated with pNEOL lacking in promoter region of lacZ gene which could be replicate in a coryneform bacterium and which had been digested with restriction enzymes Sma I, (Example 4 (3) with a Ligation Kit (Takara Shuzo Co., Ltd.). After the transformation with competent cells (Takara Shuzo Co., Ltd.) of *E. coli* JM109, the cells were spread on the L-medium plates(comprising 10 g/l of bactotryptone, 5 g/l of bactoyeast extract, 5 g/l of NaCl and 15 g/l of agar and having pH 7.2) containing 40 µg/ml of X-Gal (5-bromo-4-chloro-3-indolyl-β-D-galactoside) and 25 µg/ml of kanamycin. After overnight incubation, blue colonies were taken and the transformed strains were obtained after single colony isolation. From the transformants, plasmids were prepared by alkali method (*Seibutsu Kogaku Jikken-sho* edited by Nippon Seibutsu Kogaku-kai and published by Baifukan, p. 105, 1992) After sequencing DNA fragments inserted into the vector by an ordinary method, the plasmid containing the DNA fragment inserted therein was named pNEOLBPDHApro1.

Further, primers indicated as Seq ID No. 39, Seq ID No. 40 and Seq ID NO. 41 in the Sequence Listing were synthesized for constructing plasmids wherein a region supposed to be the promoter site was changed to the consensus sequence of promoters of coryneform bacteria. By using each of the primers and a primer shown in Seq ID No. 38, DNA fragments wherein the promoter region of pdhA gene was changed to the consensus sequence were amplified by PCR method by using chromosomal DNA of Brevibacterium lactofermentum ATCC13869 as a template. Among the synthesized primers, Seq ID No. 39 corresponded to the sequence ranging from base No. 2244 to base No. 2273 in Seq ID No. 33; base No. 2255 had been replaced with C, and base No. 2257 had been replaced with A; thus only –35 region had been changed to the consensus sequence of the coryneform bacteria. Seq ID No. 40 corresponded to the sequence ranging from base No. 2249 to base No. 2288 in sequence No. 33; base No. 2279 and No. 2281 had been replaced with T; thus only –10 region had been changed to the consensus sequence of the coryneform bacteria. Sequence No. 41 corresponded to the sequence ranging from base No. 2249 to base No. 2288 in Seq ID No. 33; base No. 2255 had been replaced with C, base No. 2257 had been replaced with A, and base No. 2279 and No. 2281 had been replaced with T; thus both. –35 region and –10 region had been changed to the consensus sequence of the coryneform bacteria. PCR was conducted by using chromosome of *Brevibacterium lactofermentum* ATCC13869, prepared with a Bacterial Genomic DNA Purification Kit (Advanced. Genetic Technologies Corp.), as the template under standard reaction conditions described on page 8 of PCR Technology (edited by H. Erlich and published by Stockton Press, 1989) to amplify the promoter region of pdhA gene with these primers so that the promoter region was changed to the consensus sequence. PCR products thus obtained were purified by an ordinary method and reacted with restriction enzyme SmaI. The fragments were ligated with pNEOL lacking the promoter region of IacZ gene, which could replicate in a coryneform bacterium and which had been cleaved with restriction enzymes Sma I, with a Ligation Kit (Takara Shuzo Co., Ltd.). After the transformation with competent cells (Takara Shuzo Co., Ltd.) of *E. coli* JM109, the cells were spread on the L-medium plates (comprising 10 g/l of bactotryptone, 5 g/l of bactoyeast extract, 5 g/l of NaCl and 15 g/l of agar and having pH 7.2) containing 40 µg/ml of X-Gal (5-bromo-4-chloro-3-indolyl-β-D-galactoside) and 25 µg/ml of kanamycin. After overnight incubation, blue colonies were taken and the transformed strains were obtained after single colony isolation. From the transformed strains, plasmids were prepared by the alkali method (*Seibutsu Kogaku Jikken-sho* edited by Nippon Seibutsu Kogaku kai and published by Baifukan, p. 105, 1992). After sequencing DNA fragments inserted into the vector by an ordinary method, the plasmid containing DNA fragments, wherein only the sequence in –35 region had been changed to the consensus sequence, inserted therein was named pNEOLBPDHApro35; the plasmid containing DNA fragments, wherein only the sequence in –10 region had been changed to the consensus sequence, was inserted therein was named pNEOLBPDHApro10; and the plasmid containing DNA fragments, wherein the sequences in both –35 region and –10 region had been changed to the consensus sequence, was inserted therein was named pNEOLBPDHApro3510.

(5) The Evaluation of the Mutated pdhA Promoter Activity:

First, GC25 was transformed with plasmid pSFKTPDHApro3510 for preparing promoter modified strain by electrical pulse method (refer to J.P. KOKAI No. 2-207791). The cells were spread on CM2B media plates (comprising 10 g/l of polypeptone, 10 g/l of bactoyeast extract, 5 g/l of NaCl, 10 µg/ml of biotin and 15 g/l of agar, and having pH 7.2) and cultured at 25° C. to obtain transformed strains. These transformants were cultured in CM2B liquid medium in a test tube overnight and then spread on CM2B medium plates containing 25 µg/ml of kanamycin and cultured at 34° C. to obtain a strain caused by once-recombination which contains plasmid pSFKTPDHpro3510 on its chromosome inserted by the homologous recombination. After single colony isolation, this strain was cultured in CM2B liquid medium in a test tube overnight. After the suitable dilution, it was spread on CM2B medium plates and cultured at 31.5° C. After the colonies began to appear, the replicas were made on CM2B medium plates containing 25 µg/ml of kanamycin to obtain kanamycin-sensitive strains. Since two kinds of the strains, i.e. a strain having the sequence of wild type strain for the promoter region of pdhA gene and another strain having the mutation introduced therein, could be occurred, this region was sequenced. Thus, a promoter modified strain, wherein the mutation had been introduced into the promoter region of pdhA gene, was obtained. In this strain, –35 region and –10 region of promoter of pdhA gene had been changed to the consensus sequence of coryneform bacteria. This strain was named GD3510.

TABLE 18

| Strain | β-Galactosidase activity (relative value) |
|---|---|
| ATCC13869/pNEOLBPDHApro1 | 1 |
| ATCC13869/pNEOLBPDHApro10 | 6 |
| ATCC13869/pNEOLBPDHApro3510 | 7.5 |

These results indicate that the supposed promoter region was the promoter of pdhA gene and that the expression of PdhA can be changed (enhanced) by changing the sequence in this region into the consensus sequence. This fact indicates that the expression can be changed, without using plasmid, by changing the promoter region of pdhA gene.

(6) Construction of Plasmid for Preparation of Promoter Varied Strain:

Since it had been proved that the expression of pdhA can be changed by introducing mutations into the promoter, plasmids for preparing a pdhA promoter modified strains were constructed. Three constructs of the plasmids for the promoter modified strains were constructed. They were plasmids wherein −35 region, −10 region and both of them were changed to the consensus sequence, respectively.

Primers shown in Seq ID No. 42 and Seq ID No. 43 were newly synthesized on the basis of the DNA sequence which had already been cloned. Among synthesized primers, Seq ID No. 42 was the complementary strand of the DNA sequence corresponding to a sequence ranging from base No. 2491 to base No. 2521 in Seq ID No. 33, which was represented from the 5'-end, and to which a sequence comprising three A's followed by four T's at the 5' terminal. Seq ID No. 35 was the complementary strand of the DNA sequence corresponding to the sequence ranging from base No. 5020 to base No. 5039 of pdhA gene in Seq ID No. 33, which was represented from the 5'-end. PCR was conducted by using Seq ID No. 35 and Seq ID No. 42 as the primers and chromosome of Brevibacterium lactofermentum ATCC13869, prepared with Bacterial Genomic DNA Purification Kit (Advanced Genetic Technologies Corp.), as a template under standard reaction conditions described on page 8 of PCR Technology (edited by H. Erlich and published by Stockton Press. 1989). Further, PCR was conducted by using Seq ID No. 41 and Seq ID No. 43 and chromosome of Brevibacterium lactofermentum ATCC13869 as a template. The PCR products thus obtained were purified by an ordinary method. PCR was conducted by using PCR products obtained by using Seq ID No. 35 and No. 42 PCR products obtained by using Seq ID No. 41 and Seq ID No. 43 and Seq ID No. 35 and 43 as the primers. The PCR condition was as follows: The concentration of these four DNA would be 10 μM in the reaction cocktail and La taq (Takara Shuzo Co., Ltd.) was used without template. PCR products were purified by an ordinary method, and reacted with restriction enzyme Sal I and Xho I. The fragments thus obtained were ligated with fragments obtained by digesting temperature-sensitive plasmid pSFKT2 with SalI, which can replicate in a coryneform bacterium, by using Ligation Kit (Takara Shuzo Co., Ltd.). After the transformation with competent cells (Takara Shuzo Co., Ltd.) of E. coli JM109, the cells was spread on the L-medium plates(comprising 10 g/l of bactotryptone, 5 g/l of bactoycast extract, 5 g/l of NaCl and 15 g/l of agar and having pH 7.2) containing 10 μg/ml of IPTG (isopropyl-β-D-thiogalactopyranoside), 40 μg/ml of X-Gal (5-bromo-4-chloro-3-indolyl-β-D-galactoside) and 25 μg/ml of kanamycin. After overnight incubation, white colonies were taken and transformants were obtained after single colon isolation. From the transformants, plasmids were prepared by the alkali method (Seibutsu Kogaku Jikken-sho edited by Nippon Seibutsu Kogaku-kai and published by Baifukan, p. 105, 1992). After sequencing DNA fragments inserted into the vector, the base sequence was compared with that of pdhA gene reported in sequence No. 33. The plasmid containing DNA fragments, wherein only the sequences in −35 region and −10 region of the promoter were changed to the consensus sequence of the coryneform bacteria, inserted therein was named pSFKTPDHApro3510.

A plasmid wherein −35 region of the promoter of pdhA gene had been changed to the consensus sequence of coryneform bacteria, and also plasmid wherein −10 region of the promoter of pdhA gene had been changed to the consensus sequence of coryneform bacteria were constructed in the same manner as that described above except that Seq ID No. 41 in the Sequence Listing was replaced with Seq ID No. 39 and 40, respectively. These plasmids were named pSFKT-PDHApro35 and pSFKTPDHApro10, respectively.

(7) Preparation of Promoter Modified Strains:

Strains having modified pdhA gene promoter were prepared by the homologous recombination by using the plasmid for preparing promoter varied strain constructed in the above-described step (6).

First, GC25 was transformed with plasmid pSFKTP-DHApro3510 for preparing promoter modified strain by electrical pulse method (refer to J.P. KOKAI No. 2-207791). The cells were spread on CM2B medium plates (comprising 10 g/l of polypeptone, 10 g/l of bactoyeast extract, 5 g/l of NaCl, 10 μg/ml of biotin and 15 g/l of agar, and having pH 7.2) and cultured at 25° C. to obtain transformed strains. These transformants were cultured in CM2B liquid medium in a test tube overnight and then spread on CM2B medium plates containing 25 μg/ml of kanamycin and cultured at 34° C. to obtain a a strain caused by once-recombination which contains plasmid pSFKTPDHpro3510 on its chromosome inserted by the homologous recombination. After single colony isolation, this strain was cultured in CM2B liquid medium in a test tube overnight. After the suitable dilution, it was spread on CM2B medium plates and cultured at 31.5° C. After the colonies began to appear, the repilicas were made on CM2B medium plates containing 25 μg/ml of kanamycin to obtain kanamycin-sensitive strains. Since two kinds of the strains, i.e. a strain having the sequence of wild type strain for the promoter region of pdhA gene and another strain having the mutation introduced therein, could be occured, this region was sequenced. Thus, a promoter modified strain, wherein the mutation had been introduced into the promoter region of pdhA gene, was obtained. In this strain, −35 region and −10 region of promoter of pdhA gene had been changed to the consensus sequence of coryneform bacteria. This strain was named GD3510.

Strains wherein −35 region or −10 region of promoter of pdhA gene had been changed to the consensus sequence of coryneform bacteria were obtained in the same manner as that described above except that above described plasmid pSFKTPDHApro3510 for producing the promoter modified strain was replaced with plasmid pSFKTPDHApro35 and pSFKTPDHApro10 for producing promoter modified strains and they were named GD35 and GD10, respectively.

(8) Evaluation of the Results of Flask Culture of pdhA Gene Promoter Modified Strains:

The flask culture for producing L-glutamic acid was conducted with three kinds of pdhA gene promoter modified strains obtained as described above. Each of the cells of the promoter modified strains GD3510, GD35, GD10 and GC25 obtained by the culture on CM2B medium plates was inoculated into a medium (comprising 1 liter of pure water containing 30 g of glucose, 1 g of $KH_2PO_4$, 0.4 g of $MgSO_4$ $7H_2O$, 30 g of $(NH_4)_2SO_4$, 0.01 g of $FeSO_4$ $7H_2O$, 0.01 g of $MnSO_4$ $7H_2O$, 15 ml of soybean hydrolyzate, 200 μg of thiamine hydrochloride, 60 μg of biotin and 50 g of $CaCO_3$; and having a pH adjusted to 8.0 with KOH). Then the culture was shaked at 31.5° C. until the sugar in the medium had been consumed. The obtained products were inoculated into the medium of the same composition as that described above in an amount of 5%, and the shaking culture was conducted at 37° C. until sugar in the medium had been consumed. After the completion of the culture, the amount of L-glutamic acid accumulated in the culture liquid was determined with Biotic Analyzer AS-210 (a product of Asahi Chemical Industry Co., Ltd.). The results are shown in

TABLE 19

| Strain | L-glutamic acid (g/dl) |
| --- | --- |
| GC25 | 1.9 |
| GD35 | 2.0 |
| GD10 | 2.0 |
| GD3510 | 2.1 |

It was apparent from the results that the obtained promoter modified strains provided improved Glu yields.

EXAMPLE 6

Introduction of Mutation into Promoter Region of Arginosuccinate Synthase Gene:

1) Determination of DNA Sequence in the Upstream of argG Gene:

In order to amplify argG gene of *Brevibacterium flavum* by PCR, the DNA sequences in the upstream and downstream regions of the ORF were determined. The determination of the DNA sequences was conducted by synthesizing a primer based on the known DNA sequence (Gen Bank accession AF030520) of ORF of argG gene of *Corynebacterium glutamicum* and using in vitro LA PCR cloning kit (Takara shuzo Co., Ltd.) in accordance with the instruction manual included in the kit. As primers, they were specifically used oligonucleotides (primers 1 and 2) having the DNA sequences set out as Seq ID No. 44 and Seq ID No. 45 for the upstream region, and oligonucleotides (primers 3 and 4) having the DNA sequences set out as Seq ID No. 46 and Seq ID No. 47 for the downstream region. The DNA sequences in the upstream and downstream region of argG were determined by completely digesting chromosome DNA of 2247 strain (ATCC14067), i.e., wild type strain of *Brevibacterium flavum*, with a restriction enzyme EcoRI, conducting first PCR with the primer 2 or 3 (having sequence No. 45 or 46), and conducting second PCR with the primer 1 or 2 (having sequence No. 44 or 47).

2) Prediction of Promoter Region:

A promoter-like sequence in the upstream of ORF of argG gene was search for the above-described sequences with a commercially available software (GENETYX). The mutation was introduced into a region of the highest score (about 120 bp upstream of the first ATG). Then, the promoter activity was measured.

3) Introduction of Mutations into Promoter Sequence, and Determination of Activity of Mutant Promoters:

Mutation-introducing primers 9, 10, 11, 12 or 13 and 7 (having sequence No. 52, 53, 54, 55, 56, or 50, respectively) for a region of the highest score were used, and the first PCR was conducted with chromosomal DNA of AJ12092 strain as a template. The second PCR was conducted with the same chromosomal DNA as the template by using the PCR product as the primer for 3'-end and also using the primer 8 having sequence No. 51 as the primer on 5'-end to obtain DNA fragments having the mutation introduced in the intended promoter region. To determine the activity of the mutant promoters, these DNA fragments were inserted into SmaI site of promoter probe vector pNEOL so that they were in the same direction with lacZ reporter gene to obtain plasmids pNEOL-1, pNEOL-2, pNEOL-3, pNEOL-4 and pNEOL-7. As a control for the activity, plasmid pNEOL-0 was constructed by inserting the DNA fragment, obtained by PCR using chromosomal DNA of AJ12092 strain and primers 7 and 8, into the upstream of lacZ gene of pNEOL.

pNEOL-0, pNEOL-1, pNEOL-2, pNEOL-3, pNEOL-4 and pNEOL-7 were introduced into AJ12092 strain, respectively. The plasmids were introduced by electrical pulse method (J.P. KOKAI No. 2-207791). The transformants were selected on CM2G medium plates (comprising 1 liter of pure water containing 10 g of polypeptone, 10 g of yeast extract, 5 g of glucose, 5 g of NaCl and 15 g of agar, and having pH 7.2) containing 4 μg/ml of chloramphenicol, as chloramphenicol-resistant strains.

These strains were each spread on an agar medium (containing 0.5 g/dl of glucose, 1 g/dl of polypeptone, 1 g/dl of yeast extract, 0.5 g/dl of NaCl and 5 μg/l of chloramphenicol), and cultured at 31.5° C. for 20 hours. One aze of the cells thus obtained was inoculated into a medium [containing 3 g/dl of glucose, 1.5 g/dl of ammonium sulfate, 0.1 g/dl of $KH_2PO_4$, 0.04 g/dl of $MgSO_4$, 0.001 g/dl of $FeSO_4$, 0.01 g/dl of $MnSO_4$, 5 μg/dl of $VB_1$, 5 μg/dl of biotin and 45 mg/dl (in terms of N) of soybean hydrolyzate]. After the culture at 31.5° C. for 18 hours, β-galactosidase activity of the obtained cells was determined as described in Example 4(4).

Since β-galactosidase activity was detected in AJ12092/pNEOL-0 as shown in Table 20, it was found that the DNA fragment inserted into the upstream of the gene of lacZ structure functioned as a promoter. In addition, β-galactosidase activity of each of the plasmid-introduced strains was higher than that of AJ12092/pNEOL-0. It was thus found that the transcription activity was increased by the introduction of the mutation into the promoter-like sequence, as shown in Table 20.

TABLE 20

| | Relative activity (AJ12092/pNEOL-0 = 1) |
| --- | --- |
| AJI12092 | nd |
| AJI12092/pNEOL-0 | 1.0 |
| AJI12092/pNEOL-1 | 2.8 |
| AJI12092/pNEOL-2 | 2.7 |
| AJI12092/pNEOL-3 | 1.8 |
| AJI12092/pNEOL-4 | 0.8 |
| AJI12092/pNEOL-7 | 3.0 |

4) Construction of a Plasmid for Introduction of Mutation:

PCR was conducted by using primers 14 and 15 (having the sequence of Seq ID No. 57 and Seq ID No. 57) with chromosomal DNA of AJ12092 strain as the template. These DNA fragments thus obtained were inserted into a smaI site in a multicloning site of cloning vector pHSG398 (a product of TaKaRa) to construct plasmid p0. Then, p0 was digested with restriction enzymes EcoRV and BspHI, and also pNEOL-3 and pNEOL-7 were digested with restriction enzymes EcoRV and BspHI. DNA fragments thus obtained were ligated to obtain mutation-introducing plasmids p3 (mutant derived from mutation-introducing primer 11) and p7 (mutant derived from mutation-introducing primer 13).

5) Introduction of Mutation-Introducing Plasmids into Arg-Producing Bacterium:

Each of the plasmids thus obtained was introduced into Arg-producing bacterium of the strain *Brevibacterium lactofermentum* AJ12092 by electrical pulse method (J. P, KOKAI No. 2-207791). Since these plasmids could not autonomously replicate in Brevibacterium, only the strains obtained by integrating these plasmids into the chromosome by homologous recombination could be selected as Cm-resistant strains. Strains in which the mutation-introducing plasmid was integrated into the chromosome were selected as chloramphenicol-resistant strains on CM2G medium plates (comprising 1 liter of pure water containing 10 g of polypeptone, 10 g of yeast extract, 5 g of glucose, 5 g of NaCl and 15 g of agar, and having pH 7.2) containing 5 μg/ml of chloramphenicol. Then, Cm-sensitive strains were selected in which the promoter region of argG gene was replaced with the intended modified sequence.

As a result, a strain substituted with P3 sequence (AJ12092-P3) and a strain substituted with P7 sequence (AJ12092-P7) were obtained.

(6) Cloning of argG Gene

Based on the DNA sequence determined as in (1), oligonucleotides (primers 5 and 6) having the DNA sequence set out in Seq ID No. 48 and Seq ID No. 49 were synthesized to conduct PCR using chromosomal DNA of *Brevibacterium flavum* as a template. The PCR reaction was conducted in 25 cycles, each cycle consisting of 94° C. for 30 seconds, 55° C. for one second and 72° C. for 2 minutes and 30 seconds. The thus-obtained DNA fragment was cloned to SmaI site in multi-cloning site of cloning vector pSTV29 (Takara shuzo Co. Ltd.) to obtain pSTVargG. Furthermore, pargG was prepared by inserting into SalI site of pSTVargG a fragment containing the replication origin obtained by treating pSAK4 set out in Example 1 with SalI.

7) Introduction of pargG into Brev.:

pargG was introduced into the strain *Brevibacterium lactofermentum* AJ12092. Plasmid was introduced by electrical pulse method (J. P, KOKAL No. 2-207791). The transformant was selected as chloramphenicol-resistant strain on CM2G medium plates (comprising 1 liter of pure water containing 10 g of polypeptone, 10 g of yeast extract, 5 g of glucose, 5 g of NaCl and 15 g of agar, and having pH 7.2) containing 4 μg/ml of chloramphenicol.

8) ArgG Activity of Promoter Modified Strains:

ArgG activities of the above-described two kinds of argG promoter modified strains and a strain obtained by amplifying argG with plasmid (AJ12092/pargG) were determined. These strains were each spread on a agar medium (containing 0.5 g/dl of glucose, 1 g/dl of polypeptone, 1 g/dl of yeast extract, 0.5 g/dl of NaCl and 5 μg/l of chloramphenicol), and cultured at 31.5° C. for 20 hours. One aze of the cells thus obtained were inoculated into a medium [containing 3 g/dl of glucose, 1.5 g/dl of ammonium sulfate, 0.1 g/dl of $KH_2PO_4$, 0.04 g/dl of $MgSO_4$, 0.001 g/dl of $FeSO_4$, 0.01 g/dl of $MnSO_4$, 5 μg/dl of $VB_1$, 5 μg/dl of biotin and 45 mg/dl (in terms of N) of soybean hydrolyzate]. After the culture at 31.5° C. for 18 hours, ArgG activity of the obtained cells was determined by the method described above [Journal of General Microbiology (1990), 136, 1177–1183]. ArgG activities of the above-described two kinds of ArgG promoter modified strains and the strain (AJ12092/pargG) obtained by amplifying argG with plasmid are shown in Table 21. It is apparent from Table 21 that by introducing the mutation into the promoter, ArgG activity of AJ12092-P3 was increased to about twice as high as that of the parent strain, and the activity of AJ12092-P7 was increased to about three times as high as that of the parent strain. ArgG activity of AJ12092/pargG was about 4.5 times as high as that of the parent strain.

TABLE 21

| | Relative activity (AJ12092 = 1) |
|---|---|
| AJI12092 | 1.0 |
| AJI12092-P3 | 2.1 |
| AJI12092-P7 | 2.9 |
| AJI12092/pargG | 4.4 |

9) Arg Production by Promoter Modified Strains:

The flask culture of each of argG promoter modified strains was conducted. As controls, parent strain AJ12092 and AJ12092/pargG were also cultured. These strains were each inoculated into a medium [containing 0.1 g/dl of $KH_2PO_4$, 0.04 g/dl of $MgSO_4$, 0.001 g/dl of $FeSO_4$, 0.01 g/dl of $MnSO_4$, 5 μg/dl of $VB_1$, 5 μg/dl of biotin and 45 mg/dl (in terms of N) of soybean hydrolyzate]; and then spread on an agar medium (containing 0.5 g/dl of glucose, 1 g/dl of polypeptone, 1 g/dl of yeast extract, 0.5 g/dl of NaCl and 5 μg/l of chloramphenicol), and cultured at 31.5° C. for 20 hours. One aze of the cells were cultured in a flask containing 4 g/dl of glucose and 6.5 g/dl of ammonium sulfate at 31.5° C. until glucose had been completely consumed. The absorbance (CD620) of the culture liquid diluted to a concentration of 1/51 with 0.2 N HCl solution, the quantity of arginine produced (concentration: g/dl) and culture time were shown in Table 22.

It is apparent from Table 22 that when argG promoter modified strain was used, the yield of arg was increased to a level equal to that of argG amplified with plasmid. As for the promoter varied strains, both AJ12092-P3 and AJ12092-P7 had the culture time equal to that of the parent strain, while the culture time of the plasmid amplified strain was increased. It was thus apparent that Arg productivity thereof was higher than that of the plasmid amplified strain.

TABLE 22

| | OD | Arg (g/dl) | Culture time (h) | Productivity (g/dl/h) |
|---|---|---|---|---|
| AJI2092 | 0.502 | 1.25 | 48 | 0.026 |
| AJI2092-P3 | 0.510 | 1.47 | 48 | 0.031 |
| AJI2092-P7 | 0.514 | 1.43 | 48 | 0.030 |
| AJI2092/pargG | 0.520 | 1.47 | 52 | 0.028 |

EXAMPLE 7

Introduction of Mutation into GDH Gene Promoter Region of Coryneform Glutamate-Producing Bacterium (1) Construction of Mutant gdh Plasmids:

Plasmids having GDH promoter sequence of FGR1 strain and FGR2 strain described in Example 2 were constructed by site directed mutagenesis. For obtaining GDH promoter sequence of FGR1 strain, PCR was conducted by using synthetic DNA shown in Seq ID No. 59 and synthetic DNA shown in No. 62 as the primers and chromosomal DNA of ATCC13869 as the template; and on the other hand, PCR was conducted by using synthetic DNA shown in Seq ID No. 60 and synthetic DNA shown in Seq ID No. 61 as the primers with chromosomal DNA of ATCC13869 as the template. Further, PCR was conducted by using synthetic DNAs shown in Seq ID Nos. 59 and Seq ID No. 60 as the primers with a mixture of these PCR products as the template. The PCR product thus obtained was inserted into SmaI site of pSFKT2 (Japanese Patent Application No. 11-69896) to construct pSFKTG11. To obtain GDH promoter sequence of FGR2 strain, PCR was conducted by using synthetic DNA shown in Seq ID No. 59 and synthetic DNA shown in Seq ID No. 64 as the primers and chromosomal DNA of ATCC13869 as the template; and on the other hand, PCR was conducted by using synthetic DNA shown in Seq ID No. 60 and synthetic DNA shown in Seq ID No. 63 as the primers and chromosomal DNA of ATCC13869 as the template. Further, PCR was conducted by using synthetic DNA shown in Seq ID No. 59 and Seq ID No. 60 as the primers and a mixture of these PCR products as the template. The PCR product thus obtained was inserted into SmaI site of pSFKT2 (Japanese Patent Application No. 11-69896) to construct pSFKTG07. The DNA sequences of the fragments inserted into SmaI sites of pSFKTG11 and pSFKTG07 were determined to confirm that no mutation was introduced into other regions than the promoter region in GDH.

(2) Construction of gdh Promoter Modified Strains:

Then, pSFKTG11 and pSFKTG07 were introduced into AJ13029 strain by electrical pulse method, and transformants which grew on CM2B plates containing 25 µg/ml of kanamycin at 25° C. were selected. The transformants were cultured at 34° C. to select strains which were resistant to kanamycin at 34° C. The fact that a strain is resistant to kanamycin at 34° C. indicates that pSFKTG11 or pSFKTG07 was thus integrated on the chromosome of AJ13029 strain. Kanamycin-sensitive strains were obtained from the strains in which the plasmid was integrated on the chromosome. The GDH promoter sequences of these strains were determined. The strains having the same gdh promoter sequence as those of pSFKTG11 and pSFKTG07 were named GA01 and GA02, respectively.

(3) Confirmation of L-Glutamic Acid-Productivity of gdh Promoter Modified Strains:

The glutamic acid productivities of strains GA01 and GA02 and the parent strain AJ13029 were confirmed in the same manner as that of Example 2 (2) given above. As a result, a remarkable improvement in the accumulation of glutamic acid was recognized in GA01 and GA02 as shown in Table 23.

TABLE 23

| Strain | Glu (g/dl) | Specific activity of GDH | Relative value |
|---|---|---|---|
| AJ13029 | 2.6 | 7.7 | 1.0 |
| GA01 | 3.0 | 22.3 | 2.9 |
| GA02 | 2.9 | 27.0 | 3.5 |

(4) Construction of Self-Cloning Type gdh Plasmid:

First, self-cloning vector pAJ220 was constructed. pAJ226 (J.P. KOKAI No. 61-152289) was treated with EcoRV and PstI to prepare a fragment containing a region which could be autonomously replicated in a coryneform bacterium. The fragment was ligated with about 0.7 kb of the DNA fragment obtained by treating pAJ224 (J.P. KOKAI No. Sho 61-152289) with EcoRV and PstI to obtain a plasmid pAJ220. This plasmid could autonomously replicate in a coryneform bacterium, and it could afford trimethoprim resistance to the host.

PCR reaction was conducted by using synthetic DNA shown in Seq ID No. 65 and Seq ID No. 66 as the primers and chromosomal DNA of wild-type coryneform bacterium strain ATCC13869 as the template. The gdh gene fragment thus obtained was inserted in BalI site of pAJ220 to construct pAJ220G. The promoter was present near BalI site of pAJ220, and the expression of the inserted gene was increased depending on the direction of the gene inserted into BalI site. PAJ220G and pGDH were introduced into ATCC13869 strain by electrical pulse method. GDH activities of the strains thus constructed were determined by the method stated in above-described step (1). As a result, GDH activity of the strain into which pAJ220G had been introduced was about 1.5 times as high as that of the strain into which dGDH had been introduced as shown in Table 24.

TABLE 24

| Strain | Specific activity of GDH | Relative value |
|---|---|---|
| ATCC13869 | 7.7 | 1.0 |
| ATCC13869/pGDH | 82.7 | 10.7 |
| ATCC13869/pAJ220G | 120.1 | 15.6 |

(5) Investigations on Influence of gdh Activity on the Yield and By-Produced Asp:

pGDH and pAJ220G were introduced into AJ13029 by electrical pulse method. Each of these strains and those obtained in above-described step (2) was inoculated into a seed culture medium having a composition shown in Table 25, and the shaking culture was conducted at 31.5° C. for 24 hours to obtain the seed culture. 300 ml of medium for main culture having a composition shown in Table 25 was placed in each of 500 ml glass jar fermenter and then sterilized by heating. 40 ml of the seed cultures as described above were inoculated into the medium. The culture was started at a temperature of 31.5° C. while the stirring rate and the aeration rate were controlled at 800 to 1300 rpm and ½ to ⅓ vvm, respectively. The pH of the culture liquid was kept at 7.5 with gaseous ammonia. The temperature was shifted to 37° C. 8 hours after the initiation of the culture. The culture was terminated when glucose had been completely consumed in 20 to 40 hours, and the quantity of L-glutamic acid produced and accumulated in the culture liquid were determined (Table 26). The GDH activity for obtaining the highest yield was about 3-times as high. When GDH activity was further elevated, the degree of the improvement in the yield was reduced. When the GDH activity was elevated to about 16-times, the yield was rather reduced. Amino acids produced as by-products were analyzed with Hitachi Amino Acid Analyzer L-8500 to find that as GDH activity was elevated, the amount of accumulated aspartic acid and alanine was increased. These results proved the following facts: For increasing the yield of glutamic acid, it is necessary to suitably increase GDH activity so as not to cause a remarkable increase in the amount of aspartic acid and alanine. One of the effective methods therefor comprises the introduction of various mutations into gdh promoter to control GDH activity to about 3-times as high as that of the parent strain.

TABLE 25

| | Concentration | |
|---|---|---|
| Ingredient | Seed culture | Main culture |
| Glucose | 50 g/l | 150 g/l |
| KH$_2$PO$_4$ | 1 g/l | 2 g/l |
| MgSO$_4$.7H$_2$O | 0.4 g/l | 1.5 g/l |
| FeSO$_4$.7H$_2$O | 10 mg/l | 15 mg/l |
| MnSO$_4$.4H$_2$O | 10 mg/l | 15 mg/l |
| Soybean protein hydrolyzate | 20 ml/l | 50 ml/l |
| Biotin | 0.5 mg/l | 2 mg/l |
| Thiamine hydrochloride | 2 mg/l | 3 mg/l |

TABLE 26

| Strain | Glu (g/dl) | Asp (mg/dl) | Ala (mg/dl) | Relative activity of GDH | Relative value |
|---|---|---|---|---|---|
| AJ 13029 | 8.3 | 49 | 60 | 7.7 | 1.0 |
| GA01 | 9.0 | 145 | 152 | 22.3 | 2.9 |
| GA02 | 8.9 | 153 | 155 | 27.0 | 3.5 |
| AJ13029/pGDH | 8.8 | 201 | 190 | 82.7 | 10.7 |
| AJ13029/pAJ220G | 7.5 | 290 | 590 | 120.12 | 15.6 |

What is claimed is:

1. A method of producing L-glutamic acid, comprising:
culturing a coryneform bacterium expressing an enzyme encoded by a coryneform bacteria glutamic acid biosynthesizing gene, in a medium for a time and under conditions suitable to produce and accumulate said L-glutamic acid in the medium, and
collecting said L-glutamic acid from the medium;
wherein the glutamic acid biosynthesizing gene is located on a chromosome of the coryneform bacterium and the enzyme is selected from the group consisting of glutamate dehydrogenase, citrate synthase, isocitrate dehydrogenase, pyruvate dehydrogenase, and aconitase, said glutamic acid biosynthesizing gene comprising a DNA sequence situated at about position −35 from the transcription start site of the glutamic acid biosynthesizing gene, wherein said DNA sequence is selected from the group consisting of TTGTCA and TTGCCA,
wherein said producing L-glutamic acid is at a level greater than the production of L-glutamic acid by the corresponding wild-type coryneform bacterium.

2. The method of claim 1, wherein said glutamic acid biosynthesizing gene encodes glutamate dehydrogenase.

3. The method of claim 1, wherein said glutamic acid biosynthesizing gene encodes citrate synthase.

4. The method of claim 1, wherein said glutamic acid biosynthesizing gene encodes isocitrate dehydrogenase.

5. The method of claim 1, wherein said glutamic acid biosynthesizing gene encodes pyruvate dehydrogenase.

6. The method of claim 1, wherein said glutamic acid biosynthesizing gene encodes aconitase.

7. The method of claim 1, wherein said DNA sequence situated at about position −35 from the transcription start site of the glutamic acid biosynthesizing gene further comprises TATAAT situated at about position −10 from the transcription start site.

8. The method of claim 1, wherein said DNA sequence is TTGTCA.

9. The method of claim 8, wherein said glutamic acid biosynthesizing gene further comprises TATAAT situated at about position −10 from the transcription start site of the gene.

10. The method of claim 8, wherein said glutamic acid biosynthesizing gene further comprises TATAAC situated at about position −10 from the transcription start site of the gene.

11. The method of claim 1, wherein said DNA sequence is TTGCCA.

12. The method of claim 11, wherein said glutamic acid biosynthesizing gene further comprises TATAAT situated at about position −10 from the transcription start site of the gene.

13. The method of claim 11, wherein said glutamic acid biosynthesizing gene further comprises TATAAC situated at about position −10 from the transcription start site of the gene.

14. The method of claim 1, wherein said glutamic acid biosynthesizing gene encodes isocitrate dehydrogenase and wherein said DNA sequence is TTGCCA.

15. The method of claim 14, wherein said glutamic acid biosynthesizing gene further comprises TATAAT situated at about position −10 from the transcription site of the gene.

16. The method of claim 1, wherein said glutamic acid biosynthesizing gene encodes pyruvate dehydrogenase and wherein said DNA sequence is TTGCCA.

17. The method of claim 16, wherein said glutamic acid biosynthesizing gene further comprises TATAAT situated at about position −10 from the transcription site of the gene.

18. A method of producing L-glutamic acid, comprising:
culturing a coryneform bacterium expressing an enzyme encoded by a coryneform bacteria glutamic acid biosynthesizing gene, in a medium for a time and under conditions suitable to produce and accumulate said L-glutamic acid in the medium, and
collecting said L-glutamic acid from the medium;
wherein the glutamic acid biosynthesizing gene is located on a chromosome of the coryneform bacterium and the enzyme is selected from the group consisting of glutamate dehydrogenase, citrate synthase, isocitrate dehydrogenase, pyruvate dehydrogenase, and aconitase, said glutamic acid biosynthesizing gene comprising a DNA sequence situated at about position −10 from the transcription start site of the glutamic acid biosynthesizing gene, wherein said DNA sequence is TATAAC,
wherein said producing L-glutamic acid is at a level greater than the production of L-glutamic acid by the corresponding wild-type coryneform bacterium.

19. The method of claim 18, wherein said glutamic acid biosynthesizing gene encodes glutamate dehydrogenase.

20. The method of claim 18, wherein said glutamic acid biosynthesizing gene encodes citrate synthase.

21. The method of claim 20, wherein said glutamic acid biosynthesizing gene further comprises TTGACA situated at about position −35 from the transcription start site of the gene.

22. The method of claim 18, wherein said glutamic acid biosynthesizing gene encodes isocitrate dehydrogenase.

23. The method of claim 22, wherein said glutamic acid biosynthesizing gene further comprises TTGACA situated at about position −35 from the transcription start site of the gene.

24. The method of claim 18, wherein said glutamic acid biosynthesizing gene encodes pyruvate dehydrogenase.

25. The method of claim 18, wherein said glutamic acid biosynthesizing gene encodes aconitase.

26. The method of claim 18, wherein said glutamic acid biosynthesizing gene further comprises TTGACA situated at about position −35 from the transcription site of the gene.

* * * * *

SEQUENCE LISTING

<160> NUMBER OF SEQ ID NOS: 66

<210> SEQ ID NO 1
<211> LENGTH: 46
<212> TYPE: DNA
<213> ORGANISM: Artificial sequence
<220> FEATURE:
<223> OTHER INFORMATION: Synthetic DNA

<400> SEQUENCE: 1
ttaattcttt gtggtcatat ctgcgacact gccataattt gaacgt                46

<210> SEQ ID NO 2
<211> LENGTH: 46
<212> TYPE: DNA
<213> ORGANISM: Artificial sequence
<220> FEATURE:
<223> OTHER INFORMATION: Synthetic DNA

<400> SEQUENCE: 2
ttaattcttt gcggtcatat ctgcgacact gccataattt gaacgt                46

<210> SEQ ID NO 3
<211> LENGTH: 46
<212> TYPE: DNA
<213> ORGANISM: Artificial sequence
<220> FEATURE:
<223> OTHER INFORMATION: Synthetic DNA

<400> SEQUENCE: 3
ttaattcttt gtggtcatat ctgcgacact gctataattt gaacgt                46

<210> SEQ ID NO 4
<211> LENGTH: 46
<212> TYPE: DNA
<213> ORGANISM: Artificial sequence
<220> FEATURE:
<223> OTHER INFORMATION: Synthetic DNA

<400> SEQUENCE: 4
ttaattcttt gttgacatat ctgcgacact gctataattt gaacgt                46

<210> SEQ ID NO 5
<211> LENGTH: 46
<212> TYPE: DNA
<213> ORGANISM: Artificial sequence
<220> FEATURE:
<223> OTHER INFORMATION: Synthetic DNA

<400> SEQUENCE: 5
ttaattcttt gttgccatat ctgcgacact gctataattt gaacgt                46

<210> SEQ ID NO 6
<211> LENGTH: 46
<212> TYPE: DNA
<213> ORGANISM: Artificial sequence
<220> FEATURE:
<223> OTHER INFORMATION: Synthetic DNA

<400> SEQUENCE: 6
ttaattcttt gttgtcatat ctgcgacact gctataattt gaacgt                46

<210> SEQ ID NO 7
<211> LENGTH: 30

```
<212> TYPE: DNA
<213> ORGANISM: Artificial sequence
<220> FEATURE:
<223> OTHER INFORMATION: Synthetic DNA

<400> SEQUENCE: 7
gtcgacaata gcctgaatct gttctggtcg                                      30

<210> SEQ ID NO 8
<211> LENGTH: 30
<212> TYPE: DNA
<213> ORGANISM: Artificial sequence
<220> FEATURE:
<223> OTHER INFORMATION: Synthetic DNA

<400> SEQUENCE: 8
aagcttatcg acgctcccct ccccaccgtt                                      30

<210> SEQ ID NO 9
<211> LENGTH: 20
<212> TYPE: DNA
<213> ORGANISM: Artificial sequence
<220> FEATURE:
<223> OTHER INFORMATION: Synthetic DNA

<400> SEQUENCE: 9
atcggtataa cgtgttaacc                                                 20

<210> SEQ ID NO 10
<211> LENGTH: 20
<212> TYPE: DNA
<213> ORGANISM: Artificial sequence
<220> FEATURE:
<223> OTHER INFORMATION: Synthetic DNA

<400> SEQUENCE: 10
atcggtataa tgtgttaacc                                                 20

<210> SEQ ID NO 11
<211> LENGTH: 40
<212> TYPE: DNA
<213> ORGANISM: Artificial sequence
<220> FEATURE:
<223> OTHER INFORMATION: Synthetic DNA

<400> SEQUENCE: 11
gatttgacaa aaccgcattt atcggtataa tgtgttaacc                           40

<210> SEQ ID NO 12
<211> LENGTH: 28
<212> TYPE: DNA
<213> ORGANISM: Artificial sequence
<220> FEATURE:
<223> OTHER INFORMATION: Synthetic DNA

<400> SEQUENCE: 12
agggatccgt ccagtctcag acagcatc                                        28

<210> SEQ ID NO 13
<211> LENGTH: 17
<212> TYPE: DNA
<213> ORGANISM: Artificial sequence
<220> FEATURE:
<223> OTHER INFORMATION: Synthetic DNA

<400> SEQUENCE: 13
```

```
caggaaacag ctatgac                                                    17

<210> SEQ ID NO 14
<211> LENGTH: 20
<212> TYPE: DNA
<213> ORGANISM: Artificial sequence
<220> FEATURE:
<223> OTHER INFORMATION: Synthetic DNA

<400> SEQUENCE: 14
gaattcgctc ccggtgcagc                                                 20

<210> SEQ ID NO 15
<211> LENGTH: 20
<212> TYPE: DNA
<213> ORGANISM: Artificial sequence
<220> FEATURE:
<223> OTHER INFORMATION: Synthetic DNA

<400> SEQUENCE: 15
gatgcagaat tccttgtcgg                                                 20

<210> SEQ ID NO 16
<211> LENGTH: 28
<212> TYPE: DNA
<213> ORGANISM: Artificial sequence
<220> FEATURE:
<223> OTHER INFORMATION: Synthetic DNA

<400> SEQUENCE: 16
tggattgctg gctataatgg tgtcgtga                                        28

<210> SEQ ID NO 17
<211> LENGTH: 53
<212> TYPE: DNA
<213> ORGANISM: Artificial sequence
<220> FEATURE:
<223> OTHER INFORMATION: Synthetic DNA

<400> SEQUENCE: 17
caacccacgt tcagttgaca actactggat tgctggctat aatggtgtcg tga            53

<210> SEQ ID NO 18
<211> LENGTH: 53
<212> TYPE: DNA
<213> ORGANISM: Artificial sequence
<220> FEATURE:
<223> OTHER INFORMATION: Synthetic DNA

<400> SEQUENCE: 18
caacccacgt tcagttgact actactggat tgctggctaa agtggtgtcg tga            53

<210> SEQ ID NO 19
<211> LENGTH: 28
<212> TYPE: DNA
<213> ORGANISM: Artificial sequence
<220> FEATURE:
<223> OTHER INFORMATION: Synthetic DNA

<400> SEQUENCE: 19
ggctgaaact gctataatag gcgccagc                                        28

<210> SEQ ID NO 20
<211> LENGTH: 51
<212> TYPE: DNA
<213> ORGANISM: Artificial sequence
```

```
<220> FEATURE:
<223> OTHER INFORMATION: Synthetic DNA

<400> SEQUENCE: 20
ggaaacacgg cgttgccatg cggggctgaa actgctataa taggcgccag c          51

<210> SEQ ID NO 21
<211> LENGTH: 51
<212> TYPE: DNA
<213> ORGANISM: Artificial sequence
<220> FEATURE:
<223> OTHER INFORMATION: Synthetic DNA

<400> SEQUENCE: 21
ggaaacacgg cgttgacatg cggggctgaa actgctataa taggcgccag c          51

<210> SEQ ID NO 22
<211> LENGTH: 22
<212> TYPE: DNA
<213> ORGANISM: Artificial sequence
<220> FEATURE:
<223> OTHER INFORMATION: Synthetic DNA

<400> SEQUENCE: 22
gtgcgggtcc agatgatctt ag                                          22

<210> SEQ ID NO 23
<211> LENGTH: 20
<212> TYPE: DNA
<213> ORGANISM: Artificial sequence
<220> FEATURE:
<223> OTHER INFORMATION: Synthetic DNA

<400> SEQUENCE: 23
gggatcccgg atgaatgtca                                             20

<210> SEQ ID NO 24
<211> LENGTH: 23
<212> TYPE: DNA
<213> ORGANISM: Artificial sequence
<220> FEATURE:
<223> OTHER INFORMATION: Synthetic DNA

<400> SEQUENCE: 24
gcccggggtg ggcgaagaac tcc                                         23

<210> SEQ ID NO 25
<211> LENGTH: 23
<212> TYPE: DNA
<213> ORGANISM: Artificial sequence
<220> FEATURE:
<223> OTHER INFORMATION: Synthetic DNA
<220> FEATURE:
<221> NAME/KEY: misc_feature
<222> LOCATION: (3)..(3)
<223> OTHER INFORMATION: n = inosine
<220> FEATURE:
<221> NAME/KEY: misc_feature
<222> LOCATION: (6)..(6)
<223> OTHER INFORMATION: n = inosine
<220> FEATURE:
<221> NAME/KEY: misc_feature
<222> LOCATION: (9)..(9)
<223> OTHER INFORMATION: n = inosine
<220> FEATURE:
<221> NAME/KEY: misc_feature
<222> LOCATION: (15)..(15)
<223> OTHER INFORMATION: n = inosine
<220> FEATURE:
```

```
<221> NAME/KEY: misc_feature
<222> LOCATION: (18)..(18)
<223> OTHER INFORMATION: n = inosine
<220> FEATURE:
<221> NAME/KEY: misc_feature
<222> LOCATION: (21)..(21)
<223> OTHER INFORMATION: n = inosine

<400> SEQUENCE: 25
acngtntcna tgggnctngg ncc                                             23

<210> SEQ ID NO 26
<211> LENGTH: 23
<212> TYPE: DNA
<213> ORGANISM: Artificial sequence
<220> FEATURE:
<223> OTHER INFORMATION: Synthetic DNA
<220> FEATURE:
<221> NAME/KEY: misc_feature
<222> LOCATION: (6)..(6)
<223> OTHER INFORMATION: n = inosine
<220> FEATURE:
<221> NAME/KEY: misc_feature
<222> LOCATION: (12)..(12)
<223> OTHER INFORMATION: n = inosine
<220> FEATURE:
<221> NAME/KEY: misc_feature
<222> LOCATION: (15)..(15)
<223> OTHER INFORMATION: n = inosine
<220> FEATURE:
<221> NAME/KEY: misc_feature
<222> LOCATION: (18)..(18)
<223> OTHER INFORMATION: n = inosine
<220> FEATURE:
<221> NAME/KEY: misc_feature
<222> LOCATION: (21)..(21)
<223> OTHER INFORMATION: n = inosine

<400> SEQUENCE: 26
ccttcnccgt tnagngtngt ncg                                             23

<210> SEQ ID NO 27
<211> LENGTH: 30
<212> TYPE: DNA
<213> ORGANISM: Artificial sequence
<220> FEATURE:
<223> OTHER INFORMATION: Synthetic DNA

<400> SEQUENCE: 27
ttgcagttaa ccacgaaggt caggttgtcc                                      30

<210> SEQ ID NO 28
<211> LENGTH: 30
<212> TYPE: DNA
<213> ORGANISM: Artificial sequence
<220> FEATURE:
<223> OTHER INFORMATION: Synthetic DNA

<400> SEQUENCE: 28
tggatgagac cacgtgattc tggctcgtcc                                      30

<210> SEQ ID NO 29
<211> LENGTH: 30
<212> TYPE: DNA
<213> ORGANISM: Artificial sequence
<220> FEATURE:
<223> OTHER INFORMATION: Synthetic DNA

<400> SEQUENCE: 29
acagatcctg cacgaaggca tcaacgaggc                                      30
```

```
<210> SEQ ID NO 30
<211> LENGTH: 30
<212> TYPE: DNA
<213> ORGANISM: Artificial sequence
<220> FEATURE:
<223> OTHER INFORMATION: Synthetic DNA

<400> SEQUENCE: 30
tcatcgctgc gggtacctcc tacgccaccc                                          30

<210> SEQ ID NO 31
<211> LENGTH: 2766
<212> TYPE: DNA
<213> ORGANISM: Brevibacterium lactofermentum ATCC13869
<220> FEATURE:
<221> NAME/KEY: CDS
<222> LOCATION: (1)..(2766)
<223> OTHER INFORMATION:

<400> SEQUENCE: 31 atg gcc gat caa gca aaa ctt ggt ggt aag ccc tcg gat gac tct aac         48
Met Ala Asp Gln Ala Lys Leu Gly Gly Lys Pro Ser Asp Asp Ser Asn
 1               5                  10                  15 ttc gcg atg atc cgc gat ggc gtg gca tct tat ttg aac gac tca gat         96
Phe Ala Met Ile Arg Asp Gly Val Ala Ser Tyr Leu Asn Asp Ser Asp
            20                  25                  30 ccg gag gag acc aac gag tgg atg gat tca ctc gac gga tta ctc cag        144
Pro Glu Glu Thr Asn Glu Trp Met Asp Ser Leu Asp Gly Leu Leu Gln
        35                  40                  45 gag tct tct cca gaa cgt gct cgt tac ctc atg ctt cgt ttg ctt gag        192
Glu Ser Ser Pro Glu Arg Ala Arg Tyr Leu Met Leu Arg Leu Leu Glu
    50                  55                  60 cgt gca tct gca aag cgc gta tct ctt ccc cca atg acg tca acc gac        240
Arg Ala Ser Ala Lys Arg Val Ser Leu Pro Pro Met Thr Ser Thr Asp
65                  70                  75                  80 tac gtc aac acc att cca acc tct atg gaa cct gaa ttc cca ggc gat        288
Tyr Val Asn Thr Ile Pro Thr Ser Met Glu Pro Glu Phe Pro Gly Asp
                85                  90                  95 gag gaa atg gag aag cgt tac cgt cgt tgg att cgc tgg aac gca gcc        336
Glu Glu Met Glu Lys Arg Tyr Arg Arg Trp Ile Arg Trp Asn Ala Ala
            100                 105                 110 atc atg gtt cac cgc gct cag cga cca ggc atc ggc gtc ggc gga cac        384
Ile Met Val His Arg Ala Gln Arg Pro Gly Ile Gly Val Gly Gly His
        115                 120                 125 att tcc act tac gca ggc gca gcc cct ctg tac gaa gtt ggc ttc aac        432
Ile Ser Thr Tyr Ala Gly Ala Ala Pro Leu Tyr Glu Val Gly Phe Asn
    130                 135                 140 cac ttc ttc cgc ggc aag gat cac cca ggc ggc ggc gac cag atc ttc        480
His Phe Phe Arg Gly Lys Asp His Pro Gly Gly Gly Asp Gln Ile Phe
145                 150                 155                 160 ttc cag ggc cac gca tca cca ggt atg tac gca cgt gca ttc atg gag        528
Phe Gln Gly His Ala Ser Pro Gly Met Tyr Ala Arg Ala Phe Met Glu
                165                 170                 175 ggt cgc ctt tct gaa gac gat ctc gat ggc ttc cgt cag gaa gtt tcc        576
Gly Arg Leu Ser Glu Asp Asp Leu Asp Gly Phe Arg Gln Glu Val Ser
            180                 185                 190 cgt gag cag ggt ggc att ccg tcc tac cct cac cca cac ggt atg aag        624
Arg Glu Gln Gly Gly Ile Pro Ser Tyr Pro His Pro His Gly Met Lys
        195                 200                 205 gac ttc tgg gag ttc cca act gtg tcc atg ggt ctt ggc cca atg gat        672
Asp Phe Trp Glu Phe Pro Thr Val Ser Met Gly Leu Gly Pro Met Asp
```

```
                  210                 215                 220
gcc att tac cag gca cgt ttc aac cgc tac ctc gaa aac cgt ggc atc       720
Ala Ile Tyr Gln Ala Arg Phe Asn Arg Tyr Leu Glu Asn Arg Gly Ile
225                 230                 235                 240 aag gac acc tct gac cag cac gtc tgg gcc ttc ctt ggc gac ggc gaa       768
Lys Asp Thr Ser Asp Gln His Val Trp Ala Phe Leu Gly Asp Gly Glu
                245                 250                 255 atg gac gag cca gaa tca cgt ggt ctc atc cag cag gct gca ctg aac       816
Met Asp Glu Pro Glu Ser Arg Gly Leu Ile Gln Gln Ala Ala Leu Asn
                260                 265                 270 aac ctg gac aac ctg acc ttc gtg gtt aac tgc aac ctg cag cgt ctc       864
Asn Leu Asp Asn Leu Thr Phe Val Val Asn Cys Asn Leu Gln Arg Leu
            275                 280                 285 gac gga cct gtc cgc ggt aac acc aag atc atc cag gaa ctc gag tcc       912
Asp Gly Pro Val Arg Gly Asn Thr Lys Ile Ile Gln Glu Leu Glu Ser
        290                 295                 300 ttc ttc cgt ggc gca ggc tgg tct gtg atc aag gtt gtt tgg ggt cgc       960
Phe Phe Arg Gly Ala Gly Trp Ser Val Ile Lys Val Val Trp Gly Arg
305                 310                 315                 320 gag tgg gat gaa ctt ctg gag aag gac cag gat ggt gca ctt gtt gag      1008
Glu Trp Asp Glu Leu Leu Glu Lys Asp Gln Asp Gly Ala Leu Val Glu
                325                 330                 335 atc atg aac aac acc tcc gat ggt gac tac cag acc ttc aag gct aac      1056
Ile Met Asn Asn Thr Ser Asp Gly Asp Tyr Gln Thr Phe Lys Ala Asn
                340                 345                 350 gac ggc gca tat gtt cgt gag cac ttc ttc gga cgt gac cca cgc acc      1104
Asp Gly Ala Tyr Val Arg Glu His Phe Phe Gly Arg Asp Pro Arg Thr
            355                 360                 365 gca aag ctc gtt gag aac atg acc gac gaa gaa atc tgg aag ctg cca      1152
Ala Lys Leu Val Glu Asn Met Thr Asp Glu Glu Ile Trp Lys Leu Pro
370                 375                 380 cgt ggc ggc cac gat tac cgc aag gtt tac gca gcc tac aag cga gct      1200
Arg Gly Gly His Asp Tyr Arg Lys Val Tyr Ala Ala Tyr Lys Arg Ala
385                 390                 395                 400 ctt gag acc aag gat cgc cca acc gtc atc ctt gct cac acc att aag      1248
Leu Glu Thr Lys Asp Arg Pro Thr Val Ile Leu Ala His Thr Ile Lys
                405                 410                 415 ggc tac gga ctc ggc cac aac ttc gaa ggc cgt aac gca acc cac cag      1296
Gly Tyr Gly Leu Gly His Asn Phe Glu Gly Arg Asn Ala Thr His Gln
                420                 425                 430 atg aag aag ctg acg ctt gat gat ctg aag ttg ttc cgc gac aag cag      1344
Met Lys Lys Leu Thr Leu Asp Asp Leu Lys Leu Phe Arg Asp Lys Gln
            435                 440                 445 ggc atc cca atc acc gat gag cag ctg gag aag gat cct tac ctt cct      1392
Gly Ile Pro Ile Thr Asp Glu Gln Leu Glu Lys Asp Pro Tyr Leu Pro
450                 455                 460 cct tac tac cac cca ggt gaa gac gct cct gaa atc aag tac atg aag      1440
Pro Tyr Tyr His Pro Gly Glu Asp Ala Pro Glu Ile Lys Tyr Met Lys
465                 470                 475                 480 gaa cgt cgc gca gcg ctc ggt ggc tac ctg cca gag cgt cgt gag aac      1488
Glu Arg Arg Ala Ala Leu Gly Gly Tyr Leu Pro Glu Arg Arg Glu Asn
                485                 490                 495 tac gat cca att cag gtt cca cca ctg gat aag ctt cgc tct gtc cgt      1536
Tyr Asp Pro Ile Gln Val Pro Pro Leu Asp Lys Leu Arg Ser Val Arg
                500                 505                 510 aag ggc tcc ggc aag cag cag atc gct acc act atg gcg act gtt cgt      1584
Lys Gly Ser Gly Lys Gln Gln Ile Ala Thr Thr Met Ala Thr Val Arg
            515                 520                 525 acc ttc aag gaa ctg atg cgc gat aag ggc ttg gct gat cgc ctt gtc      1632
```

|                                                                                                   |      |
|---------------------------------------------------------------------------------------------------|------|
| Thr Phe Lys Glu Leu Met Arg Asp Lys Gly Leu Ala Asp Arg Leu Val<br>530              535              540                |      |
| cca atc att cct gat gag gca cgt acc ttc ggt ctt gac tct tgg ttc<br>Pro Ile Ile Pro Asp Glu Ala Arg Thr Phe Gly Leu Asp Ser Trp Phe<br>545              550              555              560 | 1680 |
| cca acc ttg aag atc tac aac ccg cac ggt cag aac tac gtg cct gtt<br>Pro Thr Leu Lys Ile Tyr Asn Pro His Gly Gln Asn Tyr Val Pro Val<br>                 565              570              575    | 1728 |
| gac cac gac ctg atg ctc tcc tac cgt gag gca cct gaa gga cag atc<br>Asp His Asp Leu Met Leu Ser Tyr Arg Glu Ala Pro Glu Gly Gln Ile<br>                 580              585              590    | 1776 |
| ctg cac gaa ggc atc aac gag gct ggt tcc gtg gca tcg ttc atc gct<br>Leu His Glu Gly Ile Asn Glu Ala Gly Ser Val Ala Ser Phe Ile Ala<br>                 595              600              605    | 1824 |
| gcg ggt acc tcc tac gcc acc cac ggc aag gcc atg att ccg ctg tac<br>Ala Gly Thr Ser Tyr Ala Thr His Gly Lys Ala Met Ile Pro Leu Tyr<br>610              615              620                | 1872 |
| atc ttc tac tcg atg ttc gga ttc cag cgc acc ggt gac tcc atc tgg<br>Ile Phe Tyr Ser Met Phe Gly Phe Gln Arg Thr Gly Asp Ser Ile Trp<br>625              630              635              640 | 1920 |
| gca gca gcc gat cag atg gca cgt ggc ttc ctc ttg ggc gct acc gca<br>Ala Ala Ala Asp Gln Met Ala Arg Gly Phe Leu Leu Gly Ala Thr Ala<br>                 645              650              655    | 1968 |
| ggt cgc acc acc ctg acc ggt gaa ggc ctc cag cac atg gat gga cac<br>Gly Arg Thr Thr Leu Thr Gly Glu Gly Leu Gln His Met Asp Gly His<br>                 660              665              670    | 2016 |
| tcc cct gtc ttg gct tcc acc aac gag ggt gtc gag acc tac gac cca<br>Ser Pro Val Leu Ala Ser Thr Asn Glu Gly Val Glu Thr Tyr Asp Pro<br>                 675              680              685    | 2064 |
| tcc ttt gcg tac gag atc gca cac ctg gtt cac cgt ggc atc gac cgc<br>Ser Phe Ala Tyr Glu Ile Ala His Leu Val His Arg Gly Ile Asp Arg<br>690              695              700                | 2112 |
| atg tac ggc cca ggc aag ggt gaa gat gtt atc tac tac atc acc atc<br>Met Tyr Gly Pro Gly Lys Gly Glu Asp Val Ile Tyr Tyr Ile Thr Ile<br>705              710              715              720 | 2160 |
| tac aac gag cca acc cca cag cca gct gag cca gaa gga ctg gac gta<br>Tyr Asn Glu Pro Thr Pro Gln Pro Ala Glu Pro Glu Gly Leu Asp Val<br>                 725              730              735    | 2208 |
| gaa ggc ctg cac aag ggc atc tac ctc tac tcc cgc ggt gaa ggc acc<br>Glu Gly Leu His Lys Gly Ile Tyr Leu Tyr Ser Arg Gly Glu Gly Thr<br>                 740              745              750    | 2256 |
| ggc cat gag gca aac atc ttg gct tcc ggt gtt ggt atg cag tgg gct<br>Gly His Glu Ala Asn Ile Leu Ala Ser Gly Val Gly Met Gln Trp Ala<br>                 755              760              765    | 2304 |
| ctc aag gct gca tcc atc ctt gag gct gac tac gga gtt cgt gcc aac<br>Leu Lys Ala Ala Ser Ile Leu Glu Ala Asp Tyr Gly Val Arg Ala Asn<br>770              775              780                | 2352 |
| att tac tcc gct act tct tgg gtt aac ttg gct cgc gat ggc gct gct<br>Ile Tyr Ser Ala Thr Ser Trp Val Asn Leu Ala Arg Asp Gly Ala Ala<br>785              790              795              800 | 2400 |
| cgt aac aag gca cag ctg cgc aac cca ggt gca gat gct ggc gag gca<br>Arg Asn Lys Ala Gln Leu Arg Asn Pro Gly Ala Asp Ala Gly Glu Ala<br>                 805              810              815    | 2448 |
| ttc gta acc acc cag ctg aag cag acc tcc ggc cca tac gtt gca gtg<br>Phe Val Thr Thr Gln Leu Lys Gln Thr Ser Gly Pro Tyr Val Ala Val<br>                 820              825              830    | 2496 |
| tct gac ttc tcc act gat ctg cca aac cag atc cgt gaa tgg gtc cca<br>Ser Asp Phe Ser Thr Asp Leu Pro Asn Gln Ile Arg Glu Trp Val Pro<br>835              840              845                | 2544 |

-continued

```
ggc gac tac acc gtt ctc ggt gca gat ggc ttc ggt ttc tct gat acc   2592
Gly Asp Tyr Thr Val Leu Gly Ala Asp Gly Phe Gly Phe Ser Asp Thr
    850                 855                 860 cgc cca gct gct cgt cgc ttc ttc aac atc gac gct gag tcc att gtt   2640
Arg Pro Ala Ala Arg Arg Phe Phe Asn Ile Asp Ala Glu Ser Ile Val
865                 870                 875                 880 gtt gca gtg ctg aac tcc ctg gca cgc gaa ggc aag atc gac gtc tcc   2688
Val Ala Val Leu Asn Ser Leu Ala Arg Glu Gly Lys Ile Asp Val Ser
                885                 890                 895 gtt gct gct cag gct gct gag aag ttc aag ttg gat gat cct acg agt   2736
Val Ala Ala Gln Ala Ala Glu Lys Phe Lys Leu Asp Asp Pro Thr Ser
            900                 905                 910 gtt tcc gta gat cca aac gct cct gag gaa                           2766
Val Ser Val Asp Pro Asn Ala Pro Glu Glu
        915                 920
```

<210> SEQ ID NO 32
<211> LENGTH: 922
<212> TYPE: PRT
<213> ORGANISM: Brevibacterium lactofermentum ATCC13869

<400> SEQUENCE: 32

```
Met Ala Asp Gln Ala Lys Leu Gly Gly Lys Pro Ser Asp Asp Ser Asn
1               5                   10                  15

Phe Ala Met Ile Arg Asp Gly Val Ala Ser Tyr Leu Asn Asp Ser Asp
            20                  25                  30

Pro Glu Glu Thr Asn Glu Trp Met Asp Ser Leu Asp Gly Leu Leu Gln
        35                  40                  45

Glu Ser Ser Pro Glu Arg Ala Arg Tyr Leu Met Leu Arg Leu Leu Glu
    50                  55                  60

Arg Ala Ser Ala Lys Arg Val Ser Leu Pro Pro Met Thr Ser Thr Asp
65                  70                  75                  80

Tyr Val Asn Thr Ile Pro Thr Ser Met Glu Pro Glu Phe Pro Gly Asp
                85                  90                  95

Glu Glu Met Glu Lys Arg Tyr Arg Arg Trp Ile Arg Trp Asn Ala Ala
            100                 105                 110

Ile Met Val His Arg Ala Gln Arg Pro Gly Ile Gly Val Gly Gly His
        115                 120                 125

Ile Ser Thr Tyr Ala Gly Ala Ala Pro Leu Tyr Glu Val Gly Phe Asn
    130                 135                 140

His Phe Phe Arg Gly Lys Asp His Pro Gly Gly Gly Asp Gln Ile Phe
145                 150                 155                 160

Phe Gln Gly His Ala Ser Pro Gly Met Tyr Ala Arg Ala Phe Met Glu
                165                 170                 175

Gly Arg Leu Ser Glu Asp Asp Leu Asp Gly Phe Arg Gln Glu Val Ser
            180                 185                 190

Arg Glu Gln Gly Gly Ile Pro Ser Tyr Pro His Pro His Gly Met Lys
        195                 200                 205

Asp Phe Trp Glu Phe Pro Thr Val Ser Met Gly Leu Gly Pro Met Asp
    210                 215                 220

Ala Ile Tyr Gln Ala Arg Phe Asn Arg Tyr Leu Glu Asn Arg Gly Ile
225                 230                 235                 240

Lys Asp Thr Ser Asp Gln His Val Trp Ala Phe Leu Gly Asp Gly Glu
                245                 250                 255

Met Asp Glu Pro Glu Ser Arg Gly Leu Ile Gln Gln Ala Ala Leu Asn
            260                 265                 270
```

-continued

```
Asn Leu Asp Asn Leu Thr Phe Val Val Asn Cys Asn Leu Gln Arg Leu
            275                 280                 285
Asp Gly Pro Val Arg Gly Asn Thr Lys Ile Ile Gln Glu Leu Glu Ser
        290                 295                 300
Phe Phe Arg Gly Ala Gly Trp Ser Val Ile Lys Val Val Trp Gly Arg
305                 310                 315                 320
Glu Trp Asp Glu Leu Leu Glu Lys Asp Gln Asp Gly Ala Leu Val Glu
                325                 330                 335
Ile Met Asn Asn Thr Ser Asp Gly Asp Tyr Gln Thr Phe Lys Ala Asn
            340                 345                 350
Asp Gly Ala Tyr Val Arg Glu His Phe Gly Arg Asp Pro Arg Thr
        355                 360                 365
Ala Lys Leu Val Glu Asn Met Thr Asp Glu Ile Trp Lys Leu Pro
    370                 375                 380
Arg Gly Gly His Asp Tyr Arg Lys Val Tyr Ala Ala Tyr Lys Arg Ala
385                 390                 395                 400
Leu Glu Thr Lys Asp Arg Pro Thr Val Ile Leu Ala His Thr Ile Lys
                405                 410                 415
Gly Tyr Gly Leu Gly His Asn Phe Glu Gly Arg Asn Ala Thr His Gln
            420                 425                 430
Met Lys Lys Leu Thr Leu Asp Asp Leu Lys Leu Phe Arg Asp Lys Gln
        435                 440                 445
Gly Ile Pro Ile Thr Asp Glu Gln Leu Glu Lys Asp Pro Tyr Leu Pro
    450                 455                 460
Pro Tyr Tyr His Pro Gly Glu Asp Ala Pro Glu Ile Lys Tyr Met Lys
465                 470                 475                 480
Glu Arg Arg Ala Ala Leu Gly Gly Tyr Leu Pro Glu Arg Arg Glu Asn
                485                 490                 495
Tyr Asp Pro Ile Gln Val Pro Pro Leu Asp Lys Leu Arg Ser Val Arg
            500                 505                 510
Lys Gly Ser Gly Lys Gln Gln Ile Ala Thr Thr Met Ala Thr Val Arg
        515                 520                 525
Thr Phe Lys Glu Leu Met Arg Asp Lys Gly Leu Ala Asp Arg Leu Val
    530                 535                 540
Pro Ile Ile Pro Asp Glu Ala Arg Thr Phe Gly Leu Asp Ser Trp Phe
545                 550                 555                 560
Pro Thr Leu Lys Ile Tyr Asn Pro His Gly Gln Asn Tyr Val Pro Val
                565                 570                 575
Asp His Asp Leu Met Leu Ser Tyr Arg Glu Ala Pro Glu Gly Gln Ile
            580                 585                 590
Leu His Glu Gly Ile Asn Glu Ala Gly Ser Val Ala Ser Phe Ile Ala
        595                 600                 605
Ala Gly Thr Ser Tyr Ala Thr His Gly Lys Ala Met Ile Pro Leu Tyr
    610                 615                 620
Ile Phe Tyr Ser Met Phe Gly Phe Gln Arg Thr Gly Asp Ser Ile Trp
625                 630                 635                 640
Ala Ala Ala Asp Gln Met Ala Arg Gly Phe Leu Leu Gly Ala Thr Ala
                645                 650                 655
Gly Arg Thr Thr Leu Thr Gly Glu Gly Leu Gln His Met Asp Gly His
            660                 665                 670
Ser Pro Val Leu Ala Ser Thr Asn Glu Gly Val Glu Thr Tyr Asp Pro
        675                 680                 685
Ser Phe Ala Tyr Glu Ile Ala His Leu Val His Arg Gly Ile Asp Arg
```

```
                    690            695            700
Met Tyr Gly Pro Gly Lys Gly Glu Asp Val Ile Tyr Tyr Ile Thr Ile
705                     710                        715                720

Tyr Asn Glu Pro Thr Pro Gln Pro Ala Glu Pro Glu Gly Leu Asp Val
                725                 730                 735

Glu Gly Leu His Lys Gly Ile Tyr Leu Tyr Ser Arg Gly Glu Gly Thr
            740                 745                 750

Gly His Glu Ala Asn Ile Leu Ala Ser Gly Val Gly Met Gln Trp Ala
        755                 760                 765

Leu Lys Ala Ala Ser Ile Leu Glu Ala Asp Tyr Gly Val Arg Ala Asn
770                 775                 780

Ile Tyr Ser Ala Thr Ser Trp Val Asn Leu Ala Arg Asp Gly Ala Ala
785                 790                 795                 800

Arg Asn Lys Ala Gln Leu Arg Asn Pro Gly Ala Asp Ala Gly Glu Ala
                805                 810                 815

Phe Val Thr Thr Gln Leu Lys Gln Thr Ser Gly Pro Tyr Val Ala Val
            820                 825                 830

Ser Asp Phe Ser Thr Asp Leu Pro Asn Gln Ile Arg Glu Trp Val Pro
        835                 840                 845

Gly Asp Tyr Thr Val Leu Gly Ala Asp Gly Phe Gly Phe Ser Asp Thr
850                 855                 860

Arg Pro Ala Ala Arg Arg Phe Phe Asn Ile Asp Ala Glu Ser Ile Val
865                 870                 875                 880

Val Ala Val Leu Asn Ser Leu Ala Arg Glu Gly Lys Ile Asp Val Ser
                885                 890                 895

Val Ala Ala Gln Ala Ala Glu Lys Phe Lys Leu Asp Asp Pro Thr Ser
            900                 905                 910

Val Ser Val Asp Pro Asn Ala Pro Glu Glu
        915                 920

<210> SEQ ID NO 33
<211> LENGTH: 8556
<212> TYPE: DNA
<213> ORGANISM: Brevibacterium lactofermentum ATCC13869
<220> FEATURE:
<221> NAME/KEY: CDS
<222> LOCATION: (2360)..(5125)
<223> OTHER INFORMATION:

<400> SEQUENCE: 33
tcacgttacg gcgatcaaca ccgcaaccac tacgagaaga tctccaaacg agaccaagag      60
cgcttctaag cccgtctcat tttgcacctg ccattctgtg aggatatggc aggtgctttt     120
tcatgccact atcttggggt tctcggtatt agatcttctg ataaaaaccc gatagttttc     180
ttgcgctaga cactaattac ggcaccgctt aagcatggtc gtgacacgta aaacctgact     240
taggccattt tgatgtggtg tagatcatat tgacgtcaat gaatgaagtg actaactccg     300
ccgaatccac atcgtctaaa aggcctgggc gaccacgtaa agacgggcac gacgagaaga     360
tcatcgacgc aactttacgg ctcatcgaca gcaatcgtcc cgtcacggtc aatgcagttg     420
tcaaagaaag cggagtggca cgtgcagcgg tttatcgacg ctggcccagg ctagtggatc     480
tagtagcgga agctttagat gccgggcgag ctccagttga aatagatacc caggggaca     540 tcaaagagac cttgattgat gggctgttta caaatcaggc gaaaaccact ggagtctcct     600
atcctcgtca gcgatttcgc aaacggctcg agttggtgat gtcagatcaa gaattacagc     660
tcgcctaatg gaattcacat gtgaagagac gtcgagaagc aaatattcgc gcgctgcaag     720
```

-continued

```
tcgcgcaaga aaaaggccaa atccgggcgg atctagacat cgaggcgtgc ctcgatgcaa     780
tccttggggt gttttattac caatcggtcg cgcgtggagt aaatttcacc gaccaaggta     840
caacgcaacg atgcagagaa gccttggagg tgatctggca tggaatggaa ccttaaattc     900
aggttctgac gaggtgcgaa gcaagttgtc gcgcgccgca cctcagtatc cggatcaact     960
taatttcgaa gtgctgggtt ttctcgcgca tacccaatgc gtaccgatgt gcccatgagc    1020
gaaaaacagg ccacgataag tttcttaaaa cttatcgtgg cctgcttcta tatttgtgcg    1080
ccctgacggg ctcgaaccgc cgacctgctg ggtgtaaacc agctgctctt ccagctgagc    1140
taaaggcgcg cacgtgcttt tctagaacca ccttggtggc ctcgaaagca acgagtgaaa    1200
tactaacaca caatctccac agacctaaaa tcgctgctca ggccgtggaa attagcgatt    1260
gttaaggctt cttgtttcca cgctggacga ggcaagaacc ttgccaatta ccgagacgtt    1320
ccgccttggt ctgcacgaga cctgccagtt gtgctgattc agagataact ccaggagcca    1380
gggctccttc tttaccaatg ccaggagtca acacccagat acgaccattc tcagcgaggg    1440
agcggatgga atccacaagt ccgtcgacga gatcgccgtc atcctcgcgc accagagca    1500
gcacgacatc gcacagctcg tcggtttctt catcgagtag ttcctcaccg attgcatctt    1560
cgatggactc gctgatcagc gtgtcggaat cttcatccca tccaatttct gaacgatat    1620
gacccgattg aatgccgagt agttgagcat aatcctgggc accttgcttg actgcgcccg    1680
gagcgtcggc cactttaata atcctcctcg tgtgggcccc gatgtgtttt tcgattacat    1740
ggattcaaca tgaaaccgcg gggctattga tatatccgaa ttgcacatta ccgtccaacc    1800
ggtactttga accaccttc cctggaattt tttccttttc ctccccttt acgctcaaga     1860
atcaatgaat tcaatcactg gccagcgatt aactttcga gttttcagtc ttggatttcc    1920
acaattctct tcaaaataat ggtggctaga tttttcatca accctcacc aaaaggacat     1980
cagacctgta gttttatgcg attcgcgtca acgtgagag aaacatcaca tctcacggga     2040
aactacccga taattctttg caaaactttg caaagggtaa tgaacatgca gctagtttcc    2100
gtagaaatgt tctttaaaaa atccacaaca attgccagga agcacaccga ttgatggata    2160
cctgaaatcc cagtgagcgc accactcccc ttacgtcaca gtctgtaaaa caaatcttcg    2220
gtgttgcgta tccttgttaa taacttatgc gttgacccat tcgtgcactt cggtgtgcca    2280
caattaggta cgaccaagaa tgggaccggg aaaccgggac gtataaacga aataaaacat    2340
tccaacagga ggtgtggaa atg gcc gat caa gca aaa ctt ggt ggt aag ccc    2392
                      Met Ala Asp Gln Ala Lys Leu Gly Gly Lys Pro
                       1               5                   10
tcg gat gac tct aac ttc gcg atg atc cgc gat ggc gtg gca tct tat    2440
Ser Asp Asp Ser Asn Phe Ala Met Ile Arg Asp Gly Val Ala Ser Tyr
         15                  20                  25
ttg aac gac tca gat ccg gag gag acc aac gag tgg atg gat tca ctc    2488
Leu Asn Asp Ser Asp Pro Glu Glu Thr Asn Glu Trp Met Asp Ser Leu
     30                  35                  40
gac gga tta ctc cag gag tct tct cca gaa cgt gct cgt tac ctc atg    2536
Asp Gly Leu Leu Gln Glu Ser Ser Pro Glu Arg Ala Arg Tyr Leu Met
 45                  50                  55
ctt cgt ttg ctt gag cgt gca tct gca aag cgc gta tct ctt ccc cca    2584
Leu Arg Leu Leu Glu Arg Ala Ser Ala Lys Arg Val Ser Leu Pro Pro
 60                  65                  70                  75
atg acg tca acc gac tac gtc aac acc att cca acc tct atg gaa cct    2632
Met Thr Ser Thr Asp Tyr Val Asn Thr Ile Pro Thr Ser Met Glu Pro
             80                  85                  90
```

```
                                                    -continued gaa ttc cca ggc gat gag gaa atg gag aag cgt tac cgt cgt tgg att        2680
Glu Phe Pro Gly Asp Glu Glu Met Glu Lys Arg Tyr Arg Arg Trp Ile
             95                 100                 105 cgc tgg aac gca gcc atc atg gtt cac cgc gct cag cga cca ggc atc        2728
Arg Trp Asn Ala Ala Ile Met Val His Arg Ala Gln Arg Pro Gly Ile
    110                 115                 120 ggc gtc ggc gga cac att tcc act tac gca ggc gca gcc cct ctg tac        2776
Gly Val Gly Gly His Ile Ser Thr Tyr Ala Gly Ala Ala Pro Leu Tyr
125                 130                 135 gaa gtt ggc ttc aac cac ttc ttc cgc ggc aag gat cac cca ggc ggc        2824
Glu Val Gly Phe Asn His Phe Phe Arg Gly Lys Asp His Pro Gly Gly
140                 145                 150                 155 ggc gac cag atc ttc ttc cag ggc cac gca tca cca ggt atg tac gca        2872
Gly Asp Gln Ile Phe Phe Gln Gly His Ala Ser Pro Gly Met Tyr Ala
                160                 165                 170 cgt gca ttc atg gag ggt cgc ctt tct gaa gac gat ctc gat ggc ttc        2920
Arg Ala Phe Met Glu Gly Arg Leu Ser Glu Asp Asp Leu Asp Gly Phe
            175                 180                 185 cgt cag gaa gtt tcc cgt gag cag ggt ggc att ccg tcc tac cct cac        2968
Arg Gln Glu Val Ser Arg Glu Gln Gly Gly Ile Pro Ser Tyr Pro His
        190                 195                 200 cca cac ggt atg aag gac ttc tgg gag ttc cca act gtg tcc atg ggt        3016
Pro His Gly Met Lys Asp Phe Trp Glu Phe Pro Thr Val Ser Met Gly
    205                 210                 215 ctt ggc cca atg gat gcc att tac cag gca cgt ttc aac cgc tac ctc        3064
Leu Gly Pro Met Asp Ala Ile Tyr Gln Ala Arg Phe Asn Arg Tyr Leu
220                 225                 230                 235 gaa aac cgt ggc atc aag gac acc tct gac cag cac gtc tgg gcc ttc        3112
Glu Asn Arg Gly Ile Lys Asp Thr Ser Asp Gln His Val Trp Ala Phe
                240                 245                 250 ctt ggc gac ggc gaa atg gac gag cca gaa tca cgt ggt ctc atc cag        3160
Leu Gly Asp Gly Glu Met Asp Glu Pro Glu Ser Arg Gly Leu Ile Gln
            255                 260                 265 cag gct gca ctg aac aac ctg gac aac ctg acc ttc gtg gtt aac tgc        3208
Gln Ala Ala Leu Asn Asn Leu Asp Asn Leu Thr Phe Val Val Asn Cys
        270                 275                 280 aac ctg cag cgt ctc gac gga cct gtc cgc ggt aac acc aag atc atc        3256
Asn Leu Gln Arg Leu Asp Gly Pro Val Arg Gly Asn Thr Lys Ile Ile
    285                 290                 295 cag gaa ctc gag tcc ttc ttc cgt ggc gca ggc tgg tct gtg atc aag        3304
Gln Glu Leu Glu Ser Phe Phe Arg Gly Ala Gly Trp Ser Val Ile Lys
300                 305                 310                 315 gtt gtt tgg ggt cgc gag tgg gat gaa ctt ctg gag aag gac cag gat        3352
Val Val Trp Gly Arg Glu Trp Asp Glu Leu Leu Glu Lys Asp Gln Asp
                320                 325                 330 ggt gca ctt gtt gag atc atg aac aac acc tcc gat ggt gac tac cag        3400
Gly Ala Leu Val Glu Ile Met Asn Asn Thr Ser Asp Gly Asp Tyr Gln
            335                 340                 345 acc ttc aag gct aac gac ggc gca tat gtt cgt gag cac ttc ttc gga        3448
Thr Phe Lys Ala Asn Asp Gly Ala Tyr Val Arg Glu His Phe Phe Gly
        350                 355                 360 cgt gac cca cgc acc gca aag ctc gtt gag aac atg acc gac gaa gaa        3496
Arg Asp Pro Arg Thr Ala Lys Leu Val Glu Asn Met Thr Asp Glu Glu
    365                 370                 375 atc tgg aag ctg cca cgt ggc ggc cac gat tac cgc aag gtt tac gca        3544
Ile Trp Lys Leu Pro Arg Gly Gly His Asp Tyr Arg Lys Val Tyr Ala
380                 385                 390                 395 gcc tac aag cga gct ctt gag acc aag gat cgc cca acc gtc atc ctt        3592
Ala Tyr Lys Arg Ala Leu Glu Thr Lys Asp Arg Pro Thr Val Ile Leu
                400                 405                 410
```

| | |
|---|---|
| gct cac acc att aag ggc tac gga ctc ggc cac aac ttc gaa ggc cgt<br>Ala His Thr Ile Lys Gly Tyr Gly Leu Gly His Asn Phe Glu Gly Arg<br>              415                         420                        425 | 3640 |
| aac gca acc cac cag atg aag aag ctg acg ctt gat gat ctg aag ttg<br>Asn Ala Thr His Gln Met Lys Lys Leu Thr Leu Asp Asp Leu Lys Leu<br>              430                         435                        440 | 3688 |
| ttc cgc gac aag cag ggc atc cca atc acc gat gag cag ctg gag aag<br>Phe Arg Asp Lys Gln Gly Ile Pro Ile Thr Asp Glu Gln Leu Glu Lys<br>445                         450                         455 | 3736 |
| gat cct tac ctt cct cct tac tac cac cca ggt gaa gac gct cct gaa<br>Asp Pro Tyr Leu Pro Pro Tyr Tyr His Pro Gly Glu Asp Ala Pro Glu<br>460                       465                         470                   475 | 3784 |
| atc aag tac atg aag gaa cgt cgc gca gcg ctc ggt ggc tac ctg cca<br>Ile Lys Tyr Met Lys Glu Arg Arg Ala Ala Leu Gly Gly Tyr Leu Pro<br>                  480                         485                        490 | 3832 |
| gag cgt cgt gag aac tac gat cca att cag gtt cca cca ctg gat aag<br>Glu Arg Arg Glu Asn Tyr Asp Pro Ile Gln Val Pro Pro Leu Asp Lys<br>              495                         500                        505 | 3880 |
| ctt cgc tct gtc cgt aag ggc tcc ggc aag cag cag atc gct acc act<br>Leu Arg Ser Val Arg Lys Gly Ser Gly Lys Gln Gln Ile Ala Thr Thr<br>510                         515                         520 | 3928 |
| atg gcg act gtt cgt acc ttc aag gaa ctg atg cgc gat aag ggc ttg<br>Met Ala Thr Val Arg Thr Phe Lys Glu Leu Met Arg Asp Lys Gly Leu<br>              525                         530                        535 | 3976 |
| gct gat cgc ctt gtc cca atc att cct gat gag gca cgt acc ttc ggt<br>Ala Asp Arg Leu Val Pro Ile Ile Pro Asp Glu Ala Arg Thr Phe Gly<br>540                       545                         550                   555 | 4024 |
| ctt gac tct tgg ttc cca acc ttg aag atc tac aac ccg cac ggt cag<br>Leu Asp Ser Trp Phe Pro Thr Leu Lys Ile Tyr Asn Pro His Gly Gln<br>                  560                         565                        570 | 4072 |
| aac tac gtg cct gtt gac cac gac ctg atg ctc tcc tac cgt gag gca<br>Asn Tyr Val Pro Val Asp His Asp Leu Met Leu Ser Tyr Arg Glu Ala<br>              575                         580                        585 | 4120 |
| cct gaa gga cag atc ctg cac gaa ggc atc aac gag gct ggt tcc gtg<br>Pro Glu Gly Gln Ile Leu His Glu Gly Ile Asn Glu Ala Gly Ser Val<br>                  590                         595                        600 | 4168 |
| gca tcg ttc atc gct gcg ggt acc tcc tac gcc acc cac ggc aag gcc<br>Ala Ser Phe Ile Ala Ala Gly Thr Ser Tyr Ala Thr His Gly Lys Ala<br>605                         610                         615 | 4216 |
| atg att ccg ctg tac atc ttc tac tcg atg ttc gga ttc cag cgc acc<br>Met Ile Pro Leu Tyr Ile Phe Tyr Ser Met Phe Gly Phe Gln Arg Thr<br>620                         625                         630                   635 | 4264 |
| ggt gac tcc atc tgg gca gca gcc gat cag atg gca cgt ggc ttc ctc<br>Gly Asp Ser Ile Trp Ala Ala Ala Asp Gln Met Ala Arg Gly Phe Leu<br>                  640                         645                        650 | 4312 |
| ttg ggc gct acc gca ggt cgc acc acc ctg acc ggt gaa ggc ctc cag<br>Leu Gly Ala Thr Ala Gly Arg Thr Thr Leu Thr Gly Glu Gly Leu Gln<br>              655                         660                        665 | 4360 |
| cac atg gat gga cac tcc cct gtc ttg gct tcc acc aac gag ggt gtc<br>His Met Asp Gly His Ser Pro Val Leu Ala Ser Thr Asn Glu Gly Val<br>670                         675                         680 | 4408 |
| gag acc tac gac cca tcc ttt gcg tac gag atc gca cac ctg gtt cac<br>Glu Thr Tyr Asp Pro Ser Phe Ala Tyr Glu Ile Ala His Leu Val His<br>685                         690                         695 | 4456 |
| cgt ggc atc gac cgc atg tac ggc cca ggc aag ggt gaa gat gtt atc<br>Arg Gly Ile Asp Arg Met Tyr Gly Pro Gly Lys Gly Glu Asp Val Ile<br>700                         705                         710                   715 | 4504 |
| tac tac atc acc atc tac aac gag cca acc cca cag cca gct gag cca<br>Tyr Tyr Ile Thr Ile Tyr Asn Glu Pro Thr Pro Gln Pro Ala Glu Pro | 4552 |

```
                720                 725                 730
gaa gga ctg gac gta gaa ggc ctg cac aag ggc atc tac ctc tac tcc       4600
Glu Gly Leu Asp Val Glu Gly Leu His Lys Gly Ile Tyr Leu Tyr Ser
            735                 740                 745
cgc ggt gaa ggc acc ggc cat gag gca aac atc ttg gct tcc ggt gtt       4648
Arg Gly Glu Gly Thr Gly His Glu Ala Asn Ile Leu Ala Ser Gly Val
        750                 755                 760
ggt atg cag tgg gct ctc aag gct gca tcc atc ctt gag gct gac tac       4696
Gly Met Gln Trp Ala Leu Lys Ala Ala Ser Ile Leu Glu Ala Asp Tyr
    765                 770                 775
gga gtt cgt gcc aac att tac tcc gct act tct tgg gtt aac ttg gct       4744
Gly Val Arg Ala Asn Ile Tyr Ser Ala Thr Ser Trp Val Asn Leu Ala
780                 785                 790                 795
cgc gat ggc gct gct cgt aac aag gca cag ctg cgc aac cca ggt gca       4792
Arg Asp Gly Ala Ala Arg Asn Lys Ala Gln Leu Arg Asn Pro Gly Ala
                800                 805                 810
gat gct ggc gag gca ttc gta acc acc cag ctg aag cag acc tcc ggc       4840
Asp Ala Gly Glu Ala Phe Val Thr Thr Gln Leu Lys Gln Thr Ser Gly
            815                 820                 825
cca tac gtt gca gtg tct gac ttc tcc act gat ctg cca aac cag atc       4888
Pro Tyr Val Ala Val Ser Asp Phe Ser Thr Asp Leu Pro Asn Gln Ile
        830                 835                 840
cgt gaa tgg gtc cca ggc gac tac acc gtt ctc ggt gca gat ggc ttc       4936
Arg Glu Trp Val Pro Gly Asp Tyr Thr Val Leu Gly Ala Asp Gly Phe
    845                 850                 855
ggt ttc tct gat acc cgc cca gct gct cgt cgc ttc ttc aac atc gac       4984
Gly Phe Ser Asp Thr Arg Pro Ala Ala Arg Arg Phe Phe Asn Ile Asp
860                 865                 870                 875
gct gag tcc att gtt gtt gca gtg ctg aac tcc ctg gca cgc gaa ggc       5032
Ala Glu Ser Ile Val Val Ala Val Leu Asn Ser Leu Ala Arg Glu Gly
                880                 885                 890
aag atc gac gtc tcc gtt gct gct cag gct gct gag aag ttc aag ttg       5080
Lys Ile Asp Val Ser Val Ala Ala Gln Ala Ala Glu Lys Phe Lys Leu
            895                 900                 905
gat gat cct acg agt gtt tcc gta gat cca aac gct cct gag gaa           5125
Asp Asp Pro Thr Ser Val Ser Val Asp Pro Asn Ala Pro Glu Glu
        910                 915                 920
taaatcacct caagggacag ataaatcccg ccgccagacg ttagtctggc ggcgggattc     5185
gtcgtaaagc aagctctttt tagccgagaa acgccttgtc agacaatgtt gcgcccttga     5245
tattggcgaa ctcctgcagc aaatcgcgca cagtcaactt cgacttggta gcctgatctg     5305
cctggtagac aatctggcct tcatgcatca tgatcaggcg attgcccagg cgaattgcct     5365
gttccatgtt gtgcgtgacc ataagcgtag tcagagttcc atctgccacg atcttttcgg     5425
tcaaggtggt cacaagctct gcacgctgtg gatcaagcgc tgcggtgtgc tcatccaaca     5485
gcatgatttt aggttgagta aaaccagcca tcagcaggga caatgcctga cgctgaccgc     5545
cagagagcaa accaactttg gcagtgagcc tgttttccag acccagctca aggcgctcaa     5605
gttcctgctt gaattgctca cggcgcttcg aggtcagtgc aaagcccaat ccacggcgct     5665
tgccgcgcag caacgcgatg ccagattcct cttcaatggt gagattcggc gcggtgcctg     5725
ccaaaggatc ctgaaaaacg cggccgatgt agcgggcacg cttgtgctct gacatcttgt     5785
ttaccttgtt gccgtcgatg gaaatctcgc cggaatcaac aagcaaacgg ccagaaacag     5845
cgttgagcag ggtggattta cccgcaccgt tagaaccgat gacggtgaca aaatcgccct     5905
cagccatatc gagtttgagc tgctgcaacg cgcggcgctc attcacagtg ccggggaaga     5965
aggttttgga aattccgttg atggataaca tgtcttaagc ctccactgct actggttgct     6025
```

-continued

```
taggcttcgg tgccttggag aacttcgcac gccacctcgg cagcagcatg gcgacaacca    6085
ccaagatcgc agaaattgcc ttcatatcgt tggggtcaag gccaacgcgc agtgctgcga    6145
aaatgatcag gcggtacgcg atggcaccga cgatgacagc caacacagcc aaccacacgc    6205
gacgctgacc gaagatggcc tggccccaaa ataaccgatg cgagaccgat cacgatgagg    6265 ccaatacccca tcgaaatatc tgcgaagccc tggtactgag cgatgagtgc accggcaaga    6325
ccaacagaac cattggacag ggagatggtg aggattttgg tgaaatccgt tgaaacacca    6385
aaggactgca ccatcggccc gttgtcgccg gtggatcgca cgacagtcc gatatcagtg    6445 ttgaggaacc agatgacgat gagtcccaaa atcccactg caacggcgag gatcgccggg    6505
cctgcccatg tgccgaggag gccggcgtcg cgaagcgggg tgaagaggtt atcggtgcgc    6565
aacaatggca cgttcgcgcc acccatgatg cgcaagttaa ccgaccacaa cgcaatcatg    6625
gtcaaaatac ctgcgagcaa accatcgatc ttgcccttgg tgtgcagcaa accggtgatc    6685
atgccagcga taaagccagt aacgaaacca gcggcagtag ccataagagg aggccagcca    6745
gacataagag ctgtcgcagc tgttgccgcg ccagtggtca ggctgccgtc aacggtgagg    6805
tcgggaaagt tgagcacacg gaacgtcaaa tagacgccca atgcgacaac tccgtacaac    6865
aatccgaact caaaagcgcc gatcatacgc gttcggcctt atccaaaatc tcttgaggga    6925
tctccacgcc ctggcgctct gctgcatctt cgttgatcac gtaggtgaac tcagttgcag    6985
tctccacagg catggttgct gggtcttcgc cgtcctgcag aatacgcaga gccatctcgc    7045
cagtctggcg gccaagctcg gtgtaatcga tacccagggt tgccagtgcg ccaccctcaa    7105
cagtgccgga ctcagcaccg atcacaggga tctgcttctg ctcagcaacc tgaaccagag    7165
aagaaatacc ggaaacaacc atgttgtcag ttggaacgta gatgacatca acatcgccga    7225
gagcttcaac agcctgctga atctcgttca cggtagtgac agtctgagta ttaacggaca    7285
gccccagtgg ctcagcagcc ttggtgacct catcgacctg cacctgagag ttgacctcac    7345
cagacgcgta gacgatgccg atggactttg cgtcaggaac cagctgctgc aaaagctcca    7405
actgctgctc aatcggtgcg atatcagaag taccggtgac gtttccgcca ggtgcttcat    7465
tagaatccac cagctctgcc gacactgcat cggtaactgc ggtgaacagg actgggatat    7525
cagtgatatt ctgcgcagtt gcctgtgctg ctggagttgc aacagccaac acgagatcca    7585
aattgtcaga agcgaactgc tgagaaatag tcagtgcagt gccctgctcg ccgttagcgt    7645
tttgctcatc aaaggtgacg tcaacgcctg cctcttcaaa agcttccttg aaaccagtgg    7705
tcgctgcatc aagtgcaggg tgctgaacaa gctggttgat gccaactcgg taagagtcgc    7765
cacctgcagc atcagtggag gtggagctgt cactggaatc gcttgagcac gaagccaacg    7825
ccaaggcgcc aacagtaaag atgcttgcga gtaccttcga acgggaagaa acatagcac    7885 atctccttaa agtgttattt tcaaaaaggg gcagacagcg tcaacacatg tctcggataa    7945
agaaccatat gtgaaatgtc tcatgattta aactacttgt tctaccagtc atatgcgcaa    8005
ttccccctgg atatcccgca ggacatggac aaaatgggtg gatagcgggt gcaccaattc    8065
aatcttttaa aggccctaga caccgcgatt tccttaatcg atcattaaag agggatcctc    8125 tccctaaca aacctccaaa gactagagtg gggaacacca tgaacgtttc ctcaaataaa    8185
cccagtgact ctgaccgcga atatcttcaa tcagaactca cccggctcgt tggccagggg    8245
cgactcgatc tagatactta ccaagacgtg gttgataccg tttggtctac tgatgatcta    8305
ggcgagttga tgaggatccg tgcccgcttc ctggagggc gcaggtttc gcagcagcgg    8365
```

-continued

```
cccagcagc cgcagcaacc acatcagcgg ccgcaacagc aaccgccaca gcattatgga    8425
caacccggct acggccaatc acctcaatat ccaccgcagc agcctccgca taatcagccc    8485
ggctattacc ccgatcccgg ccctggccag cagcaaccac cgatgcacca gccaccaacg    8545
cgtccaaatc a                                                         8556
```

<210> SEQ ID NO 34
<211> LENGTH: 922
<212> TYPE: PRT
<213> ORGANISM: Brevibacterium lactofermentum ATCC13869

<400> SEQUENCE: 34

```
Met Ala Asp Gln Ala Lys Leu Gly Gly Lys Pro Ser Asp Asp Ser Asn
1               5                   10                  15

Phe Ala Met Ile Arg Asp Gly Val Ala Ser Tyr Leu Asn Asp Ser Asp
                20                  25                  30

Pro Glu Glu Thr Asn Glu Trp Met Asp Ser Leu Asp Gly Leu Leu Gln
            35                  40                  45

Glu Ser Ser Pro Glu Arg Ala Arg Tyr Leu Met Leu Arg Leu Leu Glu
        50                  55                  60

Arg Ala Ser Ala Lys Arg Val Ser Leu Pro Pro Met Thr Ser Thr Asp
65                  70                  75                  80

Tyr Val Asn Thr Ile Pro Thr Ser Met Glu Pro Glu Phe Pro Gly Asp
                85                  90                  95

Glu Glu Met Glu Lys Arg Tyr Arg Arg Trp Ile Arg Trp Asn Ala Ala
            100                 105                 110

Ile Met Val His Arg Ala Gln Arg Pro Gly Ile Gly Val Gly Gly His
        115                 120                 125

Ile Ser Thr Tyr Ala Gly Ala Ala Pro Leu Tyr Glu Val Gly Phe Asn
130                 135                 140

His Phe Phe Arg Gly Lys Asp His Pro Gly Gly Gly Asp Gln Ile Phe
145                 150                 155                 160

Phe Gln Gly His Ala Ser Pro Gly Met Tyr Ala Arg Ala Phe Met Glu
                165                 170                 175

Gly Arg Leu Ser Glu Asp Asp Leu Asp Gly Phe Arg Gln Glu Val Ser
            180                 185                 190

Arg Glu Gln Gly Gly Ile Pro Ser Tyr Pro His Pro His Gly Met Lys
        195                 200                 205

Asp Phe Trp Glu Phe Pro Thr Val Ser Met Gly Leu Gly Pro Met Asp
    210                 215                 220

Ala Ile Tyr Gln Ala Arg Phe Asn Arg Tyr Leu Glu Asn Arg Gly Ile
225                 230                 235                 240

Lys Asp Thr Ser Asp Gln His Val Trp Ala Phe Leu Gly Asp Gly Glu
                245                 250                 255

Met Asp Glu Pro Glu Ser Arg Gly Leu Ile Gln Gln Ala Ala Leu Asn
            260                 265                 270

Asn Leu Asp Asn Leu Thr Phe Val Val Asn Cys Asn Leu Gln Arg Leu
        275                 280                 285

Asp Gly Pro Val Arg Gly Asn Thr Lys Ile Ile Gln Glu Leu Glu Ser
    290                 295                 300

Phe Phe Arg Gly Ala Gly Trp Ser Val Ile Lys Val Val Trp Gly Arg
305                 310                 315                 320

Glu Trp Asp Glu Leu Leu Glu Lys Asp Gln Asp Gly Ala Leu Val Glu
                325                 330                 335
```

```
Ile Met Asn Asn Thr Ser Asp Gly Asp Tyr Gln Thr Phe Lys Ala Asn
            340                 345                 350

Asp Gly Ala Tyr Val Arg Glu His Phe Gly Arg Asp Pro Arg Thr
        355                 360                 365

Ala Lys Leu Val Glu Asn Met Thr Asp Glu Ile Trp Lys Leu Pro
    370                 375                 380

Arg Gly Gly His Asp Tyr Arg Lys Val Tyr Ala Ala Tyr Lys Arg Ala
385                 390                 395                 400

Leu Glu Thr Lys Asp Arg Pro Thr Val Ile Leu Ala His Thr Ile Lys
                405                 410                 415

Gly Tyr Gly Leu Gly His Asn Phe Glu Gly Arg Asn Ala Thr His Gln
                420                 425                 430

Met Lys Lys Leu Thr Leu Asp Asp Leu Lys Leu Phe Arg Asp Lys Gln
            435                 440                 445

Gly Ile Pro Ile Thr Asp Glu Gln Leu Glu Lys Asp Pro Tyr Leu Pro
450                 455                 460

Pro Tyr Tyr His Pro Gly Glu Asp Ala Pro Glu Ile Lys Tyr Met Lys
465                 470                 475                 480

Glu Arg Arg Ala Ala Leu Gly Gly Tyr Leu Pro Glu Arg Arg Glu Asn
                485                 490                 495

Tyr Asp Pro Ile Gln Val Pro Pro Leu Asp Lys Leu Arg Ser Val Arg
            500                 505                 510

Lys Gly Ser Gly Lys Gln Gln Ile Ala Thr Thr Met Ala Thr Val Arg
    515                 520                 525

Thr Phe Lys Glu Leu Met Arg Asp Lys Gly Leu Ala Asp Arg Leu Val
    530                 535                 540

Pro Ile Ile Pro Asp Glu Ala Arg Thr Phe Gly Leu Asp Ser Trp Phe
545                 550                 555                 560

Pro Thr Leu Lys Ile Tyr Asn Pro His Gly Gln Asn Tyr Val Pro Val
                565                 570                 575

Asp His Asp Leu Met Leu Ser Tyr Arg Glu Ala Pro Glu Gly Gln Ile
            580                 585                 590

Leu His Glu Gly Ile Asn Glu Ala Gly Ser Val Ala Ser Phe Ile Ala
    595                 600                 605

Ala Gly Thr Ser Tyr Ala Thr His Gly Lys Ala Met Ile Pro Leu Tyr
    610                 615                 620

Ile Phe Tyr Ser Met Phe Gly Phe Gln Arg Thr Gly Asp Ser Ile Trp
625                 630                 635                 640

Ala Ala Ala Asp Gln Met Ala Arg Gly Phe Leu Leu Gly Ala Thr Ala
                645                 650                 655

Gly Arg Thr Thr Leu Thr Gly Glu Gly Leu Gln His Met Asp Gly His
            660                 665                 670

Ser Pro Val Leu Ala Ser Thr Asn Glu Gly Val Glu Thr Tyr Asp Pro
        675                 680                 685

Ser Phe Ala Tyr Glu Ile Ala His Leu Val His Arg Gly Ile Asp Arg
    690                 695                 700

Met Tyr Gly Pro Gly Lys Gly Glu Asp Val Ile Tyr Tyr Ile Thr Ile
705                 710                 715                 720

Tyr Asn Glu Pro Thr Pro Gln Pro Ala Glu Pro Glu Gly Leu Asp Val
                725                 730                 735

Glu Gly Leu His Lys Gly Ile Tyr Leu Tyr Ser Arg Gly Glu Gly Thr
            740                 745                 750

Gly His Glu Ala Asn Ile Leu Ala Ser Gly Val Gly Met Gln Trp Ala
```

```
                    755                 760                 765
Leu Lys Ala Ala Ser Ile Leu Glu Ala Asp Tyr Gly Val Arg Ala Asn
    770                 775                 780

Ile Tyr Ser Ala Thr Ser Trp Val Asn Leu Ala Arg Asp Gly Ala Ala
785                 790                 795                 800

Arg Asn Lys Ala Gln Leu Arg Asn Pro Gly Asp Ala Gly Glu Ala
                805                 810                 815

Phe Val Thr Thr Gln Leu Lys Gln Thr Ser Gly Pro Tyr Val Ala Val
                820                 825                 830

Ser Asp Phe Ser Thr Asp Leu Pro Asn Gln Ile Arg Glu Trp Val Pro
                835                 840                 845

Gly Asp Tyr Thr Val Leu Gly Ala Asp Gly Phe Gly Phe Ser Asp Thr
    850                 855                 860

Arg Pro Ala Ala Arg Arg Phe Phe Asn Ile Asp Ala Glu Ser Ile Val
865                 870                 875                 880

Val Ala Val Leu Asn Ser Leu Ala Arg Glu Gly Lys Ile Asp Val Ser
                885                 890                 895

Val Ala Ala Gln Ala Ala Glu Lys Phe Lys Leu Asp Asp Pro Thr Ser
                900                 905                 910

Val Ser Val Asp Pro Asn Ala Pro Glu Glu
    915                 920

<210> SEQ ID NO 35
<211> LENGTH: 20
<212> TYPE: DNA
<213> ORGANISM: Artificial sequence
<220> FEATURE:
<223> OTHER INFORMATION: Synthetic DNA

<400> SEQUENCE: 35
aatgccagga gtcaacaccc                                            20

<210> SEQ ID NO 36
<211> LENGTH: 20
<212> TYPE: DNA
<213> ORGANISM: Artificial sequence
<220> FEATURE:
<223> OTHER INFORMATION: Synthetic DNA

<400> SEQUENCE: 36
acatggaaca ggcaattcgc                                            20

<210> SEQ ID NO 37
<211> LENGTH: 28
<212> TYPE: DNA
<213> ORGANISM: Artificial sequence
<220> FEATURE:
<223> OTHER INFORMATION: Synthetic DNA

<400> SEQUENCE: 37
cgtcccgggc tgtaaaacaa atcttcgg                                   28

<210> SEQ ID NO 38
<211> LENGTH: 27
<212> TYPE: DNA
<213> ORGANISM: Artificial sequence
<220> FEATURE:
<223> OTHER INFORMATION: Synthetic DNA

<400> SEQUENCE: 38
atccccgggc ttaccaccaa gttttgc                                    27
```

```
<210> SEQ ID NO 39
<211> LENGTH: 30
<212> TYPE: DNA
<213> ORGANISM: Artificial sequence
<220> FEATURE:
<223> OTHER INFORMATION: Synthetic DNA

<400> SEQUENCE: 39
cttatgcgtt gccacattcg tgcacttcgg                                    30

<210> SEQ ID NO 40
<211> LENGTH: 40
<212> TYPE: DNA
<213> ORGANISM: Artificial sequence
<220> FEATURE:
<223> OTHER INFORMATION: Synthetic DNA

<400> SEQUENCE: 40
gcgttgaccc attcgtgcac ttcggtgtgc tataattagg                         40

<210> SEQ ID NO 41
<211> LENGTH: 40
<212> TYPE: DNA
<213> ORGANISM: Artificial sequence
<220> FEATURE:
<223> OTHER INFORMATION: Synthetic DNA

<400> SEQUENCE: 41
gcgttgccac attcgtgcac ttcggtgtgc tataattagg                         40

<210> SEQ ID NO 42
<211> LENGTH: 38
<212> TYPE: DNA
<213> ORGANISM: Artificial sequence
<220> FEATURE:
<223> OTHER INFORMATION: Synthetic DNA

<400> SEQUENCE: 42
ttttaaaacg ttctggagaa gactcctgga gtaatccg                           38

<210> SEQ ID NO 43
<211> LENGTH: 20
<212> TYPE: DNA
<213> ORGANISM: Artificial sequence
<220> FEATURE:
<223> OTHER INFORMATION: Synthetic DNA

<400> SEQUENCE: 43
cgatcttgcc ttcgcgtgcc                                               20

<210> SEQ ID NO 44
<211> LENGTH: 30
<212> TYPE: DNA
<213> ORGANISM: Artificial sequence
<220> FEATURE:
<223> OTHER INFORMATION: Synthetic DNA

<400> SEQUENCE: 44
agaccgccgg agtatgcaag aacgatgcgg                                    30

<210> SEQ ID NO 45
<211> LENGTH: 30
<212> TYPE: DNA
<213> ORGANISM: Artificial sequence
<220> FEATURE:
```

<223> OTHER INFORMATION: Synthetic DNA

<400> SEQUENCE: 45
gacttcacca tcaatcatct tcttcaggta                                30

<210> SEQ ID NO 46
<211> LENGTH: 30
<212> TYPE: DNA
<213> ORGANISM: Artificial sequence
<220> FEATURE:
<223> OTHER INFORMATION: Synthetic DNA

<400> SEQUENCE: 46
accttcgacc agaccctggc taagggcttt                                30

<210> SEQ ID NO 47
<211> LENGTH: 30
<212> TYPE: DNA
<213> ORGANISM: Artificial sequence
<220> FEATURE:
<223> OTHER INFORMATION: Synthetic DNA

<400> SEQUENCE: 47
gctaacaagc gcgatcgcga agctggcaac                                30

<210> SEQ ID NO 48
<211> LENGTH: 25
<212> TYPE: DNA
<213> ORGANISM: Artificial sequence
<220> FEATURE:
<223> OTHER INFORMATION: Synthetic DNA

<400> SEQUENCE: 48
gcgatgacac cgttttttgtt ctcgc                                    25

<210> SEQ ID NO 49
<211> LENGTH: 25
<212> TYPE: DNA
<213> ORGANISM: Artificial sequence
<220> FEATURE:
<223> OTHER INFORMATION: Synthetic DNA

<400> SEQUENCE: 49
ggcgacatcc ttgcccagat gatca                                     25

<210> SEQ ID NO 50
<211> LENGTH: 25
<212> TYPE: DNA
<213> ORGANISM: Artificial sequence
<220> FEATURE:
<223> OTHER INFORMATION: Synthetic DNA

<400> SEQUENCE: 50
gacttcacca tcaatcatct tcttc                                     25

<210> SEQ ID NO 51
<211> LENGTH: 24
<212> TYPE: DNA
<213> ORGANISM: Artificial sequence
<220> FEATURE:
<223> OTHER INFORMATION: Synthetic DNA

<400> SEQUENCE: 51
gccaggtaca actgtctgaa ttgc                                      24

<210> SEQ ID NO 52
<211> LENGTH: 40
<212> TYPE: DNA
<213> ORGANISM: Artificial sequence
<220> FEATURE:
<223> OTHER INFORMATION: Synthetic DNA

<400> SEQUENCE: 52
gttaatcgct tgccaatgca ggcaggtaag gtataacccg                40

<210> SEQ ID NO 53
<211> LENGTH: 40
<212> TYPE: DNA
<213> ORGANISM: Artificial sequence
<220> FEATURE:
<223> OTHER INFORMATION: Synthetic DNA

<400> SEQUENCE: 53
gttaatcgct tgctaatgca ggcaggtaag gtataacccg                40

<210> SEQ ID NO 54
<211> LENGTH: 40
<212> TYPE: DNA
<213> ORGANISM: Artificial sequence
<220> FEATURE:
<223> OTHER INFORMATION: Synthetic DNA

<400> SEQUENCE: 54
gttaatcgct tgtcaatgca ggcaggtaag gtataacccg                40

<210> SEQ ID NO 55
<211> LENGTH: 40
<212> TYPE: DNA
<213> ORGANISM: Artificial sequence
<220> FEATURE:
<223> OTHER INFORMATION: Synthetic DNA

<400> SEQUENCE: 55
gttaatcgct tgttaatgca ggcaggtaag gtataatccg                40

<210> SEQ ID NO 56
<211> LENGTH: 40
<212> TYPE: DNA
<213> ORGANISM: Artificial sequence
<220> FEATURE:
<223> OTHER INFORMATION: Synthetic DNA

<400> SEQUENCE: 56
gttaatcgct tgtcaatgca ggcaggtaag gtataatccg                40

<210> SEQ ID NO 57
<211> LENGTH: 30
<212> TYPE: DNA
<213> ORGANISM: Artificial sequence
<220> FEATURE:
<223> OTHER INFORMATION: Synthetic DNA

<400> SEQUENCE: 57
gggttccagc ctcgtgcgga attcgtggag                           30

<210> SEQ ID NO 58
<211> LENGTH: 25
<212> TYPE: DNA
<213> ORGANISM: Artificial sequence
<220> FEATURE:
<223> OTHER INFORMATION: Synthetic DNA

```
<400> SEQUENCE: 58
gcgttaccca gagctggatc ctcgg                                              25

<210> SEQ ID NO 59
<211> LENGTH: 16
<212> TYPE: DNA
<213> ORGANISM: Artificial sequence
<220> FEATURE:
<223> OTHER INFORMATION: Synthetic DNA

<400> SEQUENCE: 59
cagttgtggc tgatcg                                                        16

<210> SEQ ID NO 60
<211> LENGTH: 17
<212> TYPE: DNA
<213> ORGANISM: Artificial sequence
<220> FEATURE:
<223> OTHER INFORMATION: Synthetic DNA

<400> SEQUENCE: 60
ctttcccaga ctctggc                                                       17

<210> SEQ ID NO 61
<211> LENGTH: 21
<212> TYPE: DNA
<213> ORGANISM: Artificial sequence
<220> FEATURE:
<223> OTHER INFORMATION: Synthetic DNA

<400> SEQUENCE: 61
gctataattt gacgtgagca t                                                  21

<210> SEQ ID NO 62
<211> LENGTH: 25
<212> TYPE: DNA
<213> ORGANISM: Artificial sequence
<220> FEATURE:
<223> OTHER INFORMATION: Synthetic DNA

<400> SEQUENCE: 62
gctcacgtca aattatagca gtgtc                                              25

<210> SEQ ID NO 63
<211> LENGTH: 54
<212> TYPE: DNA
<213> ORGANISM: Artificial sequence
<220> FEATURE:
<223> OTHER INFORMATION: Synthetic DNA

<400> SEQUENCE: 63
ttgttgtcat tctgtgcgac actgctataa tttgaacgtg agcagttaac agcc              54

<210> SEQ ID NO 64
<211> LENGTH: 63
<212> TYPE: DNA
<213> ORGANISM: Artificial sequence
<220> FEATURE:
<223> OTHER INFORMATION: Synthetic DNA

<400> SEQUENCE: 64
gttaactgct cacgttcaaa ttatagcagt gtcgcacaga atgacaacaa agaattaaaa        60
ttg                                                                      63
```

-continued

```
<210> SEQ ID NO 65
<211> LENGTH: 25
<212> TYPE: DNA
<213> ORGANISM: Artificial sequence
<220> FEATURE:
<223> OTHER INFORMATION: Synthetic DNA

<400> SEQUENCE: 65
gctagcctcg ggagctctct aggag                                          25

<210> SEQ ID NO 66
<211> LENGTH: 25
<212> TYPE: DNA
<213> ORGANISM: Artificial Sequence
<220> FEATURE:
<223> OTHER INFORMATION: Synthetic DNA

<400> SEQUENCE: 66
gatctttccc agactctggc cacgc                                          25
```